US012624116B2

(12) United States Patent

Gromada et al.

(10) Patent No.: US 12,624,116 B2

(45) Date of Patent: *May 12, 2026

(54) METHODS OF TREATING SEVERE INSULIN RESISTANCE BY INTERFERING WITH GLUCAGON RECEPTOR SIGNALING

(71) Applicant: Regeneron Pharmaceuticals, Inc., Tarrytown, NY (US)

(72) Inventors: Jesper Gromada, Scarsdale, NY (US); Haruka Okamoto, New York, NY (US); Stephen Jaspers, Brewster, NY (US); Joyce Harp, Montclair, NJ (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 288 days.

This patent is subject to a terminal disclaimer.

(21) Appl. No.: 18/329,358

(22) Filed: Jun. 5, 2023

(65) Prior Publication Data

US 2023/0416384 A1 Dec. 28, 2023

Related U.S. Application Data

(60) Continuation of application No. 17/222,236, filed on Apr. 5, 2021, now Pat. No. 11,708,416, which is a division of application No. 16/328,935, filed as application No. PCT/US2017/049137 on Aug. 29, 2017, now Pat. No. 10,995,146.

(60) Provisional application No. 62/411,032, filed on Oct. 21, 2016, provisional application No. 62/381,263, filed on Aug. 30, 2016.

(51) Int. Cl.

| | |
|---|---|
| *C07K 16/28* | (2006.01) |
| *A61K 38/16* | (2006.01) |
| *A61K 39/395* | (2006.01) |
| *A61K 45/06* | (2006.01) |
| *A61P 3/10* | (2006.01) |
| *C07K 16/26* | (2006.01) |
| *A61K 39/00* | (2006.01) |

(52) U.S. Cl.

CPC .......... *C07K 16/2869* (2013.01); *A61K 38/16* (2013.01); *A61K 39/3955* (2013.01); *A61K 45/06* (2013.01); *A61P 3/10* (2018.01); *C07K 16/26* (2013.01); *C07K 16/28* (2013.01); *A61K 2039/505* (2013.01); *A61K 2039/507* (2013.01); *A61K 2039/54* (2013.01); *A61K 2039/545* (2013.01); *C07K 2317/21* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search

CPC .......... C07K 16/2869; C07K 2317/76; C07K 16/28; C07K 16/26; A61K 2039/507; A61K 2039/505

See application file for complete search history.

(56) References Cited

U.S. PATENT DOCUMENTS

| | | | |
|---|---|---|---|
| 4,206,199 | A | 6/1980 | Fujino et al. |
| 4,221,777 | A | 9/1980 | Nishino |
| 4,272,433 | A | 6/1981 | Nishino |
| 4,407,965 | A | 10/1983 | Yanaihara |
| 4,423,034 | A | 12/1983 | Nakagawa et al. |
| 4,816,567 | A | 3/1989 | Cabilly et al. |
| 4,946,778 | A | 8/1990 | Ladner et al. |
| 5,712,105 | A | 1/1998 | Yanaihara et al. |
| 5,770,445 | A | 6/1998 | Kindsvogel et al. |
| 7,947,809 | B2 | 5/2011 | Yan et al. |
| 8,545,847 | B2 | 10/2013 | Okamoto et al. |
| 10,233,250 | B2 | 3/2019 | Okamoto et al. |
| 2004/0101920 | A1 | 5/2004 | Radziejewski et al. |
| 2009/0041784 | A1 | 2/2009 | Yan et al. |
| 2009/0252727 | A1 | 10/2009 | Korytko, Jr. et al. |

(Continued)

FOREIGN PATENT DOCUMENTS

| | | |
|---|---|---|
| EP | 0658200 B1 | 12/2004 |
| EP | 2074149 B1 | 6/2013 |

(Continued)

OTHER PUBLICATIONS

Damond et al. (2016) "Blockade of Glucagon Signaling Prevents or Reverses Diabetes Onset Only if Residual B-cells Persist," eLife 5, Article e13828, 1-18.

(Continued)

*Primary Examiner* — Gyan Chandra

(74) *Attorney, Agent, or Firm* — FisherBroyles, LLP; Cara L. Crowley-Weber; Trisha Agrawal

(57) ABSTRACT

Provided herein are methods of treating a patient with severe insulin resistance. The methods comprise administering to a patient in need thereof a therapeutic amount of a GCG/GCGR signaling pathway inhibitor, such that blood glucose or beta-hydroxybutyrate levels are lowered or that the severe insulin resistance is mediated, or a condition or disease characterized by severe insulin resistance is mediated, or at least one symptom or complication associated with the condition or disease is alleviated or reduced in severity. The GCG/GCGR signaling pathway inhibitor can be a small molecule inhibitor of the signaling pathway, an antisense inhibitor of the signaling pathway, a GCG neutralizing monoclonal antibody, a GCGR antagonist, a peptide inhibitor of the signaling pathway, a DARPin, a Spiegelmer, an aptamer, engineered Fn type-III domains, etc. The therapeutic methods are useful for treating a human suffering from severe insulin resistance.

18 Claims, 9 Drawing Sheets

Specification includes a Sequence Listing.

(56) References Cited

U.S. PATENT DOCUMENTS

| | | | |
|---|---|---|---|
| 2011/0223160 A1 | 9/2011 | Yan et al. | |
| 2011/0306624 A1 | 12/2011 | Lin et al. | |
| 2016/0075778 A1 | 3/2016 | Okamoto et al. | |
| 2019/0218301 A1 | 7/2019 | Gromada et al. | |

FOREIGN PATENT DOCUMENTS

| | | | |
|---|---|---|---|
| WO | 2005/065680 A1 | 7/2005 | |
| WO | 2005/103081 A2 | 11/2005 | |
| WO | 2005/121097 A2 | 12/2005 | |
| WO | 2005/123688 A2 | 12/2005 | |
| WO | 2006/014618 A2 | 2/2006 | |
| WO | 2006/017055 A2 | 2/2006 | |
| WO | 2006/086488 A2 | 8/2006 | |
| WO | 2006/102067 A1 | 9/2006 | |
| WO | 2006/104826 A2 | 10/2006 | |
| WO | 2007/047676 A1 | 4/2007 | |
| WO | 2007/124463 A1 | 11/2007 | |
| WO | 2008/036341 A2 | 3/2008 | |
| WO | 2008/042223 A1 | 4/2008 | |
| WO | 2008/098244 A1 | 8/2008 | |
| WO | 2009/140342 A1 | 11/2009 | |
| WO | 2010/030722 A1 | 3/2010 | |
| WO | 2010/071750 A1 | 6/2010 | |
| WO | 2010/088061 A1 | 8/2010 | |
| WO | 2010/098994 A1 | 9/2010 | |
| WO | 2011/007722 A1 | 1/2011 | |
| WO | 2012/071372 A2 | 5/2012 | |
| WO | 2013/043817 | 3/2013 | |
| WO | 2013/081993 A1 | 6/2013 | |
| WO | 2014/181229 A2 | 11/2014 | |
| WO | 2016/044337 A1 | 3/2016 | |

OTHER PUBLICATIONS

Diamant et al. (2012) "Liraglutide Treatment in a Patient With HIV and Uncontrolled Insulin-Treated Type 2 Diabetes," Diabetes Care 35, p. e34.

AL-Lazikani (1997) "Standard Conformations for the Canonical Structures of Immunoglobulins," J Mol. Biol., 273:927-948.

Allen (1999) The Art, Science and Technology of Pharmaceutical Compounding, 8pgs.

Burcelin et al. (1995) "Cloning and Sequence Analysis of the Murine Glucagon Receptor-Encoding Gene," Gene., 164(2):305-310.

Chakravarty et al. (2005) "Factors that Control the Tissue-Specific Transcription of The Gene for Phosphoenolpyruvate Carboxykinase-C," Crit. Rev. Biochem. Mol. Biol., 40(3): 129-154.

Church and Haines (2016) "Treatment Approach to Patients With Severe Insulin Resistance," Clin. Diabetes, 34(2):97-104.

Cochran et al. (2004) "Efficacy of Recombinant Methionyl Human Leptin Therapy for The Extreme Insulin Resistance of the Rabson-Mendenhall syndrome," Journal of Clinical Endocrinology and Metabolism, 89:1548-1554.

De Laszlo et al. (1999) "Potent, Orally Absorbed Glucagon Receptor Antagonists," Bioorg. Med. Chem. Lett., 9(5):641-646.

Desbois-Mouthon et al. (1997) "Major Circadian Variations of Glucose Homeostasis in a Patient with Rabson-Mendenhall Syndrome and Primary Insulin Resistance Due to a Mutation (Cys284-->Tyr) in The Insulin Receptor Alpha-Subunit", Pediatr. Res., 42(1):72-77.

German et al. (2010) "Leptin Deficiency Causes Insulin Resistance Induced by Uncontrolled Diabetes," Diabetes, 59(7):1626-1634.

Gusarova et al. (2014) "ANGPTL8/Betatrophin Does Not Control Pancreatic Beta Cell Expansion," Cell, 159:691-696.

Harlow & Lane (1988) "Antibodies: A Laboratory Manual," Cold Spring Harbor Lab., Cold Spring Harbor, N.Y.

Kabat, (1991) "Sequences of Proteins of Immunological Interest," National Institutes of Health, Bethesda, Md.

Köhler and Milstein (1975) "Continuous Cultures of Fused Cells Secreting Antibody of Predefined Specificity," Nature 256(5517):495-497.

Kufer et al. (2004) "A Revival of Bispecific Antibodies," Trends Biotechnol., 22:238-244.

Langer (1990) "New Methods of Drug Delivery," Science, 249:1527-1533.

Lee, et al. (2016) "Glucagon Is The Key Factor in the Development of Diabetes," Diabetologia, 59:1372-1375.

Longo et al. (1999) "Progressive Decline in Insulin Levels in Rabson-Mendenhall Syndrome," Journal of Clinical Endocrinology & Metabolism, 84(8):2623-2629.

Lindström (2010) "B-Cell Function in Obese-Hyperglycemic Mice [ob/ob Mice]," In: Islam M. (eds) The Islets of Langerhans. Advances in Experimental Medicine and Biology, 654:767-784; Springer, Dordrecht. https://doi.org/10.1007/978-90-481-3271-3_20.

Lynedijian et al. (1995) "Glucokinase and Cytosolic Phosphenolpyruvate Carboxykinase (GTP) in the Human Liver," J Clin Invest., 95(5):1966-73.

Martin et al. (1989) "Modeling Antibody Hypervariable Loops: A Combined Algorithm," Proc. Natl. Acad. Sci. USA, 86:9268-9272.

McCafferty et al. (1990) "Phage Antibodies: Filamentous Phage Displaying Antibody Variable Domains," Nature, 348:552-554.

McNally et al. (2004) "Cloning and Characterization of The Glucagon Receptor From Cynomologous Monkey," Peptides, 25(7):1171-1178.

Melvin et al. (2017) "Severe Insulin Resistance: Pathologies," Practical Diabetes, 34(6):189-194a.

Moller and Flier (1991) "Insulin Resistance—Mechanisms, Syndromes, and Implications," New England Journal of Medicine, 325(13):938-948.

Muller et al. (1970) "Abnormal Alpha-Cell Function," N Eng J Med, 283: 109-115.

Okamoto et al. (2015) "Glucagon Receptor Blockade With a Human Antibody Normalizes Blood Glucose in Diabetic Mice and Monkeys," Endocrinology, 156(8): 2781-2794.

Okamoto et al. (2017) "Glucagon Receptor Inhibition Normalizes Blood Glucose in Severe Insulin-Resistant Mice," Proceedings National Academy of Sciences PNAS, 114(10):2753-2758.

Parker et al. (2013) "Genetic Forms of Sever Insulin Resistance: What Endocrinologists Should Know," European Journal of Endocrinology, 169:R71-R80.

Pittner and Fain, (1991) "Activation of Membrane Protein Kinase C by Glucagon and Ca2+-Mobilizing Hormones in Cultured Rat Heaptocytes," Biochem. J., 277:371-378.

Powell et al. (1998) "Compendium of Excipients for Parenteral Formulations," PDA J Pharm Sci Technol., 52:238-311.

Rucktäschel et al. (2000) "Regulation by Glucagon (cAMP) and Insulin of The Promoter of The Human Phosphoenolpyruvate Carboxykinase Gene (Cytosolic) in Cultured Rat Heatocytes and in Human Hepatoblastoma Cells," 352 Pt 1:211-7.

Savage et al. (2014) "Insulin Resistance Syndrome," Diapedia, Retrieved from URL:https://doi.org/10.14496/dia.410408512).

Schäffer et al. (2008) "A Novel High-Affinity Peptide Antagonist to The Insulin Receptor," Biochem. Biophys. Res. Commun., 376(2):380-383.

Semple et al. (2011) "Genetic Syndromes of Severe Insulin Resistance," Endocrine Reviews, 32(4):498-514.

Tritos and Mantzoros (1998) "Clinical review 97: Syndromes of severe insulin resistance," Journal of Clinical Endocrinology and Metabolism, 83:3025-3030.

Tutt et al. (1991) "Trispecific F(ab')3 Derivatives That Use Cooperative Signaling Via The TCR/CD3 Complex and CD2 to Activate and Redirect Resting Cytotoxic T Cells," J. Immunol., 147:60-69.

Unson et al. (1989) "Biological Activities of des-His1 [Glu9]Glucagon Amide, a Glucagon Antagonist1," Peptides, 10:1171-1177.

Vestergaard et al. (1997) "Short- and Long-Term Metabolic Effects of Recombinant Human IGF-I Treatment in Patients With Severe Insulin Resistance and Diabetes Mellitus," European Journal of Endocrinology, 136(5):475-482.

Wakelam et al. (1986) "Activation of Two-Signal-Transduction Systems in Hepatocytes by Glucagon," Nature, 323:68-71.

(56)                    References Cited

OTHER PUBLICATIONS

West et al. (1975) "Familial Insulin-Resistant Diabetes, Multiple Somatic Anomalies, and Pineal Hyperplasia," Arch. Dis. Child., 50(9):703-708.

Wu and Wu et al. (1987) "Receptor-Mediated in Vitro Gene Transformation by a Soluble DNA Carrier System*," J. Biol. Chem., 262:4429-4432.

Yi et al. (2013) "Betatrophin: A Hormone That Controls Pancreatic β Cell Proliferation," Cell, 153:747-758.

International Search Report and Written Opinion, PCT/US2017/049137, mailed Nov. 7, 2017, 14 pages.

Control                H4H1327P            Control + S961        H4H1327P + S961

Pepck

β-actin

METHODS OF TREATING SEVERE INSULIN RESISTANCE BY INTERFERING WITH GLUCAGON RECEPTOR SIGNALING

CROSS-REFERENCE TO RELATED APPLICATIONS

This application is a continuation application of U.S. patent application Ser. No. 17/222,236, filed on Apr. 5, 2021, which is a divisional application of U.S. 371 National Phase patent application Ser. No. 16/328,935, filed Feb. 27, 2019, which is the National Stage Application of PCT/US2017/049137, filed Aug. 29, 2017, which claims the benefit under 35 USC § 119 (e) of U.S. Provisional Application No. 62/411,032, filed Oct. 21, 2016, and to U.S. Provisional Application No. 62/381,263, filed Aug. 30, 2016, each of which are incorporated herein by reference. To the extent appropriate, a claim of priority is made to each of the above-disclosed applications.

TECHNICAL FIELD

The invention relates to methods of using a glucagon (GCG) inhibitor or a glucagon receptor (GCGR) antagonist to treat or to slow the progression of severe insulin resistance, and/or reducing the therapeutic insulin dose in a patient in need thereof.

SEQUENCE LISTING

An official copy of the sequence listing is submitted concurrently with the specification electronically via Patent Center. The contents of the electronic sequence listing (10282US03_Sequence_Listing_ST26.xml; Size 368,640 bytes; and Date of Creation: Jun. 5, 2023) is part of the specification and is herein incorporated by reference in its entirety.

BACKGROUND

Glucagon is a 29 residue polypeptide hormone, which in cooperation with insulin, mediates homeostatic regulation of the amount of glucose in the blood. Glucagon primarily acts by stimulating certain cells, for example, liver cells, to release glucose when blood glucose levels fall to maintain normal blood glucose levels. The action of glucagon is opposite to that of insulin, which stimulates cells to take up and store glucose whenever blood glucose levels rise. Glucagon is produced in the alpha cells of the pancreas, whereas insulin is secreted from the neighboring beta cells.

It is an imbalance of glucagon and insulin that may play an important role in several diseases, such as diabetes mellitus and diabetic ketoacidosis. In particular, studies have shown that higher basal glucagon levels and lack of suppression of postprandial glucagon secretion contribute to diabetic conditions in humans (Muller et al. (1970), N Eng J Med, 283:109-115).

It is believed that glucagon's effects on elevating blood glucose levels are mediated in part by the activation of certain cellular pathways following the binding of glucagon (GCG) to its receptor (designated GCGR). GCGR is a member of the secretin subfamily (family B) of G-protein-coupled receptors and is predominantly expressed in the liver. The binding of glucagon to its receptor triggers a G-protein signal transduction cascade, activating intracellular cyclic AMP and leading to an increase in glucose output through de novo synthesis (gluconeogenesis) and glycogen breakdown (glycogenolysis) (Wakelam et al., (1986) Nature, 323:68-71; Unson et al., (1989) Peptides, 10:1171-1177; and Pittner and Fain, (1991) Biochem. J., 277:371-378).

The action of glucagon can be suppressed by providing an antagonist, such as a small molecule inhibitor, a GCG antibody, or a GCGR antibody, as described herein. Anti-GCG antibodies are mentioned, e.g., in U.S. Pat. Nos. 4,206,199; 4,221,777; 4,423,034; 4,272,433; 4,407,965; 5,712,105; and in PCT publications WO2007/124463 and WO2013/081993. Anti-GCGR antibodies are described in U.S. Pat. Nos. 5,770,445, 7,947,809, and 8,545,847; European patent application EP2074149A2; EP patent EP0658200B1; US patent publications 2009/0041784; 2009/0252727; and 2011/0223160; and PCT publication WO2008/036341. Small molecule inhibitors of GCG or GCGR are mentioned, e.g. in WO 07/47676; WO 06/86488; WO 05/123688; WO 05/121097; WO 06/14618; WO 08/42223; WO 08/98244; WO 2010/98948; US20110306624; WO 2010/98994; WO 2010/88061; WO 2010/71750; WO 2010/30722; WO 06/104826; WO 05/65680; WO 06/102067; WO 06/17055; WO 2011/07722; or WO 09/140342.

Severe insulin resistance syndromes are rare metabolic disorders in which patients do not respond well to insulin. Current treatments available for severe insulin resistance syndromes include regular feedings and very high doses of insulin in attempt to provide adequate glycemic control. Administration of IGF-I, while effective in the short term, failed to provide long-term glycemic control in patients with severe insulin resistance. Vestergaard et al., (1997) European Journal of Endocrinology, 136:475-482. Administration of recombinant leptin has shown some success in patients with Rabson-Mendenhall syndrome (RMS) by reducing blood glucose levels over several months. Cochran et al., (2004) Journal of Clinical Endocrinology and Metabolism, 89:1548-1554.

Given the absence of effective therapies to treat, or to slow the progression of severe insulin resistance disease, i.e., to extend the life and/or improve the quality of life of a patient having severe insulin resistance, there is a need to identify and explore the use of other agents for treating these diseases, such as the GCG/GCGR signaling pathway inhibitors and antagonists as described herein.

BRIEF SUMMARY

Provided herein are methods for treating a patient with a condition or disease characterized by severe insulin resistance by administering a GCG inhibitor or a GCGR antagonist, e.g. a pharmaceutical composition comprising a GCG inhibitor or GCGR antagonist. A GCG inhibitor or GCGR antagonist is a compound capable of blocking or inhibiting the glucagon receptor signaling pathway. The antagonist may take the form of a small molecule inhibitor, peptide inhibitor, CRISPR technology (Clustered regularly interspaced short palindromic repeats; CRISPR technology can generate GCGR knock-down or deletion of regulatory sequences affecting GCGR activity), an antisense inhibitor, DARPin, and a GCG or GCGR neutralizing monoclonal antibody. The GCG inhibitor or GCGR antagonist can be administered alone, in a pharmaceutical composition, or in conjunction with one or more therapeutic agents useful in treating a condition or disease associated with severe insulin resistance, or in treating one or more symptoms associated with the condition or disease, or in lowering blood glucose and/or ketones in a patient having a condition or disease associated with severe insulin resistance.

In some embodiments, methods are provided for lowering blood glucose levels and/or beta-hydroxybutyrate levels, or for decreasing ketonemia and/or ketoacidosis, or for treating a condition or disease associated with, or characterized in part by high blood glucose and/or ketonemia and/or ketoacidosis, or at least one symptom or complication associated with the condition or disease. In some aspects, the method comprises administering to a patient having severe insulin resistance a therapeutically effective amount of a composition comprising an inhibitor of GCG/GCGR signaling, such that blood glucose or beta-hydroxybutyrate levels are lowered or that the condition or disease is mediated, or at least one symptom or complication associated with the condition or disease is alleviated or reduced in severity. In some embodiments, the inhibitor of GCGR signaling is a GCGR antagonist, such as an anti-GCGR antibody. In some embodiments, the anti-GCGR antibody has a HCVR/LCVR sequence pair of SEQ ID NOs: 86/88. In some embodiments, the inhibitor of GCGR signaling is a GCG inhibitor, such as an anti-GCG antibody. In some embodiments, the anti-GCG antibody has a HCVR/LCVR sequence pair of SEQ ID NOs: 182/190. In some embodiments, the anti-GCG antibody has a HCVR/LCVR sequence pair of SEQ ID NOs: 166/174.

In some aspects, methods are provided for treating a patient with severe insulin resistance, wherein the patient exhibits elevated levels of blood glucose. The method comprises administering to the patient a therapeutically effective amount of a composition comprising a GCG inhibitor or a GCGR antagonist.

In some aspects, methods are provided for treating a patient with severe insulin resistance, wherein the patient does not exhibit elevated levels of blood glucose. The method comprises administering to the patient a therapeutically effective amount of a composition comprising a GCG inhibitor or a GCGR antagonist.

In some embodiments, methods are provided for reducing the amount and/or dosage of insulin necessary to treat a patient with severe insulin resistance, wherein the patient exhibits severe insulin resistance and/or elevated levels of blood glucose. In some aspects, the method comprises administering to the patient a therapeutically effective amount of a composition comprising a GCG inhibitor or a GCGR antagonist. In some aspects, the GCG inhibitor or GCGR antagonist is administered concomitantly with insulin. The amount and/or dosage of insulin may be reduced by about 30% to about 95%, or by about 90%, when administered concomitantly with an isolated human monoclonal antibody that binds specifically to the GCGR.

In some aspects, the GCGR antagonist can be an anti-GCGR antibody. The anti-GCGR antibody can inhibit or antagonize the GCGR. The anti-GCGR antibody can inhibit or block the GCGR signaling pathway. In some aspects, the GCG inhibitor can be an anti-GCG antibody. The anti-GCG antibody can inhibit binding of GCG to the GCGR.

In certain embodiments, the antibody or antigen-binding fragment specifically binds hGCGR, and comprises the heavy and light chain CDR domains contained within heavy and light chain sequence pairs selected from the group consisting of SEQ ID NO: 2/10, 18/26, 34/42, 50/58, 66/68, 70/78, 86/88, 90/98, 106/108, 110/118, 126/128, 130/138 and 146/148.

In certain embodiments, the antibody or antigen-binding fragment comprises the heavy and light chain CDR domains contained within the HCVR/LCVR amino acid sequence pair of SEQ ID NOs: 86/88.

In certain embodiments, the antibody or antigen-binding fragment comprises a HCVR/LCVR amino acid sequence pair of SEQ ID NOs: 86/88.

In one embodiment, the human antibody or antigen-binding fragment of a human antibody that binds hGCGR, comprises a heavy chain variable region (HCVR) having an amino acid sequence selected from the group consisting of SEQ ID NO: 2, 18, 34, 50, 66, 70, 86, 90, 106, 110, 126, 130 and 146, or a substantially similar sequence thereof having at least 90%, at least 95%, at least 98% or at least 99% sequence identity.

In one embodiment, the human antibody or antigen-binding fragment of a human antibody that binds hGCGR comprises a light chain variable region (LCVR) having an amino acid sequence selected from the group consisting of SEQ ID NO: 10, 26, 42, 58, 68, 78, 88, 98, 108, 118, 128, 138 and 148, or a substantially similar sequence thereof having at least 90%, at least 95%, at least 98% or at least 99% sequence identity.

In certain embodiments, the human antibody or fragment thereof that binds hGCGR comprises a HCVR/LCVR amino acid sequence pair selected from the group consisting of SEQ ID NO: 2/10, 18/26, 34/42, 50/58, 66/68, 70/78, 86/88, 90/98, 106/108, 110/118, 126/128, 130/138, and 146/148. In certain embodiments, the HCVR/LCVR amino acid sequence pair is selected from the group consisting of SEQ ID NO: 34/42, 70/78, 86/88, 110/118 and 126/128.

In certain embodiments, the isolated human antibody or an antigen-binding fragment thereof that binds specifically to hGCGR comprises a HCVR comprising the three heavy chain CDRs (HCDR1, HCDR2 and HCDR3) contained within the HCVR sequence selected from the group consisting of SEQ ID NO: 2, 18, 34, 50, 66, 70, 86, 90, 106, 110, 126, 130 and 146; and/or a LCVR comprising the three light chain CDRs (LCDR1, LCDR2 and LCDR3) contained within the LCVR sequences selected from the group consisting of SEQ ID NO: 10, 26, 42, 58, 68, 78, 88, 98, 108, 118, 128, 138 and 148.

In certain embodiments, the methods provided herein contemplate the use of an isolated human antibody or antigen-binding fragment thereof that binds hGCGR comprising a HCDR3 domain having an amino acid sequence selected from the group consisting of SEQ ID NO: 8, 24, 40, 56, 76, 96, 116 and 136, or a substantially similar sequence thereof having at least 90%, at least 95%, at least 98% or at least 99% sequence identity; and/or a LCDR3 domain having an amino acid sequence selected from the group consisting of SEQ ID NO: 16, 32, 48, 64, 84, 104, 124 and 144, or a substantially similar sequence thereof having at least 90%, at least 95%, at least 98% or at least 99% sequence identity.

In one embodiment, the methods provided herein contemplate use of an antibody or fragment thereof that further comprises a HCDR1 domain having an amino acid sequence selected from the group consisting of SEQ ID NO: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of LGS, TAS, AAS, ATS, and TAF, or a substantially similar sequence thereof having at least 90%, at least 95%, at least 98% or at least 99% sequence identity.

In one embodiment, the antibody or antigen-binding fragment of an antibody comprises:

(a) a HCDR3 domain having an amino acid sequence selected from the group consisting of SEQ ID NO: 8, 24, 40, 56, 76, 96, 116 and 136; and (b) a LCDR3 domain having an amino acid sequence selected from the group consisting of SEQ ID NO: 16, 32, 48, 64, 84, 104, 124 and 144.

In a related embodiment, the antibody or antigen-binding fragment of the antibody further comprises:

(c) a HCDR1 domain having an amino acid sequence selected from the group consisting of SEQ ID NO: 4, 20, 36, 52, 72, 92, 112 and 132;

(d) a HCDR2 domain having an amino acid sequence selected from the group consisting of SEQ ID NO: 6, 22, 38, 54, 74, 94, 114 and 134;

(e) a LCDR1 domain having an amino acid sequence selected from the group consisting of SEQ ID NO: 12, 28, 44, 60, 80, 100, 120 and 140; and (f) a LCDR2 domain having an amino acid sequence selected from the group consisting of LGS, TAS, AAS, ATS, and TAF.

In one embodiment, the antibody or antigen-binding fragment thereof comprises a HCVR comprising a HCDR1 domain having an amino acid sequence selected from one of SEQ ID NO: 4, 20, 36, 52, 72, 92, 112 and 132; a HCDR2 domain having an amino acid sequence selected from one of SEQ ID NO: 6, 22, 38, 54, 74, 94, 114 and 134; a HCDR3 domain having an amino acid sequence selected from one of SEQ ID NOs: 8, 24, 40, 56, 76, 96, 116 and 136; and a LCVR comprising a LCDR1 domain having an amino acid sequence selected from one of SEQ ID NO: 12, 28, 44, 60, 80, 100, 120 and 140; a LCDR2 domain having an amino acid sequence selected from one of LGS, TAS, AAS, ATS, and TAF; and a LCDR3 domain having an amino acid sequence selected from one of SEQ ID NO: 16, 32, 48, 64, 84, 104, 124 and 144.

In certain embodiments, the human antibody or antigen-binding fragment of a human antibody that binds to human GCGR comprises a HCDR3/LCDR3 amino acid sequence pair selected from the group consisting of SEQ ID NO: 8/16, 24/32, 40/48, 56/64, 76/84, 86/88, 96/104, 116/124 and 136/144. Non-limiting examples of anti-GCGR antibodies having these HCDR3/LCDR3 pairs are the antibodies designated H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P, respectively.

In one embodiment, the isolated antibody or antigen-binding fragment thereof useful according to the methods provided herein, that specifically binds to GCG and neutralizes at least one activity associated with GCG, comprises: (a) three heavy chain complementarity determining regions (HCDR1, HCDR2 and HCDR3) contained within a heavy chain variable region (HCVR) amino acid sequence selected from the group consisting of SEQ ID NOs: 150, 166, 182, 198, 214, 230, 246, 262, 278 and 294; and (b) three light chain CDRs (LCDR1, LCDR2 and LCDR3) contained within a light chain variable region (LCVR) amino acid sequence selected from the group consisting of SEQ ID NOs: 158, 174, 190, 206, 222, 238, 254, 270, 286 and 302.

In some embodiments, the isolated antibody or antigen-binding fragment thereof that specifically binds to GCG and neutralizes at least one activity associated with GCG, comprises an HCVR having an amino acid sequence selected from the group consisting of SEQ ID NOs: 150, 166, 182, 198, 214, 230, 246, 262, 278 and 294 and a LCVR having an amino acid sequence selected from the group consisting of SEQ ID NOs: 158, 174, 190, 206, 222, 238, 254, 270, 286 and 302.

In some embodiments, the isolated antibody or antigen-binding fragment thereof that specifically binds to GCG and neutralizes at least one activity associated with GCG, comprises a HCVR/LCVR amino acid sequence pair selected from the group consisting of SEQ ID NOs: 150/158; 166/174; 182/190; 198/206; 214/222; 230/238; 246/254; 262/270; 278/286 and 294/302.

In some embodiments, the HCVR/LCVR amino acid sequence pair comprises SEQ ID NOs: 166/174.

In some embodiments, the HCVR/LCVR amino acid sequence pair comprises SEQ ID NOs: 182/190.

In one embodiment, the isolated antibody or antigen-binding fragment thereof useful according to the methods provided herein, comprises:

(a) a HCDR1 domain having an amino acid sequence selected from the group consisting of SEQ ID NOs: 152, 168, 184, 200, 216, 232, 248, 264, 280, and 296;

(b) a HCDR2 domain having an amino acid sequence selected from the group consisting of SEQ ID NOs: 154, 170, 186, 202, 218, 234, 250, 266, 282, and 298;

(c) a HCDR3 domain having an amino acid sequence selected from the group consisting of SEQ ID NOs: 156, 172, 188, 204, 220, 236, 252, 268, 284, and 300;

(d) a LCDR1 domain having an amino acid sequence selected from the group consisting of SEQ ID NOs: 160, 176, 192, 208, 224, 240, 256, 272, 288, and 304;

(e) a LCDR2 domain having an amino acid sequence of WAS; and (f) a LCDR3 domain having an amino acid sequence selected from the group consisting of SEQ ID NOs: 164, 180, 196, 212, 228, 244, 260, 276, 292, and 308.

In one embodiment, the isolated antibody or antigen-binding fragment thereof useful according to the methods provided herein, comprises:

(a) a HCDR1 domain comprising the amino acid sequence of SEQ ID NO: 168;

(b) a HCDR2 domain comprising the amino acid sequence of SEQ ID NO: 170;

(c) a HCDR3 domain comprising the amino acid sequence of SEQ ID NO: 172;

(d) a LCDR1 domain comprising the amino acid sequence of SEQ ID NO: 176;

(e) a LCDR2 domain comprising the amino acid sequence of WAS; and (f) a LCDR3 domain comprising the amino acid sequence of SEQ ID NO: 180.

In one embodiment, the isolated antibody or antigen-binding fragment thereof useful according to the methods provided herein, comprises:

(a) a HCDR1 domain comprising the amino acid sequence of SEQ ID NO: 184;

(b) a HCDR2 domain comprising the amino acid sequence of SEQ ID NO: 186;

(c) a HCDR3 domain comprising the amino acid sequence of SEQ ID NO: 188;

(d) a LCDR1 domain comprising the amino acid sequence of SEQ ID NO: 192;

(e) a LCDR2 domain comprising the amino acid sequence of WAS; and (f) a LCDR3 domain comprising the amino acid sequence of SEQ ID NO: 196.

Also useful according to the methods provided herein are antibodies or antigen-binding fragments thereof that specifically bind GCG, comprising a heavy chain CDR1 (HCDR1) comprising an amino acid sequence selected from any of the HCDR1 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a heavy chain CDR2 (HCDR2) comprising an amino acid sequence selected from any of the HCDR2 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a heavy chain CDR3 (HCDR3) comprising an amino acid sequence selected from any of the HCDR3 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR1 (LCDR1) comprising an amino acid sequence selected from any of the LCDR1 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR2 (LCDR2) comprising an amino acid sequence selected from any of the LCDR2 amino acid sequences provided herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising a light chain CDR3 (LCDR3) comprising an amino acid sequence selected from any of the LCDR3 amino acid sequences listed herein or a substantially similar sequence thereof having at least 90%, at least 95%, at least 98% or at least 99% sequence identity.

Also useful according to the methods provided herein are antibodies or antigen-binding fragments thereof that specifically bind GCG, comprising an HCDR3 and an LCDR3 amino acid sequence pair (HCDR3/LCDR3) comprising any of the HCDR3 amino acid provided herein paired with any of the LCDR3 amino acid sequences provided herein. According to certain embodiments, the antibodies, or antigen-binding fragments thereof, comprise an HCDR3/LCDR3 amino acid sequence pair contained within any of the exemplary anti-GCG antibodies provided herein. In certain embodiments, the HCDR3/LCDR3 amino acid sequence pair comprises SEQ ID NOs: 172/180.

Also useful according to the methods provided herein are antibodies or antigen-binding fragments thereof that specifically bind GCG, comprising a set of six CDRs (i.e., HCDR1-HCDR2-HCDR3-LCDR1-LCDR2-LCDR3) contained within any of the exemplary anti-GCG antibodies provided herein. In certain embodiments, the HCDR1/HCDR2/HCDR3/LCDR1/LCDR2/LCDR3 amino acid sequence set comprises SEQ ID NO: 168/SEQ ID NO: 170/SEQ ID NO: 172/SEQ ID NO: 176/WAS/SEQ ID NO: 180. In certain embodiments, the HCDR1/HCDR2/HCDR3/LCDR1/

LCDR2/LCDR3 amino acid sequence set comprises SEQ ID NO: 184/SEQ ID NO: 186/SEQ ID NO: 188/SEQ ID NO: 192/WAS/SEQ ID NO: 196.

In a related embodiment, the antibodies, or antigen-binding fragments thereof that specifically bind GCG, comprise a set of six CDRs (i.e., HCDR1/HCDR2/HCDR3/LCDR1/LCDR2/LCDR3) contained within an HCVR/LCVR amino acid sequence pair as defined by any of the exemplary anti-GCG antibodies provided herein. For example, the antibodies or antigen-binding fragments thereof that specifically bind GCG, comprise the HCDR1/HCDR2/HCDR3/LCDR1/LCDR2/LCDR3 amino acid sequences set contained within an HCVR/LCVR amino acid sequence pair selected from the group consisting of: 166/174; 182/190; 198/206; 214/222; 230/238; 246/254; 262/270); 278/286 and 294/302.

Non-limiting examples of antibodies that specifically bind GCG and comprise the CDR sequences provided above, include HIH059P, H4H10223P, H4H10231P, H4H10232P, H4H10236P, H4H10237P, H4H10238P, H4H10250P, H4H10256P, and H4H10270P.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, (1991) "Sequences of Proteins of Immunological Interest," National Institutes of Health, Bethesda, Md.; Al-Lazikani et al., (1997) J. Mol. Biol. 273:927-948; and Martin et al., (1989) Proc. Natl. Acad. Sci. USA 86:9268-9272. Public databases are also available for identifying CDR sequences within an antibody.

In some embodiments, a patient having severe insulin resistance may suffer from one of the conditions or diseases selected from the following: Donohue syndrome, Rabson-Mendenhall syndrome. Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, Bardet-Biedl syndrome, and a condition or disease associated with the presence of one or more gene variants reported to cause severe insulin resistance. In some embodiments, insulin degrading protease activity is detected in the patient sera. In some embodiments, neutralizing anti-insulin antibodies or anti-insulin receptor antibodies are detected in the patient sera. In some patients, severe insulin resistance arises in the context of autoimmune destruction of adipocytes leading to lipodystrophy.

In some aspects, the gene variant associated with severe insulin resistance is selected from the following: INSR, PSMD6, ADRA2A, AGPAT2 (associated with lipodystrophy and insulin resistance), AKT2, APPL1, BBS1 (associated with Bardet-Beidl Syndrome 1), BSCL2, CIDEC, GRB10, IRS2, KLF14, LEP, LEPR, LMNA (associated with lipodystrophy), MC4R, PCNT, PIK2CA, POLD1 (associated with lipodystrophy), PPARG, PTPRD, PTRF (associated with lipodystrophy), RASGRP1, TBC1D4, and TCF7L2.

In some aspects, the composition comprising the gluca-gon/GCGR antagonist is administered to a patient in combination with at least one additional therapeutic agent. The additional therapeutic agent can be any agent that alleviates or reduces the symptoms and signs associated with severe insulin resistance. In some embodiments, at least one additional therapeutic agent is selected from the following: insulin, a biguanide, hIGF1, leptin, metraleptin, pioglitazone, vildagliptin, acarbose, alpha-glycosidase inhibitors, L-arginine, dipeptidyl-peptidase-4 inhibitors, insulin secretagogues, amylin receptor agonists, insulin sensitizers, FGF21, SGLT2 inhibitors, SGLT1 inhibitors, GLP-1 receptor agonists, GLP-1 receptor activators, a second GCG inhibitor, and a second GCGR antagonist. In some aspects, the insulin secretagogue is selected from sulfonylureas, ATP-sensitive K channel antagonists, and meglitinides. In some aspects, the insulin sensitizer is selected from thiazolidinedione and rosiglitazone. In some aspects, the additional therapeutic agent can be an agent that increases energy expenditure and/or brown fat activity, such as, for example, β3 adrenergic agonists (such as miglitol), NPR1 agonists, NPR3 antagonists, triiodothyronine, thiazolidinediones, VEGF, Irisin, meteorin-like, natriuretic peptides, orexin, norepinephrine, T4, bile acids, FGF-21, menthol, slit2-C BMP7, BMP8B, and FnIII domain-like/Tn3 scaffolds (binding molecules based on the third fibronectin type III domain of human tenascin C).

Other objects and advantages will become apparent from a review of the ensuing detailed description.

BRIEF DESCRIPTION OF THE FIGURES

In FIG. 1A, mice treated with an insulin receptor antagonist, S961, and an antibody to the GCGR, H4H1327P, (open triangles) exhibited a rise in blood glucose levels relative to blood glucose levels in mice treated with the insulin receptor antagonist and an isotype control antibody (closed squares). In FIG. 1B, treatment of mice with S961 demonstrated an increase in insulin levels over time (closed squares), even in the presence of H4H1327P (open triangles). In FIG. 1C, mice treated with H4H1327P, in the absence (open circles) or presence of S961 (open triangles), exhibited higher levels of glucagon than the isotype control treated (closed circles) or S961 treated (closed squares) mice. In FIG. 1D, mice treated with S961 and H4H1327P (open triangles) maintained beta-hydroxybutyrate levels like those of the isotype control treated (closed circles) and antibody alone control (open circles). Mice treated with the insulin receptor antagonist in the absence of the GCGR antibody exhibited higher levels of beta-hydroxybutyrate (closed squares) relative to other treatment groups. Body weights among the four treatment groups were unchanged. See FIG. 1E.

In FIG. 2B, treatment with S961 caused insulin levels to rise (closed squares), and subsequent treatment with the GCGR antibody, H4H1327P, did not lower the insulin levels (open triangles). As shown in FIG. 2C, glucagon levels were higher in mice treated with H4H1327P (open circles), and still higher in mice treated with both the antibody and S961 (open triangles). FIG. 2D shows plasma beta-hydroxybutyrate levels were elevated in response to treatment with S961 (closed squares), but within days of treatment with H4H1327P, the levels dropped to those of the untreated control and antibody alone control (open triangles). FIG. 2E shows amino acids levels were higher in mice treated with H4H1327P (open circles), and still higher in mice treated with both the antibody and S961 (open triangles). No changes in body weight were observed. See FIG. 2F.

DESCRIPTION

Figure 1A:
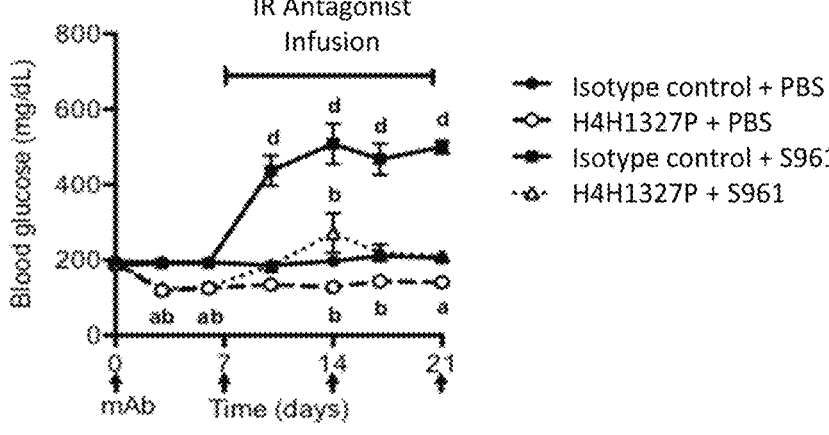
FIGS. 1A-1E show blood glucose levels, insulin levels, glucagon levels, and B-hydroxybutyrate levels, as well as body weights, in a mouse model of severe insulin resistance.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

General Description

Severe insulin resistance occurs in association with a variety of physiological and pathophysiological states. Clinical findings include hyperinsulinemia, acanthosis nigricans, ovarian hyperandrogenism, polycystic ovaries, and eventual hyperglycemia and, in rare instances, patients can develop ketoacidosis. Although there is no consensus definition for severe insulin resistance to distinguish it from the more common insulin resistance, syndromic insulin resistance has been classified as either primary insulin-signaling defects (insulin receptoropathies or partial disruption of the insulin signaling pathway) or insulin resistance secondary to adipose tissue abnormalities (severe obesity or lipodystrophy). See Semple et al., (2011), Genetic Syndromes of Severe Insulin Resistance, Endocrine Reviews, 32 (4): 498-514.

Evidence of severe insulin resistance is seen in patients who require exogenous insulin at doses of more than 100 to 200 units per day, or in patients with chronically elevated circulating levels of endogenous insulin. Moller and Flier, (1991) New England Journal of Medicine, 325:938-948. Fasting insulin levels above 50-70 µU/mL or peak (post-oral glucose tolerance testing) insulin levels above 350 µU/mL suggest severe insulin resistance. Insulin sensitivity index values below 2×104 µU/mL·min typically occur in the presence of severe insulin resistance. Patients with severe insulin resistance also exhibit a glucose disposal rate below 2 mg/kg·min. See Tritos and Mantzoros, (1998) Journal of Clinical Endocrinology and Metabolism, 83:3025-3030.

Insulin interacts with insulin receptors on the plasma membrane of target cells. The insulin receptor is a transmembrane tyrosine kinase receptor, and functions to regulate glucose homeostasis. The insulin receptor consists of two $\alpha$ subunits containing the site for insulin binding, and two $\beta$ subunits containing the tyrosine kinase domain; the subunits are connected by disulfide bridges to form a 350 kDa $\beta$-$\alpha$-$\alpha$-$\beta$ tetramer. Two isoforms of the receptor exist, an isoform with exon 11 (IR-B) and an isoform without exon 11 (IR-A), and the levels of the isoforms are expressed differently in various tissues. The IR-B isoform exhibits higher more efficient signaling activity the IR-A isoform, and the IR-B isoform is predominantly expressed in the liver, adipose tissue, and muscle tissue. The IR-A isoform is expressed in CNS cells and hematopoietic cells, and has slightly higher insulin binding affinity.

The tyrosine kinase activity of the activated insulin receptor is responsible for transmembrane signaling of glucose transport and regulation of glucose homeostasis.

Severe insulin resistance is typically associated with insulin receptor mutations, resulting in diminished expression on the cell surface or in the signaling capacity of the receptor. Other mutations include defects in receptor binding affinity or mutations in proteins involved in the insulin signal transduction pathway, e.g. the conserved regions of the tyrosine kinase domain of the insulin receptor.

Patients having severe insulin resistance may suffer from a condition or disease selected from the following: Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, or Bardet-Biedl syndrome.

Genetic and acquired states of severe insulin resistance are rare disorders in which the body's tissues and organs do not respond properly to insulin. Clinical findings associated with severe insulin resistance include growth retardation, organomegaly, impaired development of skeletal and adipose tissue, soft tissue overgrowth, diabetes, hepatic steatosis, acanthosis nigricans, ovarian hyperandrogenism, and hirsutism. Laboratory findings include hyperinsulinemia, reduced insulin clearance, hyperglycemia, dyslipidemia, and elevated androgens. Each of the various syndromes associated with severe insulin resistance have unique features, in addition to some or all of the general clinical and laboratory features.

Donohue syndrome (DS, also called Leprechaunism) and Rabson-Mendenhall syndrome (RMS) are rare autosomal recessive conditions in which both alleles for the insulin receptor are abnormal, and patients fail to respond to endogenous and exogenous insulin. Individuals with DS and RMS are underdeveloped before birth, then fail to thrive as infants. Patients present with extremely high levels of circulating insulin, up to 1000 times the normal level. The primary metabolic consequence of DS is fasting hypoglycemia, and secondarily, post-prandial hyperglycemia. Individuals diagnosed with DS usually die before one year of age and do not develop diabetic ketoacidosis. Individuals with RMS also experience fasting hypoglycemia and typically survive infancy, but over time, develop severe and intractable diabetic ketoacidosis and a decline in insulin levels.

Ketonemia occurs when ketone bodies are formed by the breakdown of fatty acids and the deamination of amino acids and accumulate in the blood. If this continues untreated, the patients can then continue on to diabetic ketoacidosis. Beta-hydroxybutyrate and acetoacetic acid are two of the more common ketones, and elevated levels can be used to gauge the severity of ketonemia and an indicator of ketoacidosis.

Type A insulin resistance syndrome is another rare disorder characterized by severe insulin resistance, and symptoms typically present in adolescence for females, or adulthood for males. Females present with primary amenorrhea or oligomenorrhea, ovarian cysts, hirsutism, and acanthosis nigricans, but are typically not overweight. Affected males present when they develop diabetes mellitus. As with DS and RMS, insulin receptor gene mutations are responsible for Type A insulin resistance syndrome.

Lipodystrophy refers to a group of disorders characterized by abnormal adipose distribution, utilization, and metabolism, due to defects in the insulin receptor itself or downstream components of the insulin signaling cascade. Patients with lipodystrophy present with a generalized or partial absence of adipose tissue, insulin resistance (with or without diabetes), significant dyslipidemia, and fatty liver. Some lipodystrophy syndromes, like Berardinelli-Seip syndrome, are inherited, while others, including Lawrence syndrome, are acquired, sometimes after an infectious prodrome. Additional lipodystrophy syndromes include Kobberling-Dunnigan syndrome, lipodystrophy with other dysmorphic features, and cephalothoracic lipodystrophy.

Type B insulin resistance syndrome is different from DS, RMS, and Type A insulin resistance syndrome in that the former is associated with the presence of serum auto-antibodies against the insulin receptor, and may occur in the context of an autoimmune disease. Symptoms are similar to other insulin resistance syndromes, and include non-ketotic and severely insulin-resistant diabetes, acanthosis nigricans, and hirsutism, in addition to occasional paradoxal hypoglycemia.

HAIR-AN (hyperandrogenism, insulin resistance, and acanthosis nigricans) syndrome presents in young women, typically obese, with insulin resistance taking different forms; some individuals have high concentrations of insulin but normal levels of glucose, while others present with diabetic symptoms. Unlike the rarity of other syndromes of severe insulin resistance, HAIR-AN syndrome is estimated to affect around 5% of adolescent girls worldwide. The syndrome is associated with mutations of the tyrosine kinase domain of the insulin receptor gene.

Pseudoacromegaly presents with severe insulin resistance in association with acromegaloidism, and is possibly caused by a defect in the insulin signaling pathway or from high insulin levels signaling through the IGF-1 receptor.

Other severe insulin resistance syndromes include Alstrom syndrome, myotonic dystrophy, and Werner's syndrome, to name a few.

In some patients, the condition or disease is associated with the presence of a gene variant reported to cause severe insulin resistance. Exemplary gene variants include INSR, PSMD6, ADRA2A, AGPAT2 (associated with lipodystrophy and insulin resistance), AKT2, APPL1, BBS1 (associated with Bardet-Beidl Syndrome 1), BSCL2, CIDEC, GRB10, IRS2, KLF14, LEP, LEPR, LMNA (associated with lipodystrophy), MC4R, PCNT, PIK2CA, POLD1 (associated with lipodystrophy), PPARG, PTPRD, PTRF (associated with lipodystrophy), RASGRP1, TBC1D4, and TCF7L2.

In some patients, insulin degrading protease activity is detected in the patient sera. In some patients, neutralizing anti-insulin antibodies or anti-insulin receptor antibodies are detected in the patient sera. In some patients, severe insulin resistance arises in the context of autoimmune destruction of adipocytes leading to lipodystrophy.

Patients with severe insulin resistance eventually develop hyperglycemia and, in some syndromes, ketoacidosis. For example, in patients with RMS, insulin levels start out very high early in life, even during periods of paradoxical fasting hypoglycemia. As the disease progresses, insulin levels while still elevated, drop. In addition, partially oxidized fatty acid levels increase, indicating that insulin is unable to suppress the release of fatty acids from adipocytes, ultimately resulting in constant ketoacidosis. Likewise, constant hyperglycemia results as insulin levels are no longer capable of suppressing hepatic glucose production and release. However, continuous infusion of extremely high concentrations of insulin (9.5 U/kg hr) can reverse increased fatty acid oxidation and block ketonuria. Longo et al., (1991) Journal of Clinical Endocrinology & Metabolism, 84:2623-2629. In addition, hypertriglyceridemia and low high-density lipoprotein cholesterol levels are associated with severe insulin resistance.

Patients with severe insulin resistance syndromes have normal or even slightly elevated plasma glucagon levels despite hyperglycemia. West et al., (1975) Arch. Dis. Child., 50(9):703-708; Desbois-Mouthon et al., (1997) Pediatr. Res., 42(1):72-77. The hyperglycemia results from enhanced hepatic glucose output due to lack of insulin suppression and abnormally high glucagon signaling.

To date, there have been no studies examining the effects of antagonizing the GCG/GCGR signaling pathway on severe insulin resistance conditions or diseases. The studies described in the Examples use an antagonist of GCGR, as an exemplary inhibitor of the GCG/GCGR signaling pathway, in a mouse model of severe insulin resistance to demonstrate the effects on blood glucose levels and ketonemia, as measured by plasma beta-hydroxybutyrate levels, over several weeks of treatment.

Definitions

The "glucagon receptor", also referred to herein as "GCGR", belongs to the G protein-coupled receptor class 2 family and consists of a long amino terminal extracellular domain, seven transmembrane segments, and an intracellular C-terminal domain. Glucagon receptors are notably expressed on the surface of hepatocytes where they bind to glucagon and transduce the signal provided thereby into the cell. Accordingly, the term "glucagon receptor" also refers to one or more receptors that interact specifically with glucagon to result in a biological signal. DNA sequences encoding glucagon receptors of rat and human origin have been isolated and disclosed in the art (EP0658200B1). The murine and cynomolgus monkey homologues have also been isolated and sequenced (Burcelin, et al., (1995) Gene 164:305-310); McNally et al., (2004) Peptides 25:1171-1178). As used herein, "glucagon receptor" and "GCGR" are used interchangeably. The expression "GCGR", "hGCGR" or fragments thereof, as used herein, refers to the human GCGR protein or fragment thereof, unless specified as being from a non-human species, e.g. "mouse GCGR", "rat GCGR", or "monkey GCGR".

The phrase "GCGR antagonist" refers to an inhibitor, antagonist, or inverse agonist of the GCGR signaling pathway. A "GCG inhibitor" may prevent the binding of glucagon to the receptor. A GCGR inhibitor may also prevent the binding of glucagon to the receptor. However, both effectively block or attenuate activation of the receptor, or may interfere with the signaling cascade downstream of the GCGR activation.

A GCGR antagonist is able to bind to the glucagon receptor and thereby antagonize the activity of GCG mediated by the GCGR. Inhibiting the activity of GCG by antagonizing the binding and activity of GCG at the GCGR reduces the rate of gluconeogenesis and glycogenolysis, and the concentration of glucose in plasma. Methods by which to determine the binding of a supposed antagonist with the glucagon receptor are known in the art and means by which to determine the interference with glucagon activity at the glucagon receptor are publicly available; see, e.g., S. E. de Laszlo et al., (1999) Bioorg. Med. Chem. Lett. 9:641-646. Contemplated as useful herein are GCGR antagonists or GCG inhibitors having as a functional component thereof a small molecule compound, or in other words a low molecular weight organic compound. A small molecule is typically less than 800 Daltons. Additionally, CRISPR technology can be used to knock-down GCG or GCGR expression.

The terms "inhibitor" or "antagonist" include a substance that retards or prevents a chemical or physiological reaction or response. Common inhibitors or antagonists include but are not limited to antisense molecules, antibodies, small molecule inhibitors, peptide inhibitors, DARPins, Spiegelmers, aptamers, engineered Fn type-III domains, and their derivatives.

An example of a GCG inhibitor or a GCGR signaling pathway antagonist includes, but is not limited to, an antibody (human or humanized), or an antigen binding portion thereof, to GCG or GCGR, that blocks binding or inhibits the activity of the GCGR signaling pathway. Exemplary GCGR antagonists that may be used in the methods described herein include isolated human monoclonal antibody or antigen-binding fragment thereof comprising: (a) a HCVR having an amino acid sequence selected from the group consisting of SEQ ID NO: 2, 18, 34, 50, 66, 70, 86, 90, 106, 110, 126, 130) and 146; and/or (b) a LCVR having an amino acid sequence selected from the group consisting of SEQ ID NO: 10, 26, 42, 58, 68, 78, 88, 98, 108, 118, 128, 138 and 148. Exemplary GCG inhibitors that may be used in the methods described herein include isolated human monoclonal antibody or antigen-binding fragment thereof comprising: (a) a HCVR having an amino acid sequence selected from the group consisting of SEQ ID NO: 150, 166, 182, 198, 214, 230, 246, 262, 278, and 294; and/or (b) a LCVR having an amino acid sequence selected from the group consisting of SEQ ID NO: 158, 174, 190, 206, 222, 238, 254, 270, 286, and 302.

A "therapeutically effective dose" is a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the phrase "substantially identical" is meant a protein sequence having at least 95% identity to an HCVR having an amino acid sequence selected from the group consisting of SEQ ID NO: 2, 18, 34, 50, 66, 70, 86, 90, 106, 110, 126, 130 and 146; and/or (b) a LCVR having an amino acid sequence selected from the group consisting of SEQ ID NO: 10, 26, 42, 58, 68, 78, 88, 98, 108, 118, 128, 138 and 148, and capable of binding GCGR and inhibiting the biological activity of GCGR. The phrase "substantially identical" is also meant a protein sequence having at least 95% identify to an HCVR having an amino acid sequence selected from the group consisting of the amino acid sequences SEQ ID NO: 150, 166, 182, 198, 214, 230, 246, 262, 278, and 294; and/or (b) a LCVR having an amino acid sequence selected from the group consisting of SEQ ID NO: 158, 174, 190, 206, 222, 238, 254, 270, 286, and 302, and capable of binding GCG and inhibiting the biological activity of GCG.

The terms "identity" or "homology" are construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710) University Ave., Madison, Wis. 53705). This software matches similar sequences by assigning degrees of homology to various substitutions, deletions, and other modifications.

The term "treating" (or "treat" or "treatment") refers to processes involving a slowing, interrupting, inhibiting, arresting, controlling, stopping, reducing, ameliorating, or reversing the progression, duration, or severity of an existing symptom, disorder, condition, or disease, but does not necessarily involve a total elimination of all disease-related symptoms, conditions, or disorders through use of a GCG inhibitor or GCGR antagonist as described herein. Furthermore, "treating", "treatment" or "treat" refers to an approach for obtaining beneficial or desired results including clinical results, which include, but are not limited to, one or more of the following: inhibiting, delaying or preventing the progression of severe insulin resistance; inhibiting, delaying or preventing the progression of a disease associated with severe insulin resistance, or characterized by elevated plasma insulin levels, elevated blood glucose levels, and/or ketonemia or ketoacidosis (as measured by elevated beta-hydroxybutyrate levels), such as in Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, Bardet-Biedl syndrome, or a condition or disease associated with the presence of a gene variant reported to cause severe insulin resistance; or inhibiting, preventing, or ameliorating at least one symptom associated with a disease associated with severe insulin resistance; or lowering blood glucose levels and/or beta-hydroxybutyrate levels (as an indicator of ketoacidosis), such that the condition or disease associated with high blood glucose levels and ketonemia is mediated, or at least one symptom or complication associated with the condition or disease is alleviated or reduced in severity. "Treatment" or "treating", as used herein, also refers to increasing the quality of life of those suffering from the disease, decreasing the dose of other medications required to treat the disease and/or prolonging survival of patients. For example, "treatment" or "treating" can include reducing the amount and/or dosage of insulin necessary to treat a patient with severe insulin resistance.

The phrase "insulin resistance" is a state in which a greater than normal amount of insulin is required to elicit a quantitatively normal response. The phrase "severe insulin resistance" generally refers to a clinical entity that typically presents with near-normal or elevated blood glucose levels despite marked elevations in endogenous insulin secretion and/or plasma levels of insulin. Evidence of severe insulin resistance is seen in patients who require exogenous insulin at doses of more than 100 to 200 units per day, or in patients with chronically elevated circulating levels of endogenous insulin. Moller and Flier, (1991) New England Journal of Medicine, 325:938-948. Fasting insulin levels above 50-70 µU/mL or peak (post-oral glucose tolerance testing) insulin levels above 350 µU/mL suggest severe insulin resistance. Insulin sensitivity index values below $2 \times 10^4$ µU/mL min typically occur in the presence of severe insulin resistance. Patients with severe insulin resistance also exhibit a glucose disposal rate below 2 mg/kg min. See Tritos and Mantzoros, (1998) Journal of Clinical Endocrinology and Metabolism, 83:3025-3030.

GCG/GCGR Signaling Pathway Inhibitors

Provided herein are GCG inhibitors and GCGR antagonists for the treatment of conditions or diseases characterized by severe insulin resistance. In some embodiments, the antagonist is an inhibitor of glucagon. In some embodiments, the antagonist is an inhibitor of GCGR. In some embodiments, the GCGR antagonist is MK-0893, PF-06291874, LGD-6972, or LY2409021.

In some embodiments, the antagonist comprises an antibody capable of binding GCG or GCGR, or a fragment thereof. In some embodiments, the signaling pathway is inhibited by the interruption of GCG or GCGR expression, by, for example, using CRISPR technology or antisense.

In some embodiments, the GCG inhibitor or GCGR antagonist is an antisense molecule, antibody, small molecule inhibitor, peptide inhibitor, DARPin, Spiegelmer, aptamer, engineered Fn type-III domains, or a derivative thereof.

Anti-GCGR Antibodies, Anti-GCG Antibodies, and Antibody Fragments

In some embodiments, the GCGR antagonist is an antibody or antibody fragment as disclosed in U.S. Pat. No. 8,545,847, incorporated by reference herein in its entirety. Antibodies disclosed therein are provided in Table 1.

TABLE 1

| Antibody | SEQ ID NOS: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H4H1345N | 2 | 4 | 6 | 8 | 10 | 12 | LGS | 16 |
| H4H1617N | 18 | 20 | 22 | 24 | 26 | 28 | LGS | 32 |
| H4H1765N | 34 | 36 | 38 | 40 | 42 | 44 | LGS | 48 |
| H4H1321B | 50 | 52 | 54 | 56 | 58 | 60 | TAS | 64 |
| H4H1321P | 66 | 52 | 54 | 56 | 68 | 60 | TAS | 64 |
| H4H1327B | 70 | 72 | 74 | 76 | 78 | 80 | AAS | 84 |
| H4H1327P | 86 | 72 | 74 | 76 | 88 | 80 | AAS | 84 |
| H4H1328B | 90 | 92 | 94 | 96 | 98 | 100 | ATS | 104 |
| H4H1328P | 106 | 92 | 94 | 96 | 108 | 100 | ATS | 104 |
| H4H1331B | 110 | 112 | 114 | 116 | 118 | 120 | AAS | 124 |
| H4H1331P | 126 | 112 | 114 | 116 | 128 | 120 | AAS | 124 |
| H4H1339B | 130 | 132 | 134 | 136 | 138 | 140 | TAF | 144 |
| H4H1339P | 146 | 132 | 134 | 136 | 148 | 140 | TAF | 144 |

Additional GCGR antibodies or antibody fragments contemplated as useful herein include those disclosed in U.S. Pat. Nos. 5,770,445 and 7,947,809; European patent application EP2074149A2; EP patent EP0658200B1; U.S. patent publications 2009/0041784; 2009/0252727; and 2011/0223160; and PCT publication WO2008/036341. The patents and publications are incorporated by reference herein in their entirety.

In some embodiments, the GCG inhibitor is an antibody or antibody fragment thereof as disclosed in U.S. 2016/0075778, incorporated by reference herein in its entirety. Antibodies disclosed therein are provided in Table 2.

the light ($V_L$) chains of immunoglobulins. Or by immunizing people and isolating antigen positive B cells and cloning the cDNAs encoding the heavy and light chain and coexpressing them in a cell, such as CHO.

The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu,

TABLE 2

| Antibody | SEQ ID NOS: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1H059P | 150 | 152 | 154 | 156 | 158 | 160 | WAS | 164 |
| H4H10223P | 166 | 168 | 170 | 172 | 174 | 176 | WAS | 180 |
| H4H10231P | 182 | 184 | 186 | 188 | 190 | 192 | WAS | 196 |
| H4H10232P | 198 | 200 | 202 | 204 | 206 | 208 | WAS | 212 |
| H4H10236P | 214 | 216 | 218 | 220 | 222 | 224 | WAS | 228 |
| H4H10237P | 230 | 232 | 234 | 236 | 238 | 240 | WAS | 244 |
| H4H10238P | 246 | 248 | 250 | 252 | 254 | 256 | WAS | 260 |
| H4H10250P | 262 | 264 | 266 | 268 | 270 | 272 | WAS | 276 |
| H4H10256P | 278 | 280 | 282 | 284 | 286 | 288 | WAS | 292 |
| H4H10270P | 294 | 296 | 298 | 300 | 302 | 304 | WAS | 308 |

Additional GCG antibodies or antibody fragments contemplated as useful herein include those disclosed in U.S. Pat. Nos. 4,206,199; 4,221,777; 4,423,034; 4,272,433; 4,407,965; 5,712,105; and PCT publications WO2007/124463 and WO2013/081993.

Antibody fragments include any fragment having the required target specificity, e.g. antibody fragments either produced by the modification of whole antibodies (e.g. enzymatic digestion), or those synthesized de novo using recombinant DNA methodologies (scFv, single domain antibodies, DVD (dual variable domain immunoglobulins), or dAbs (single variable domain antibodies)) or those identified using human phage or yeast display libraries (see, for example, McCafferty et al. (1990) Nature 348:552-554). Alternatively, antibodies can be isolated from mice producing human, human-mouse, human-rat, and human-rabbit chimeric antibodies using standard immunization and antibody isolation methods, including but not limited to making hybridomas, or using B cell screening technologies, such as SLAM. Immunoglobulin binding domains also include, but are not limited to, the variable regions of the heavy ($V_H$) or alpha, delta, or epsilon, which in turn define the immunoglobulin classes, IgG, IgM, IgA, IgD, and IgE, respectively. Within each IgG class, there are different isotypes (eg. IgG1, IgG2, IgG3, IgG4). Typically, the antigen-binding region of an antibody will be the most critical in determining specificity and affinity of binding.

An exemplary immunoglobulin (antibody) structural unit comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology.

Methods for preparing antibodies useful according to the methods herein are known to the art. See, for example, Kohler & Milstein (1975) Nature 256:495-497; Harlow & Lane (1988) Antibodies: a Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Monoclonal antibodies can be humanized using standard cloning of the CDR regions into a human scaffold. Gene libraries encoding human heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946, 778; 4,816,567) can be adapted to produce antibodies used in the methods disclosed herein. Also, transgenic mice, or other organisms such as other mammals, may be used to express human, human-mouse chimeric, human-rat chimeric, human-rabbit chimeric, or humanized antibodies. Alternatively, phage display or yeast display technology can be used to identify human antibodies and heteromeric Fab fragments that specifically bind to selected antigens.

Immunoconjugates

The disclosure encompasses treatment of severe insulin resistance with a human anti-GCGR monoclonal antibody conjugated to a therapeutic moiety ("immunoconjugate"), such as an agent that is capable of reducing blood glucose levels or addressing another symptom of severe insulin resistance. The type of therapeutic moiety that may be conjugated to the anti-GCGR antibody will take into account the condition to be treated and the desired therapeutic effect to be achieved. For example, in an effort to lower blood glucose, and/or to maintain normal blood glucose levels, an agent such as biguanide (e.g. metformin), a sulfonylurea (e.g. glyburide, glipizide), a PPAR gamma agonist (e.g. pioglitazone, rosiglitazone); an alpha glucosidase inhibitor (e.g. acarbose, voglibose), an inhibitor of advanced glycation end-product formation (e.g. aminoguanidine), or a second GCGR inhibitor or GCG inhibitor may be conjugated to the GCGR antibody. Alternatively, if the desired therapeutic effect is to treat ketonemia or any other symptoms or conditions associated with severe insulin resistance, it may be advantageous to conjugate an appropriate agent to the anti-GCGR antibody. Examples of suitable agents for forming immunoconjugates are known in the art, see for example, WO 05/103081.

Multi-Specific Antibodies

The antibodies useful according to the methods provided herein may be mono-specific, bi-specific, or multi-specific. Multi-specific antibodies may be specific for different epitopes of one target polypeptide or may contain antigen-binding domains specific for more than one target polypeptide. See, e.g., Tutt et al., (1991) J. Immunol. 147:60-69; Kufer et al., (2004) Trends Biotechnol. 22:238-244. The anti-GCGR antibodies can be linked to or co-expressed with another functional molecule, e.g., another peptide or protein.

For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, bi-specific antibodies are contemplated where one arm of an immunoglobulin is specific for human GCGR or a fragment thereof, and the other arm of the immunoglobulin is specific for a second therapeutic target or is conjugated to a therapeutic moiety. In certain embodiments, one arm of an immunoglobulin is specific for an epitope on the N-terminal domain of hGCGR or a fragment thereof, and the other arm of the immunoglobulin is specific for an epitope on one of the EC loops of hGCGR, or a fragment thereof. In certain embodiments, one arm of an immunoglobulin is specific for one EC loop, or a fragment thereof, and the second arm is specific for a second EC loop, or a fragment thereof. In certain embodiments, one arm of an immunoglobulin is specific for one epitope on one EC loop of hGCGR and the other arm is specific for a second epitope on the same EC loop of hGCGR.

An exemplary bi-specific antibody format that can be used according to the methods described herein involves the use of a first immunoglobulin (Ig) C$_H$3 domain and a second Ig C$_H$3 domain, wherein the first and second Ig C$_H$3 domains differ from one another by at least one amino acid, and wherein at least one amino acid difference reduces binding of the bi-specific antibody to Protein A as compared to a bi-specific antibody lacking the amino acid difference. In one embodiment, the first Ig C$_H$3 domain binds Protein A and the second Ig C$_H$3 domain contains a mutation that reduces or abolishes Protein A binding such as an H95R modification (by IMGT exon numbering; H435R by EU numbering). The second C$_H$3 may further comprise a Y96F modification (by IMGT; Y436F by EU). Further modifications that may be found within the second C$_H$3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Antibody Screening and Selection

Screening and selection of preferred antibodies, useful according to the methods provided herein, can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of antibody-drug conjugates. Secondary screening may be conducted with any suitable method known to the art. One preferred method, termed "Biosensor Modification-Assisted Profiling" ("BiaMAP") is described in U.S. Publication 2004/0101920, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody: antigen interactions. Antibodies capable of blocking either a ligand or a receptor may be identified by a cell based assay, such as a luciferase assay utilizing a luciferase gene under the control of an NFκB driven promoter or cAMP response driven promoter. Stimulation of the GCGR by glucagon leads to a signal through NFκB/cAMP/CREB thus increasing luciferase levels in the cell. Blocking antibodies are identified as those antibodies that blocked glucagon induction of luciferase activity.

Treatment Population

The therapeutic methods provided herein are useful for treating individuals with severe insulin resistance or a condition or disease associated with severe insulin resistance. Exemplary conditions or diseases include Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, Bardet-Biedl syndrome, and a condition or disease associated with the presence of a gene variant reported to cause severe insulin resistance. In some embodiments, insulin degrading protease activity is detected in the patient sera. In some embodiments, neutralizing anti-insulin antibodies are detected in the patient sera. In some patients, severe insulin resistance arises in the context of autoimmune destruction of adipocytes leading to lipodystrophy.

Therapeutic Administration and Formulations

Useful according to the methods provided herein are therapeutic compositions comprising a glucagon/GCGR antagonist, such as, for example, an anti-GCGR antibody. The administration of therapeutic compositions in accordance with the methods described herein will be administered via a suitable route including, but not limited to, intravenously, subcutaneously, intramuscularly, intrathecally, intracerebrally, intraventricularly, intranasally, or orally, with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody is used for lowering blood glucose levels and/or decreasing ketonemia (as measured by, for example, beta-hydroxybutyrate levels) associated with severe insulin resistance in various conditions and diseases, such as Type A insulin resistance syndrome, RMS, or DS, in a patient, it is advantageous to intravenously administer the antibody normally at a dose of about 0.01 to about 30 mg/kg body weight, more preferably about 0.02 to about 7, about 0.03 to about 5, or about 0.05 to about 3 mg/kg body weight. Depending on the severity of the condition and response to treatment, the frequency and the duration of the treatment can be adjusted. In certain embodiments, the antibody or antigen-binding fragment thereof can be administered as an initial dose of at least about 0.1 mg to about 800 mg, about 1 to about 500 mg, about 5 to about 300 mg, or about 10 to about 200 mg, to about 100 mg, or to about 50 mg.

In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition comprising the antibody, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, depot formulations, aerosol, intradermal, transdermal, intramuscular, intraperitoneal, intravenous, subcutaneous, intranasal, epidural, intrathecal, intraventricular, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990)) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50) mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition useful herein can be delivered subcutaneously or intravenously with a standard needle and syringe. In addition, with respect to subcutaneous delivery, a pen delivery device readily has applications in delivering a pharmaceutical composition useful in the methods described herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition useful according to the methods described herein. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Inn.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition useful according to the methods described herein include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 750 mg per dosage form in a unit dose; especially in the form of injection, it is preferred that the aforesaid antibody is contained in about 5 to about 100 mg and in about 10 to about 250 mg for the other dosage forms.

Combination Therapies

In numerous embodiments, the GCG inhibitors or GCGR antagonists useful herein may be administered in combination with one or more additional compounds or therapies. Combination therapy may be simultaneous or sequential.

In some embodiments, the GCG inhibitor or GCGR antagonist is administered with at least one additional therapeutic agent selected from the following: insulin, a biguanide, hIGF1, leptin, pioglitazone, vildagliptin, acarbose, alpha-glycosidase inhibitors, L-arginine, dipeptidyl-peptidase-4 inhibitors, insulin secretagogues, amylin receptor agonists, insulin sensitizers, SGLT2 inhibitors, SGLT1 inhibitors, GLP-1 analogues, GLP-1 receptor activators, a second GCG inhibitor, and a second GCGR antagonist. In some embodiments, the GCG inhibitor or GCGR antagonist is administered with at least one additional therapeutic agent selected from the following: vanadate or vanadium salts, phenytoin, benzafibrate. In some embodiments, the GCG inhibitor or GCGR antagonist is administered with a dietary supplement such as @-3 fatty acid rich fish oil.

In some embodiments, the insulin sensitizer is a thiazolidinedione, such as troglitazone. In some embodiments, the insulin sensitizer is rosiglitazone.

In some embodiments, the insulin secretagogue is a sulfonylurea, ATP-sensitive K channel antagonists, or a meglitinide.

The additional therapeutically active component(s) may be administered prior to, concurrent with, or after the administration of the GCG inhibitor or the GCGR antagonist. For purposes of the present disclosure, such administration regimens are considered the administration of a GCG inhibitor or a GCGR antagonist "in combination with" a second therapeutically active component.

Administration Regimens

According to certain embodiments described herein, multiple doses of the glucagon/GCGR antagonist may be administered to a subject over a defined time course. The methods comprise sequentially administering to a subject multiple doses of a glucagon/GCGR antagonist. As used herein, "sequentially administering" means that each dose of the antagonist is administered to the subject at a different point in time, e.g., on different days separated by a predetermined interval (e.g., hours, days, weeks or months). The methods described herein comprise sequentially administering to the patient a single initial dose of the glucagon/GCGR antagonist, followed by one or more secondary doses of the glucagon/GCGR antagonist, and optionally followed by one or more tertiary doses of the glucagon/GCGR antagonist.

The terms "initial dose," "secondary doses," and "tertiary doses," refer to the temporal sequence of administration of an glucagon/GCGR antagonist useful herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the glucagon/GCGR antagonist, but generally may differ from one another in terms of frequency of administration. In certain embodiments, however, the amount of the glucagon/GCGR antagonists contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Pharmaceutical Compositions

The methods disclosed herein contemplate the use of pharmaceutical compositions comprising at least a therapeutically effective amount of an active agent useful in treating severe insulin resistance, such as a glucagon/GCGR antagonist, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In one embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents useful according to the methods described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent which will be effective in the treatment of severe insulin resistance can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20 micrograms to 2 grams of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration.

One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

Also provided herein is an article of manufacturing comprising packaging material and a pharmaceutical agent contained within the packaging material, wherein the pharmaceutical agent comprises at least one GCG/GCGR antagonist useful according to the methods disclosed herein, and wherein the packaging material comprises a label or package insert which indicates that the GCG/GCGR antagonist can be used for treating a condition or disease characterized by severe insulin resistance.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided such that those of ordinary skill in the art have a complete disclosure and description of how to implement the methods disclosed herein. Efforts have been made to ensure accuracy with respect to numbers used (e.g., amounts, temperature, etc.) but some experimental errors and deviations should be accounted for. Unless indicated otherwise, parts are by weight, molecular weight is average molecular weight, temperature is in degrees Centigrade, and pressure is at or near atmospheric.

Example 1: Evaluation of a GCGR Antagonist in Preventing Hyperglycemia in a Mouse Model of Extreme Insulin Resistance Administration of S961, an insulin receptor antagonist, by osmotic minipumps in mice causes severe insulin resistance and hyperglycemia (Gusarova V et al., (2014) Cell, 159: 691-696; Yi P et al., (2013) Cell, 153:747-758; Schaffer L., (2008) Biochem. Biophys. Res. Commun., 376:380-383). This model of severe insulin resistance was used to determine the effect of an anti-GCGR antibody in preventing hyperglycemia, as well as the effects on blood glucose levels and plasma beta-hydroxybutyrate levels (as a measure of ketonemia), resulting from severe insulin resistance.

Materials:
hIgG4 isotype control
H4H1327P, anti-hGCGR hIgG4
S961, insulin receptor antagonist (custom synthesized by Celtek Peptides using published sequence (Schaffer L., (2008) Biochem. Biophys. Res. Commun., 376:380-383))

Animals and Injections:
Twenty-nine mice were divided into four groups of six to eight mice. The first group was injected subcutaneously with 10 mg/kg of hIgG4 isotype control on Day 0, 6, and 14 and infused subcutaneously with PBS by osmotic minipumps (Alzet 2002) from Day 7. The second group was injected subcutaneously with 10 mg/kg of H4H1327P on Day 0, 6, and 14 and infused subcutaneously with PBS by osmotic minipumps (Alzet 2002) from Day 7. The third group was injected subcutaneously with 10 mg/kg of hIgG4 isotype control on Day 0, 6, and 14 and infused subcutaneously with S961 at 20 nmol/week by osmotic minipumps (Alzet 2002) from Day 7. The fourth group was injected subcutaneously with 10 mg/kg of H4H1327P on Day 0, 6, and 14 and infused subcutaneously with S961 at 20 nmol/week by osmotic minipumps (Alzet 2002) from Day 7. Mice were bled on Days 0, 3, 6, 10, 14, 17, and 21 for blood glucose measurements. Mean±SEM of blood glucose levels at each time point was calculated for each group and shown in Table 3. Plasma was collected at baseline and Days 6, 14, and 21 to determine insulin and beta-hydroxybutyrate levels. Mean±SEM of plasma beta-hydroxybutyrate and insulin levels at each time point was calculated for each group and shown in Tables 4 and 5.

TABLE 3

| | | Blood glucose levels | | | |
|---|---|---|---|---|---|
| | Time (days) | Isotype control + PBS | H4H1327P + PBS | Isotype control + S961 | H4H1327P + S961 |
| Blood | 0 | 196 ± 6 | 191 ± 4 | 186 ± 5 | 196 ± 3 |
| Glucose | 3 | 195 ± 7 | 119 ± 3 | 191 ± 6 | 124 ± 6 |
| (mg/dL) | 6 | 194 ± 9 | 126 ± 4 | 192 ± 5 | 129 ± 12 |
| | 10 | 186 ± 4 | 135 ± 2 | 437 ± 40 | 185 ± 7 |
| | 14 | 197 ± 5 | 128 ± 4 | 508 ± 53 | 272 ± 53 |
| | 17 | 211 ± 6 | 144 ± 3 | 467 ± 41 | 219 ± 22 |
| | 21 | 206 ± 5 | 141 ± 5 | 499 ± 18 | 209 ± 6 |

TABLE 4

| | | Plasma beta-hydroxybutyrate levels | | | |
|---|---|---|---|---|---|
| | Time (days) | Isotype control + PBS | H4H1327P + PBS | Isotype control + S961 | H4H1327P + S961 |
| Beta- | 0 | 0.20 ± 0.02 | 0.20 ± 0.02 | 0.21 ± 0.02 | 0.24 ± 0.02 |
| hydroxy | 6 | 0.26 ± 0.01 | 0.24 ± 0.01 | 0.26 ± 0.01 | 0.27 ± 0.01 |
| butyrate | 14 | 0.22 ± 0.02 | 0.23 ± 0.02 | 0.34 ± 0.04 | 0.26 ± 0.03 |
| (mg/dL) | 21 | 0.23 ± 0.01 | 0.23 ± 0.02 | 0.34 ± 0.04 | 0.25 ± 0.03 |

TABLE 5

| | | Plasma insulin levels | | | |
|---|---|---|---|---|---|
| | Time (days) | Isotype control + PBS | H4H1327P + PBS | Isotype control + S961 | H4H1327P + S961 |
| Insulin | 0 | 0.80 ± 0.14 | 1.90 ± 0.69 | 1.15 ± 0.68 | 1.62 ± 0.67 |
| (ng/mL) | 6 | 0.24 ± 0.04 | 0.24 ± 0.06 | 0.21 ± 0.10 | 0.24 ± 0.04 |
| | 14 | 0.37 ± 0.09 | 0.36 ± 0.05 | 22.83 ± 4.32 | 18.51 ± 2.30 |
| | 21 | 0.40 ± 0.13 | 0.46 ± 0.15 | 23.97 ± 4.36 | 25.11 ± 5.15 |

Results:

Statistical analysis was performed with Prism software (version 6). To assess the significance to the control group (Group 1), two-way ANOVA with Bonferroni multiple comparison test was used. a: $p<0.05$, b: $p<0.01$, c: $p<0.001$, d: $p<0.0001$.

H4H1327P-treated and PBS-infused animals (Group 2) showed reductions in blood glucose compared to isotype control-administered and PBS-infused animals (Group 1) post H4H1327P administration (between days 3 and 21), confirming glucose lowering efficacy of H4H1327P. Isotype control-administered and S961-infused animals (Group 3) showed increases in blood glucose compared to isotype control-administered and PBS-infused animals (Group 1) post infusion of S961 (between days 10 and 21), confirming hyperglycemic effect of S961. In H4H1327P-treated and S961-infused animals (Group 4), blood glucose levels were comparable to those of Group 1 mice between 10 and 21 days post S961 infusion. See FIG. 1A.

Figure 1B:
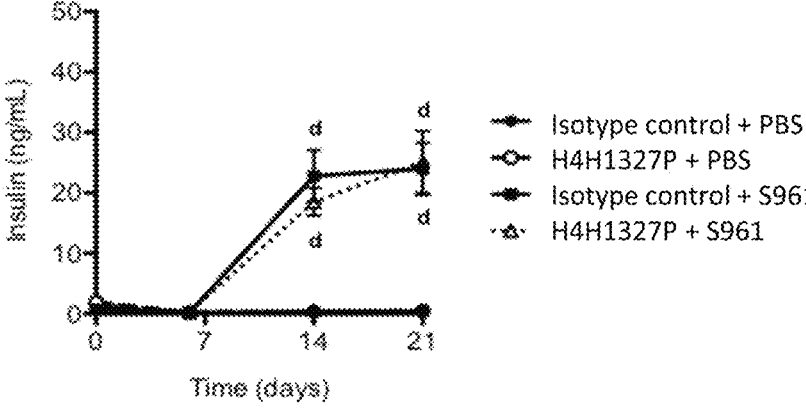

Plasma insulin levels were elevated in isotype control-administered and S961-infused animals (Group 3) compared to isotype control-administered and PBS-infused animals (Group 1) on Days 14 and 21, confirming the action of S961 to inhibit insulin receptor during the duration of the study. The insulin levels were equally increased in H4H1327P-treated and S961-infused animals (Group 4) in comparison to isotype control-administered and S961-infused animals (Group 3). See FIG. 1B.

Figure 1C:
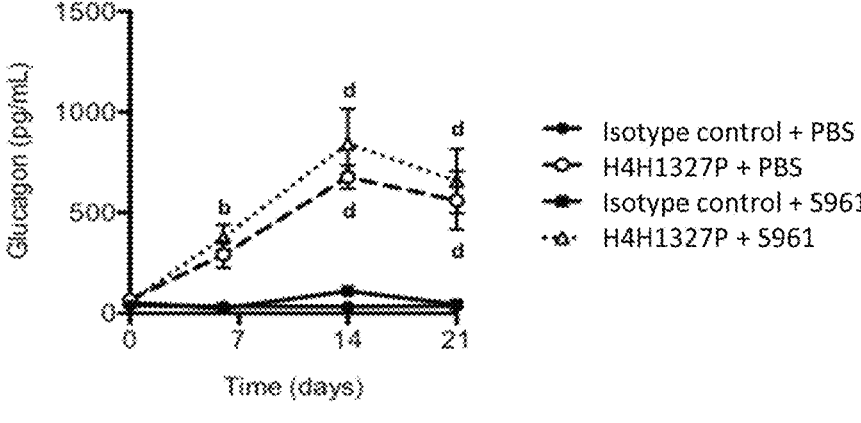

Consistent with previous studies (Okamoto et al., (2015) Endocrinology, 156 (8): 2781-2794), H4H1327P demonstrated increased plasma glucagon levels, an effect that was independent of S961 administration (See FIG. 1C).

Figure 1D:
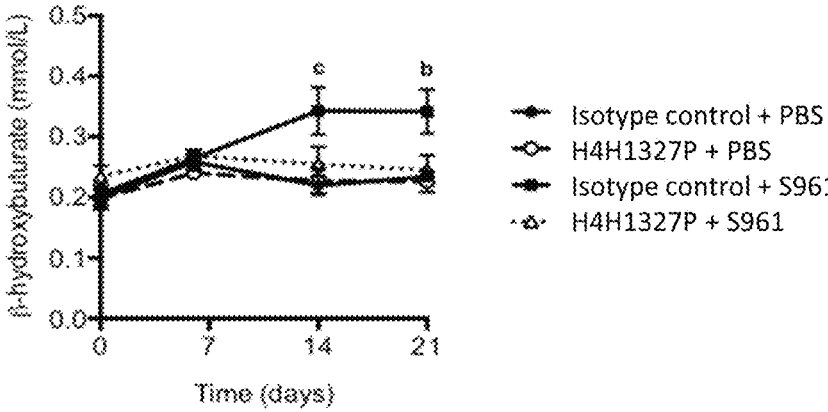
Figure 1E:
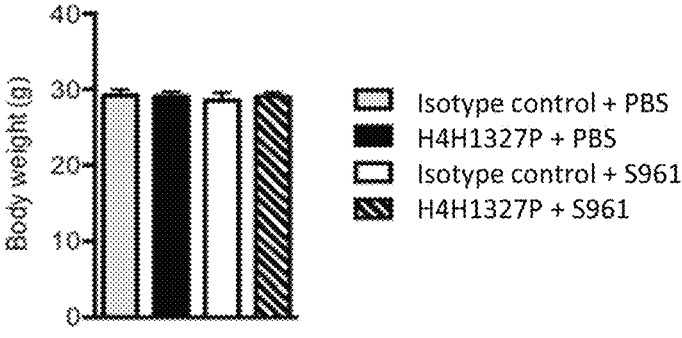

The levels of plasma beta-hydroxybutyrate were elevated in isotype control-administered and S961-infused animals (Group 3) compared to isotype control-administered and PBS-infused animals (Group 1) on Day 14 and 21, whereas they were not changed in H4H1327P-treated and S961-infused animals (Group 4). See FIG. 1D. In addition, no differences in body weight were observed between the treatment groups (See FIG. 1E).

These data indicate that H4H1327P prevents insulin receptor antagonist-induced hyperglycemia and ketonemia and lowers blood glucose even in the presence of severe hyperinsulinemia.

Example 2: Evaluation of a GCGR Antagonist in Reversing Hyperglycemia in a Mouse Model of Extreme Insulin Resistance The effect of an anti-GCGR antibody in reversing established hyperglycemia induced by severe insulin resistance was determined using the same animal model and the same materials mentioned in Example 1, except that the insulin receptor antagonist was administered 4 days prior to injection of the anti-GCGR antibody. The effects on blood glucose and plasma beta-hydroxybutyrate levels were also determined.

Animals and Injections:

Thirty-two mice were divided into four groups of eight mice. The first group was infused subcutaneously with PBS by osmotic minipumps (Alzet 2002) from Day 0 and injected subcutaneously with 10 mg/kg of hIgG4 isotype control on Day 4, 11 and 18. The second group was infused subcutaneously with PBS from Day 0 and injected subcutaneously with 10 mg/kg of H4H1327P on Day 4, 11 and 18. The third group was infused subcutaneously with S961 at 20 nmol/week from Day 0 and injected subcutaneously with 10 mg/kg of hIgG4 isotype control on Day 4, 11 and 18. The fourth group was infused subcutaneously with S961 at 20 nmol/week from Day 0 and injected subcutaneously with 10 mg/kg of H4H1327P on Day 4, 11 and 18. Mice were bled on Days 0, 4, 7, 11, 14, 18 and 21 for blood glucose measurements. Mean±SEM of blood glucose levels at each time point was calculated for each group and shown in Table 6. Plasma was collected at baseline and Days 4, 11, and 21 to determine insulin and beta-hydroxybutyrate levels. Mean±SEM of plasma beta-hydroxybutyrate and insulin levels at each time point was calculated for each group and shown in Tables 7 and 8.

TABLE 6

| | Blood glucose levels (mg/dL) | | | |
|---|---|---|---|---|
| Time (days) | PBS + isotype control | PBS + H4H1327P | S961 ± isotype control | S961 + H4H1327P |
| 0 | 186 ± 4 | 189 ± 4 | 192 ± 4 | 183 ± 4 |
| 4 | 196 ± 3 | 197 ± 3 | 491 ± 29 | 490 ± 21 |
| 7 | 216 ± 5 | 142 ± 6 | 523 ± 34 | 203 ± 6 |
| 11 | 206 ± 6 | 137 ± 4 | 533 ± 14 | 201 ± 6 |
| 14 | 210 ± 7 | 145 ± 5 | 595 ± 6 | 211 ± 9 |
| 18 | 202 ± 7 | 140 ± 4 | 550 ± 16 | 203 ± 5 |
| 21 | 168 ± 6 | 123 ± 4 | 526 ± 12 | 172 ± 5 |

TABLE 7

| | Plasma beta-hydroxybutyrate levels (mmol/L) | | | |
|---|---|---|---|---|
| Time (days) | PBS + isotype control | PBS + H4H1327P | S961 ± isotype control | S961 + H4H1327P |
| 0 | 0.20 ± 0.01 | 0.22 ± 0.01 | 0.21 ± 0.02 | 0.18 ± 0.02 |
| 4 | 0.27 ± 0.01 | 0.25 ± 0.02 | 0.41 ± 0.02 | 0.37 ± 0.04 |
| 11 | 0.26 ± 0.02 | 0.24 ± 0.01 | 0.39 ± 0.03 | 0.26 ± 0.02 |
| 21 | 0.26 ± 0.01 | 0.25 ± 0.01 | 0.45 ± 0.06 | 0.26 ± 0.02 |

TABLE 8

| | Plasma insulin levels (ng/mL) | | | |
|---|---|---|---|---|
| Time (days) | PBS + isotype control | PBS + H4H1327P | S961 ± isotype control | S961 + H4H1327P |
| 0 | 1.05 ± 0.31 | 0.77 ± 0.25 | 0.52 ± 0.08 | 0.42 ± 0.09 |
| 4 | 0.62 ± 0.32 | 0.50 ± 0.11 | 19.23 ± 3.18 | 21.68 ± 2.02 |
| 11 | 0.39 ± 0.09 | 0.35 ± 0.05 | 25.97 ± 3.48 | 64.25 ± 18.17 |
| 21 | 1.67 ± 0.47 | 0.37 ± 0.04 | 51.43 ± 15.03 | 64.78 ± 14.91 |

Results:

Statistical analysis was performed with Prism software (version 6). To assess the significance to the control group (Group1), two-way ANOVA with Bonferroni multiple comparison test was used. a: $p<0.05$, b: $p<0.01$, c: $p<0.001$, d: $p<0.0001$.

Figures 2A, 2B:
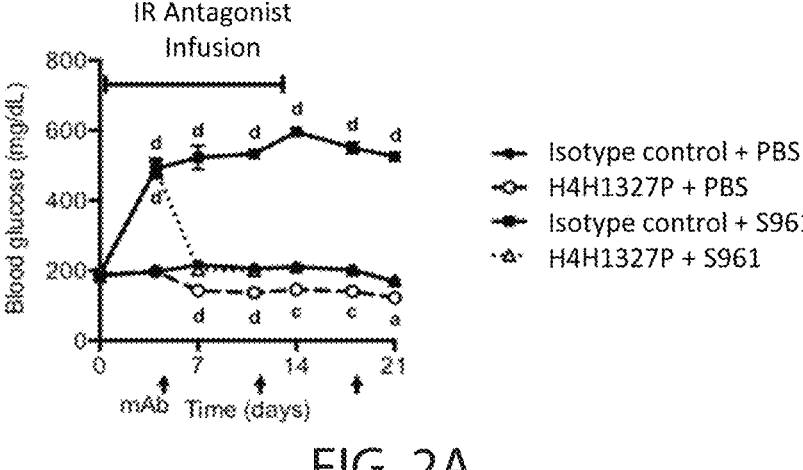
FIGS. 2A-2F show blood glucose levels, insulin levels, glucagon levels, B-hydroxybutyrate levels, and amino acid levels, as well as body weights, in a mouse model of severe insulin resistance. The insulin receptor antagonist (S961) treatment preceded the antibody treatment, H4H1327P, causing increased blood glucose levels, and the ability of the antibody to decrease blood glucose levels was demonstrated within days of initiating antibody treatment (open triangles). See FIG. 2A.

S961-infused and isotype control-administered animals (Group 3) showed increases in blood glucose compared to PBS-infused and isotype control-administered animals (Group 1) post S961 infusion (between days 4 and 21), confirming hyperglycemic effect of S961. S961-infused and H4H1327P-treated animals (Group 4) showed blood glucose levels that were nearly identical to those of PBS-infused and isotype control-administered and animals (Group 1) post H4H1327P administration. PBS-infused and H4H1327P-treated animals (Group 2) maintained reduced levels of blood glucose compared to isotype control-administered and PBS-infused animals (Group 1) post H4H1327P administration (between days 4 and 21), confirming glucose lowering efficacy of H4H1327P. See FIG. 2A.

Plasma insulin levels were elevated in S961-infused and isotype control-administered animals (Group 3) compared to PBS-infused and isotype control-administered animals (Group 1) on Days 4, 11 and 21, confirming the action of S961 to inhibit insulin receptor during the duration of the study. See FIG. 2B. The hyperinsulinemia (Table 8 and FIG.

Figure 2C:
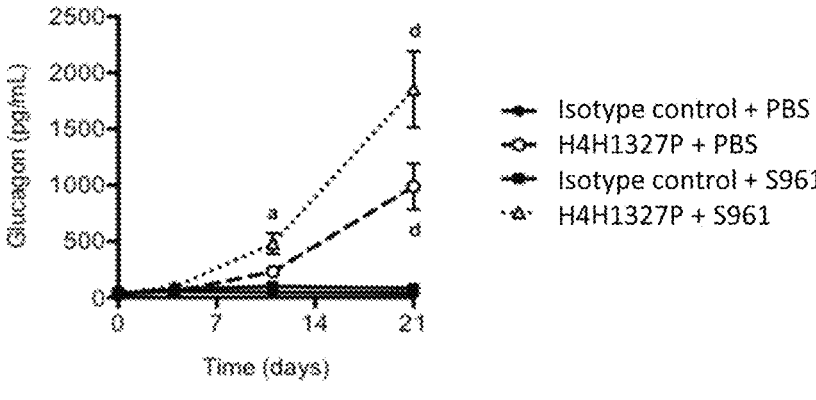

2B) and hyperglucagonemia (see FIG. 2C) was more pronounced in mice that received both receptor antagonists.

Figure 2D:
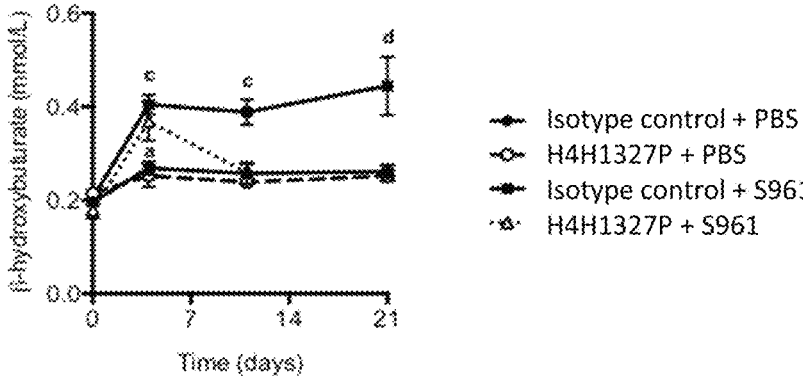

The levels of plasma beta-hydroxybutyrate were elevated in S961-infused and isotype control-administered animals (Group 3) compared to PBS-infused and isotype control-administered animals (Group 1) on Days 11 and 21, whereas they were not changed in S961-infused and H4H1327P-treated animals (Group 4) at these same time points relative to Group 1 animals. See FIG. 2D.

Figure 2E:
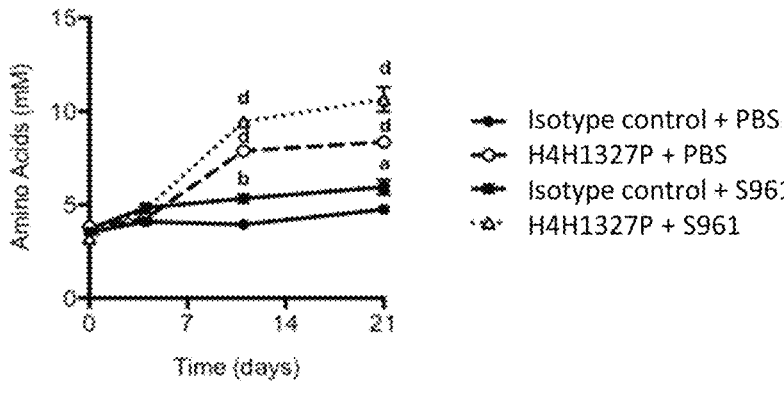
Figure 2F:
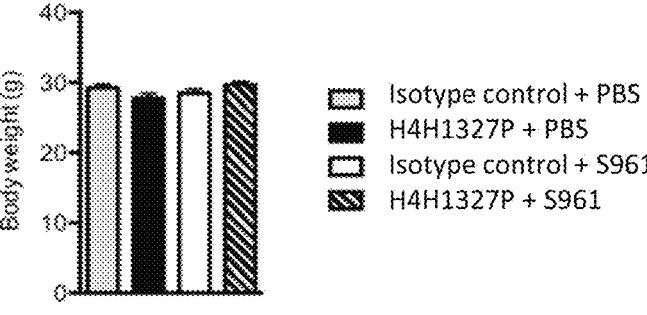

Consistent with previous findings (Okamoto et al., 2015), H4H1327P increased circulating amino acid levels, as did S961 but to a lesser extent than did the antibody (see FIG. 2E). Inhibition of both insulin and glucagon receptors caused an additive increase in plasma amino acid levels (see FIG. 2E). No changes in body weight were observed (see FIG. 2F).

These data indicate that H4H1327P reverses insulin receptor antagonist-induced hyperglycemia and ketonemia and lowers blood glucose even in the presence of severe hyperinsulinemia.

Example 3: Evaluation of a GCGR Antagonist in Reversing Insulin Receptor Antagonist-Induced Liver Pepck Expression Liver samples obtained from mice treated according to each of the four groups from Example 1 were lysed with ice-cold RIPA buffer (50 mM Tris, 150 mM NaCl, 1 mM of EDTA, 50 mM NaF, 10 mM β-glycerophosphate, 5 mM sodium pyrophosphate dibasic and 1% NP-40) in the presence of protease and phosphatase inhibitor cocktails (Thermo-Fisher), 1 mM DTT and 2 mM $Na_3VO_4$. Total sample lysates were mixed with 6×SDS loading buffer (Alfa-Aesar) and boiled for 5 min. Protein samples (10-100 μg) were loaded and separated on 4-20% gradient SDS-PAGE gels (Bio-Rad) and transferred to polyvinylidene difluoride membranes. The membranes were blocked for 1 h with 5% bovine serum albumin in 1×TBS supplemented with 0.1% Tween20) (Bio-Rad) and incubated with antibody against phosphoenolpyruvate carboxykinase (PEPCK) (1:250); Abcam). Bound antibodies were detected using horseradish peroxidase-conjugated anti-rabbit or anti-mouse secondary antibodies (1:10,000; Jackson ImmunoResearch) and enhanced chemiluminescence reagent (Thermo-Fisher). Band intensities were quantified in Image J software.

Figure 3A:
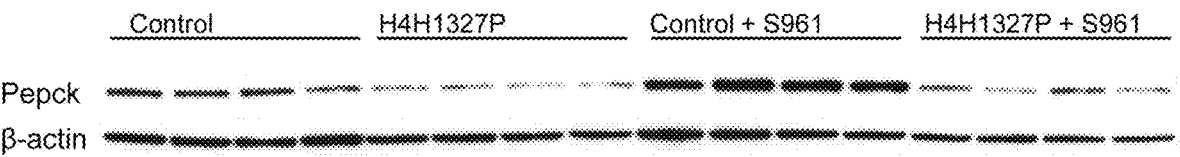
FIGS. 3A and 3B provide the results of Western blot analysis on mice liver samples obtained from mice treated with one or both of S961 and H4H1327P. Treatment with H4H1327P reduced phosphoenolpyruvate carboxykinase (Pepck) in mice livers by 70% relative to the isotype treated control group, and treatment with S961 caused a 2.3 fold increase in Pepck levels. Treatment with H4H1327P reversed the increased levels caused by S961 to 30% below baseline. See FIGS. 3A and 3B.
Figure 3B:
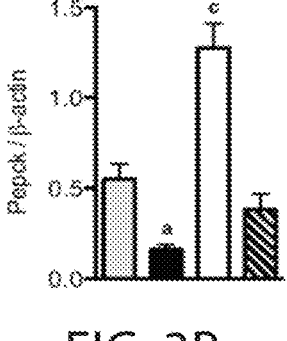

Western blot analysis revealed that levels of the rate limiting gluconeogenic enzyme phosphoenolpyruvate carboxykinase (Pepck) were reduced by 70% in livers of mice treated with H4H1327P (see FIGS. 3A and B). On the contrary, Pepck levels increased 2.3-fold in livers of mice infused with S961, an effect that was reversed to 30% below baseline by H4H1327P. Thus, the relative levels of glucagon and insulin signaling regulate Pepck expression, as demonstrated previously (Lynedjian et al., (1995); Rucktäschel et al., (2000); Chakravarty et al., (2005)). These data show that GCGR blockade with H4H1327P prevents severe insulin resistance-induced hyperglycemia in mice by suppressing hepatic glucose output.

Example 4: Evaluation of GCGR and Insulin Receptor Antagonism in α- and β-Cell Masses The pancreas obtained from mice treated according to each of the four groups from Example 2 were fixed in 10% neutral buffered formalin solution for 48 h, embedded in paraffin, and sectioned onto slides. Pancreatic tissue and cells were permeabilized and hybridized with combinations of mRNA probes for mouse Gcg and Ins2 according to the manufacturer's instructions (Advanced Cell Diagnostics). A chromagenic kit was used to amplify mRNA signal (Advanced Cell Diagnostics). Areas of glucagon and insulin positive cells were measured using Halo digital imaging analysis software (Indica Labs). The percent of glucagon and insulin positive areas in proportion to the whole pancreas area were calculated. α- and β-cell mass was calculated by multiplying the α- and β-cell area for each animal against their corresponding pancreas weight. Islet number was measured by counting the number of insulin positive islets on a section with the use of Halo digital imaging analysis software and normalized by the entire pancreas area of the section.

Figure 4A:
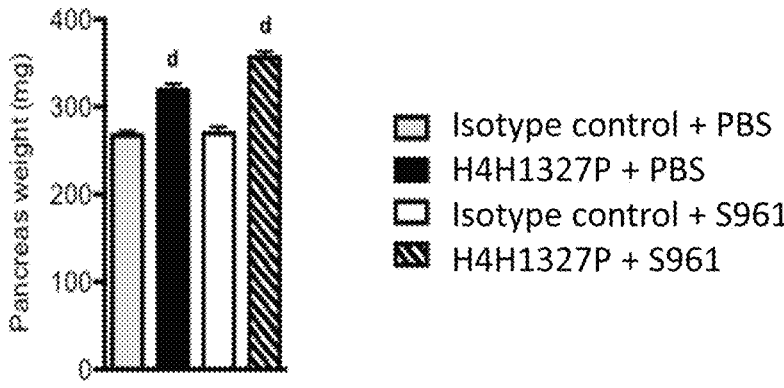
FIGS. 4A-4D show the effects of the four treatments on pancreatic tissue: pancreas weight, FIG. 4A; pancreas α-cell mass, FIG. 4B; pancreas β-cell mass, FIG. 4C; and islet numbers relative to total pancreas area, FIG. 4D. B-cell mass doubled in the presence of S961 and H4H1327P when compared to S961 alone and increased 5.8-fold over control mice. See FIG. 4C.
Figure 4B:
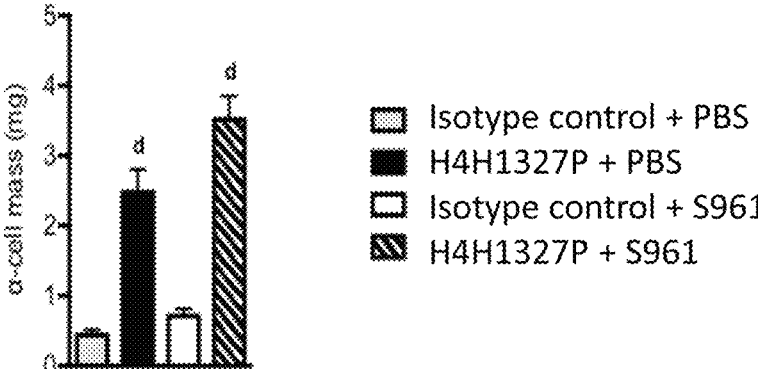
Figure 4C:
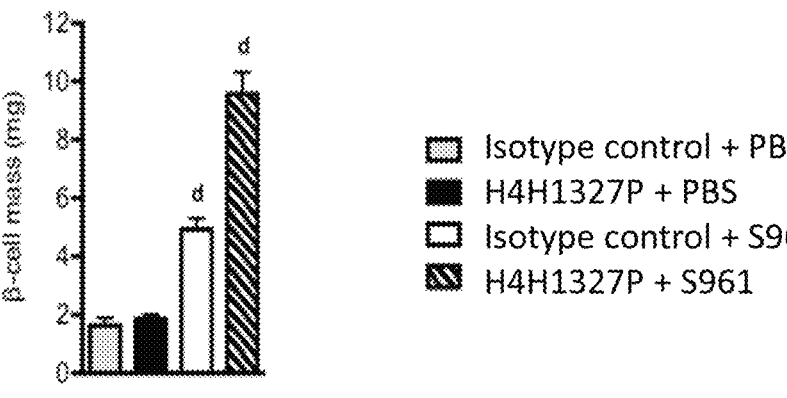
Figure 4D:
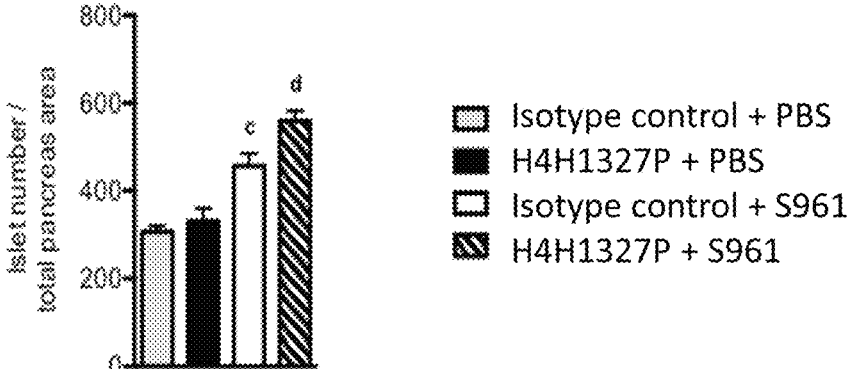

H4H1327P increased pancreas weight by 19%, an effect that was larger (33%) in the presence of both H4H1327P and S961 (see FIG. 4A). RNA in situ hybridization (RNA ISH) using probes to Gcg and Ins2 was used for morphometric analysis of pancreatic sections. H4H1327P increased α-cell mass 5.7-fold (see FIG. 4B), and S961 administration increased β-cell mass 3-fold (see FIG. 4C). H4H1327P alone did not affect β-cell mass, but unexpectedly, β-cell mass doubled in the simultaneous presence of S961 and H4H1327P when compared to S961 alone and increased 5.8-fold over control mice (see FIG. 4C). It is important to note that the further expansion of the β-cell mass took place in settings of normal blood glucose levels (Table 3). α-cell mass was slightly increased by S961 treatment (1.6-fold) and in the simultaneous presence of H4H1327P (1.4-fold over H4H1327P alone) (see FIG. 4B). S961 increased islet number per total pancreas area by 49%, whereas the combined treatment with S961 and H4H1327P increased islet number per area by 82% (see FIG. 4D)). In summary. compensatory increases in α- and β-cell masses were produced when glucagon and insulin signaling were inhibited. The novel finding is that β-cell mass doubled in insulin resistant mice when glucagon signaling was blocked and that this effect took place at normal blood glucose levels.

TABLE 9

| Informal Sequence Listing | | |
|---|---|---|
| SEQ ID NO. | | Description |
| 1. | caggtccagttggtacagtctggggctgacgtgaagaagcctggg gcctcagtgaaggtctcctgcaaggtttccggacatatcctcact gatttatccatgcactgggtgcgacagcctcctggaaaaggactt gagtggatggcaggttttgatcctgaagaaggtaaaataatctac gcacagaagttccagggcagagtcaccatgaccgaggacacatct acagacacagcctacatggagctgagcagcctgagatctggggac acggccgtttattactgtgcaacaagcgatattttgactgggtat tatagagactactacggtttggacgtctggggccaagggaccacg ctcaccgtctcctca | nucleotide sequence |
| 2. | QVQLVQSGADVKKPGASVKVSCKVSGHILTDLSMHWVRQPPGKGL EWMAGFDPEEGKIIYAQKFQGRVTMTEDTSTDTAYMELSSLRSGD TAVYYCATSDILTGYYRDYYGLDVWGQGTTLTVSS | amino acid sequence |
| 3. | ggacatatcctcactgatttatcc | nucleotide sequence |
| 4. | GHILTDLS | amino acid sequence |
| 5. | tttgatcctgaagaaggtaaaata | nucleotide sequence |
| 6. | FDPEEGKI | amino acid sequence |
| 7. | gcaacaagcgatattttgactgggtattatagagactactacggt ttggacgtc | nucleotide sequence |
| 8. | ATSDILTGYYRDYYGLDV | amino acid sequence |
| 9. | gatattgtgatgactcagtctccactcttcctgcccgtcacccct ggagagccggcctccatctcctgcaggtctagtcagagcctcctg catagtaaaggatacaactatttggattggtacctgcagaagcca gggcagtctccacaactcctgatctatttgggttctaatcgggcc tccggggtccctgacaggttcagtggcagtggatcaggcacagat tttacactgaaaatcagcagagtggaggctgaagatgttggggtt tattactgcatgcaaactctacaaactcctcggacgttcggccaa gggaccaaggtggaaatcaaa | nucleotide sequence |
| 10. | DIVMTQSPLFLPVTPGEPASISCRSSQSLLHSKGYNYLDWYLQKP GQSPQLLIYLGSNRASGVPDRESGSGSGTDFTLKISRVEAEDVGV YYCMQTLQTPRTFGQGTKVEIK | amino acid sequence |

TABLE 9-continued

Informal Sequence Listing

| SEQ ID NO. | | Description |
|---|---|---|
| 11. | cagagcctcctgcatagtaaaggatacaactat | nucleotide sequence |
| 12. | QSLLHSKGYNY | amino acid sequence |
| 13. | ttgggttct | nucleotide sequence |
| 14. | LGS | amino acid sequence |
| 15. | atgcaaactctacaaactcctcggacg | nucleotide sequence |
| 16. | MQTLQTPRT | amino acid sequence |
| 17. | caggtccagttggtacagtctggggctgacgtgaagaagcctggg gcctcagtgaaggtctcctgcaaggtttccggacatatcctcact gatttatccatgcactgggtgcgacaggctcctggaaaagggctt gagtggatgggaggttttgatcctgaagaaggtgaaataatctac gcacagaagttccagggcagagtcaccatgaccgaggacacatct acagacacagcctacatggagctgagcagcctgagatctggggac acggccgtttattactgtgcaacaagcgatattttgactggttat tatagagactactacggtttggacgtctggggccaagggaccacg ctcaccgtctcctca | nucleotide sequence |
| 18. | QVQLVQSGADVKKPGASVKVSCKVSGHILTDLSMHWVRQAPGKGL EWMGGFDPEEGEIIYAQKFQGRVTMTEDTSTDTAYMELSSLRSGD TAVYYCATSDILTGYYRDYYGLDVWGQGTTLTVSS | amino acid sequence |
| 19. | ggacatatcctcactgatttatcc | nucleotide sequence |
| 20. | GHILTDLS | amino acid sequence |
| 21. | tttgatcctgaagaaggtgaaata | nucleotide sequence |
| 22. | FDPEEGEI | amino acid sequence |
| 23. | gcaacaagcgatattttgactggttattatagagactactacggt ttggacgtc | nucleotide sequence |
| 24. | ATSDILTGYYRDYYGLDV | amino acid sequence |
| 25. | gatattgtgatgactcagtctccactcttcctgcccgtcacccct ggagagccggcctccatctcctgcaggtctagtcagagcctcctg catagtaaaggatacaactatttggattggtacctgcagaagcca gggcagtctccacaactcctgatctatttgggttctaatcgggcc tccggggtccctgacaggttcagtggcagtggatcaggcacagat tttacactgaaaatcagcagagtggaggctgaagatgttgggggtt tattactgcatgcaaactctacaaactcctcggacgttcggccaa gggaccaaggtggaaatcaaa | nucleotide sequence |
| 26. | DIVMTQSPLFLPVTPGEPASISCRSSQSLLHSKGYNYLDWYLQKP GQSPQLLIYLGSNRASGVPDRFSGSGSGTDFTLKISRVEAEDVGV YYCMQTLQTPRTFGQGTKVEIK | amino acid sequence |
| 27. | cagagcctcctgcatagtaaaggatacaactat | nucleotide sequence |

TABLE 9-continued

Informal Sequence Listing

| SEQ ID NO. | | Description |
|---|---|---|
| 28. | QSLLHSKGYNY | amino acid sequence |
| 29. | ttgggttct | nucleotide sequence |
| 30. | LGS | amino acid sequence |
| 31. | atgcaaactctacaaactcctcggacg | nucleotide sequence |
| 32. | MQTLQTPRT | amino acid sequence |
| 33. | gaggagcaactggtggagtctgggggagacttggtacagcctgga gggtccctaagactctcctgtgcagcctctggattcactctcagt agttatgaaatgaactgggtccgccaggctccagggaaggggctg gagtgggtttcatacattagtagaggtggtagtctgatacactac acagactctgtgaagggccgattcaccatctccagagacaacgcc aagaattcactgtatctgcaaatgaacagcctgagagccgaggac acggctgtttattactgtgtgagagacccagcagctcgttatcat tattattatcacggtatggacgtctggggccaagggaccacggtc accgtctcctca | nucleotide sequence |
| 34. | EEQLVESGGDLVQPGGSLRLSCAASGFTLSSYEMNWVRQAPGKGL EWVSYISRGGSLIHYTDSVKGRFTISRDNAKNSLYLQMNSLRAED TAVYYCVRDPAARYHYYYHGMDVWGQGTTVTVSS | amino acid sequence |
| 35. | ggattcactctcagtagttatgaa | nucleotide sequence |
| 36. | GFTLSSYE | amino acid sequence |
| 37. | attagtagaggtggtagtctgata | nucleotide sequence |
| 38. | ISRGGSLI | amino acid sequence |
| 39. | gtgagagacccagcagctcgttatcattattattatcacggtatg gacgtc | nucleotide sequence |
| 40. | VRDPAARYHYYYHGMDV | amino acid sequence |
| 41. | gatattgtgatgactcagtctccactctccctgcccgtcacccct ggagagccggcctccatctcctgcaggtctagtcagagcctcctg cacaataatggatataactatttggattggtatctgcagaagcca gggcagtctccacagctcctgatctatttgggttctagtcgggcc tccggggtccctgacaggttcagtggcagtggatcaggcacagat tttatactgaaaatcagcagagtggaggctgaagatgttggggtt tattactgcatgcaagctctacaaactccgtggacgttcggccga gggaccaaggtggaaatcaaa | nucleotide sequence |
| 42. | DIVMTQSPLSLPVTPGEPASISCRSSQSLLHNNGYNYLDWYLQKP GQSPQLLIYLGSSRASGVPDRFSGSGSGTDFILKISRVEAEDVGV YYCMQALQTPWTFGRGTKVEIK | amino acid sequence |
| 43. | cagagcctcctgcacaataatggatataactat | nucleotide sequence |
| 44. | QSLLHNNGYNY | amino acid sequence |

TABLE 9-continued

Informal Sequence Listing

| SEQ ID NO. | | Description |
|---|---|---|
| 45. | ttgggttct | nucleotide sequence |
| 46. | LGS | amino acid sequence |
| 47. | atgcaagctctacaaactccgtggacg | nucleotide sequence |
| 48. | MQALQTPWT | amino acid sequence |
| 49. | gaggtgcagctggtggagtctgggggaggcgtggtccagcctggg aggtccctgagactctcctgtgcagcctctggattcaccttcagt agttatgacatgcactgggtccgccaggctccaggcaaggggctg gagtgggtggcagttatatcatctgatggacgtgataaatactat gtagactccgtgaagggccgattcaccatctccagagacaactcc aagaacacgctttatctgcaaatgaacagcctgagagctgaggac acggctgtttattactgtgcgaaagagatggtgtattacgatatt ttgactggttatcataactactacggtatggacgtctggggccaa gggaccacggtcaccgtctcctca | nucleotide sequence |
| 50. | EVOLVESGGGVVQPGRSLRLSCAASGFTFSSYDMHWVRQAPGKGL EWVAVISSDGRDKYYVDSVKGRFTISRDNSKNTLYLQMNSLRAED TAVYYCAKEMVYYDILTGYHNYYGMDVWGQGTTVTVSS | amino acid sequence |
| 51. | ggattcaccttcagtagttatgac | nucleotide sequence |
| 52. | GFTFSSYD | amino acid sequence |
| 53. | atatcatctgatggacgtgataaa | nucleotide sequence |
| 54. | ISSDGRDK | amino acid sequence |
| 55. | gcgaaagagatggtgtattacgatattttgactggttatcataac tactacggtatggacgtc | nucleotide sequence |
| 56. | AKEMVYYDILTGYHNYYGMDV | amino acid sequence |
| 57. | gacatcgtgatgacccagtctccatcctcactgtctgcatctgta ggagacagagtcaccatcacttgtcgggcgagtcagggcattaac aattatttagcctggtttcagcagaaaccagggaaagcccctaag tccctgatccatactgcatccagtttgcaaagtggggtcccatca aagttcagcggcagtggatctgggacagatttcactctcaccatc agcagcctgcagcctgaagattttgcaacttattactgccaacag tataatacttaccctctcactttcggcggagggaccaaagtggag atcaaacga | nucleotide sequence |
| 58. | DIVMTQSPSSLSASVGDRVTITCRASQGINNYLAWFQQKPGKAPK SLIHTASSLQSGVPSKFSGSGSGTDFTLTISSLQPEDFATYYCQQ YNTYPLTFGGGTKVEIKR | amino acid sequence |
| 59. | cagggcattaacaattat | nucleotide sequence |
| 60. | QGINNY | amino acid sequence |
| 61. | actgcatcc | nucleotide sequence |

TABLE 9-continued

| SEQ ID NO. | | Description |
|---|---|---|
| 62. | TAS | amino acid sequence |
| 63. | caacagtataatacttaccctctcact | nucleotide sequence |
| 64. | QQYNTYPLT | amino acid sequence |
| 65. | caggtgcagctggtggagtctggggggaggcgtggtccagcctggg aggtccctgagactctcctgtgcagcctctggattcaccttcagt agttatgacatgcactgggtccgccaggctccaggcaaggggctg gagtgggtggcagttatatcatctgatggacgtgataaatactat gtagactccgtgaagggccgattcaccatctccagagacaactcc aagaacacgctttatctgcaaatgaacagcctgagagctgaggac acggctgtttattactgtgcgaaagagatggtgtattacgatatt ttgactggttatcataactacggtatggacgtctggggccaa gggaccacggtcaccgtctcc | nucleotide sequence |
| 66. | QVQLVESGGGVVQPGRSLRLSCAASGFTFSSYDMHWVRQAPGKGL EWVAVISSDGRDKYYVDSVKGRFTISRDNSKNTLYLQMNSLRAED TAVYYCAKEMVYYDILTGYHNYYGMDVWGQGTTVTVS | amino acid sequence |
| 67. | gacatccagatgacccagtctccatcctcactgtctgcatctgta ggagacagagtcaccatcacttgtcgggcgagtcagggcattaac aattatttagcctggtttcagcagaaaccagggaaagcccctaag tccctgatccatactgcatccagtttgcaaagtggggtcccatca agttcagcggcagtggatctgggacagatttcactctcaccatc agcagcctgcagcctgaagattttgcaacttattactgccaacag tataatacttaccctctcactttcggcggagggaccaaggtggag atcaaa | nucleotide sequence |
| 68. | DIQMTQSPSSLSASVGDRVTITCRASQGINNYLAWFQQKPGKAPK SLIHTASSLQSGVPSKFSGSGSGTDFTLTISSLQPEDFATYYCQQ YNTYPLTFGGGTKVEIK | amino acid sequence |
| 69. | caggtgcagctggtgcagtctggggggaggcttggtccagcctggg gggtccctgagactctcctgtgcagcctccggattcacctttagt aactatttgatgaactgggtccgccaggctccagggaaggggctg gagtggctggccaacatacaggaagatggaattgagaaatactat gtggactctgtgaagggccgattcaccatctccagagacaacgcc aagaactcactgtatctgcaaatgaacagcctgagagccgaggac acggctgtgtattactgtgcgagagagccctcccattacgatatt ttgactggttatgactactattacggtatggacgtctggggccaa gggaccacggtcaccgtctcctca | nucleotide sequence |
| 70. | QVQLVQSGGGLVQPGGSLRLSCAASGFTFSNYLMNWVRQAPGKGL EWLANIQEDGIEKYYVDSVKGRFTISRDNAKNSLYLQMNSLRAED TAVYYCAREPSHYDILTGYDYYYGMDVWGQGTTVTVSS | amino acid sequence |
| 71. | ggattcacctttagtaactatttg | nucleotide sequence |
| 72. | GFTFSNYL | amino acid sequence |
| 73. | atacaggaagatggaattgagaaa | nucleotide sequence |
| 74. | IQEDGIEK | amino acid sequence |
| 75. | gcgagagagccctcccattacgatattttgactggttatgactac tattacggtatggacgtc | nucleotide sequence |
| 76. | AREPSHYDILTGYDYYYGMDV | amino acid sequence |

TABLE 9-continued

| Informal Sequence Listing | | |
|---|---|---|
| SEQ ID NO. | | Description |
| 77. | gacatccagttgacccagtctccatcctccctgtctgcatctgta<br>ggagacagagtcaccatcacttgccgggcaagtcagggcattaga<br>aatgatttaggctggtatcagcagaaaccagggaaagcccctaag<br>cgcctgatctatgctgcatccagtttgcaaagtggggtcccatca<br>aggttcagcggcagtggatctgggacagaattcattctcacagtc<br>agcagcctgcagcctgaagactttgcaacttattactgtctacag<br>tataatagtaacccattcactttcggccctgggaccaaggtggag<br>atcaaacga | nucleotide<br>sequence |
| 78. | DIQLTQSPSSLSASVGDRVTITCRASQGIRNDLGWYQQKPGKAPK<br>RLIYAASSLQSGVPSRFSGSGSGTEFILTVSSLQPEDFATYYCLQ<br>YNSNPFTFGPGTKVEIKR | amino<br>acid<br>sequence |
| 79. | cagggcattagaaatgat | nucleotide<br>sequence |
| 80. | QGIRND | amino<br>acid<br>sequence |
| 81. | gctgcatcc | nucleotide<br>sequence |
| 82. | AAS | amino<br>acid<br>sequence |
| 83. | ctacagtataatagtaacccattcact | nucleotide<br>sequence |
| 84. | LQYNSNPFT | amino<br>acid<br>sequence |
| 85. | gaggtgcagctggtggagtctggggggaggcttggtccagcctggg<br>gggtccctgagactctcctgtgcagcctccggattcacctttagt<br>aactatttgatgaactgggtccgccaggctccagggaaggggctg<br>gagtggctggccaacatacaggaagatggaattgagaaatactat<br>gtggactctgtgaagggccgattcaccatctccagagacaacgcc<br>aagaactcactgtatctgcaaatgaacagcctgagagccgaggac<br>acggctgtgtattactgtgcgagagagccctcccattacgatatt<br>ttgactggttatgactactattacggtatggacgtctggggccaa<br>gggaccacggtcaccgtctcc | nucleotide<br>sequence |
| 86. | EVQLVESGGGLVQPGGSLRLSCAASGFTFSNYLMNWVRQAPGKGL<br>EWLANIQEDGIEKYYVDSVKGRFTISRDNAKNSLYLQMNSLRAED<br>TAVYYCAREPSHYDILTGYDYYYGMDVWGQGTTVTVS | amino<br>acid<br>sequence |
| 87. | gacatccagatgacccagtctccatcctccctgtctgcatctgta<br>ggagacagagtcaccatcacttgccgggcaagtcagggcattaga<br>aatgatttaggctggtatcagcagaaaccagggaaagcccctaag<br>cgcctgatctatgctgcatccagtttgcaaagtggggtcccatca<br>aggttcagcggcagtggatctgggacagaattcattctcacagtc<br>agcagcctgcagcctgaagactttgcaacttattactgtctacag<br>tataatagtaacccattcactttcggccctgggaccaaagtggat<br>atcaaa | nucleotide<br>sequence |
| 88. | DIQMTQSPSSLSASVGDRVTITCRASQGIRNDLGWYQQKPGKAPK<br>RLIYAASSLQSGVPSRFSGSGSGTEFILTVSSLQPEDFATYYCLQ<br>YNSNPFTFGPGTKVDIK | amino<br>acid<br>sequence |
| 89. | gaggtgcagctggtgcagtctggggggagccttggtacagcctggg<br>gggtccctgagactctcctgtacagcctctggtttcaccttcagt<br>aactacgacatgcactgggtccgccaaactacaggaaaaggtctg<br>gagtggatctcagctattgatactgctggtgacacatactatcca<br>ggctccgtgaagggccgattcaccgtctccagagaaaatgccaag<br>aactcctttttatcttcaaatgaacagcctgagagccggggacacg<br>gctgtgtattactgtgcaaggggaggggaagtattacgatattttg<br>actggtgactaccactactacggtatggacgtctggggccaaggg<br>accacggtcaccgtctcctca | nucleotide<br>sequence |
| 90. | EVQLVQSGGGALVQPGGSLRLSCTASGFTFSNYDMHWVRQTTGKGL<br>EWISAIDTAGDTYYPGSVKGRFTVSRENAKNSFYLQMNSLRAGDT<br>AVYYCAREGKYYDILTGDYHYYGMDVWGQGTTVTVSS | amino<br>acid<br>sequence |

TABLE 9-continued

| | Informal Sequence Listing | |
|---|---|---|
| SEQ ID NO. | | Description |
| 91. | ggtttcaccttcagtaactacgac | nucleotide sequence |
| 92. | GFTFSNYD | amino acid sequence |
| 93. | attgatactgctggtgacaca | nucleotide sequence |
| 94. | IDTAGDT | amino acid sequence |
| 95. | gcaagggaggggaagtattacgatattttgactggtgactaccac tactacggtatggacgtc | nucleotide sequence |
| 96. | AREGKYYDILTGDYHYYGMDV | amino acid sequence |
| 97. | gccatccggatgacccagtctccatcctccctgtctgcatctgta ggagacagagtcaccatcacttgtcgggcaagtcagggcattaga aatgatttaggctggtatcagcagaaaccagggaaagcccctaag cgactgatctatgctacatccagtttgcaaagtggggtcccatca aggttcagcggcagtggatctgggacagaattcactctcacaatc agcagcctgcagcctgaagattttgcaacttattactgtctacag cataatagttacccgctcactttcggcggagggaccaaggtggaa atcaaacga | nucleotide sequence |
| 98. | AIRMTQSPSSLSASVGDRVTITCRASQGIRNDLGWYQQKPGKAPK RLIYATSSLQSGVPSRFSGSGSGTEFTLTISSLQPEDFATYYCLQ HNSYPLTFGGGTKVEIKR | amino acid sequence |
| 99. | cagggcattagaaatgat | nucleotide sequence |
| 100. | QGIRND | amino acid sequence |
| 101. | gctacatcc | nucleotide sequence |
| 102. | ATS | amino acid sequence |
| 103. | ctacagcataatagttacccgctcact | nucleotide sequence |
| 104. | LQHNSYPLT | amino acid sequence |
| 105. | gaggtgcagctggtggagtctggggggagccttggtacagcctggg gggtccctgagactctcctgtacagcctctggtttcaccttcagt aactacgacatgcactgggtccgccaaactacaggaaaaggtctg gagtggatctcagctattgatactgctggtgacacatactatcca ggctccgtgaagggccgattcaccgtctccagagaaaatgccaag aactccttttatcttcaaatgaacagcctgagagccgggacacg gctgtgtattactgtgcaagggaggggaagtattacgatatttttg actggtgactaccactactacggtatggacgtctggggccaaggg accacggtcaccgtctcc | nucleotide sequence |
| 106. | EVQLVESGGALVQPGGSLRLSCTASGFTFSNYDMHWVRQTTGKGL EWISAIDTAGDTYYPGSVKGRFTVSRENAKNSFYLQMNSLRAGDT AVYYCAREGKYYDILTGDYHYYGMDVWGQGTTVTVS | amino acid sequence |
| 107. | gacatccagatgacccagtctccatcctccctgtctgcatctgta ggagacagagtcaccatcacttgtcgggcaagtcagggcattaga aatgatttaggctggtatcagcagaaaccagggaaagcccctaag cgactgatctatgctacatccagtttgcaaagtggggtcccatca | nucleotide sequence |

TABLE 9-continued

Informal Sequence Listing

| SEQ ID NO. | | Description |
| --- | --- | --- |
| | aggttcagcggcagtggatctgggacagaattcactctcacaatc agcagcctgcagcctgaagattttgcaacttattactgtctacag cataatagttacccgctcactttcggcggagggaccaagctggag atcaaa | |
| 108. | DIQMTQSPSSLSASVGDRVTITCRASQGIRNDLGWYQQKPGKAPK RLIYATSSLQSGVPSRFSGSGSGTEFTLTISSLQPEDFATYYCLQ HNSYPLTFGGGTKLEIK | amino acid sequence |
| 109. | caggtgcagctggtgcagtctgggggaggcgtggtccagcctggg aggtccctgagactctcctgtgcagcgtctgggttcacctttagt aactttggcatgcactgggtccgccaggctccaggcaaggggctg gagtgggtggcagttatatggtttgatgaaattgataaatactat gcagactccgtgaagggccgattcaccatctccagagacaattcc aagaacacgctgtatccgcaaatgaacagcctgagagccgaagac acggctgtgtattactgtgcgcgagaagattacgatattttgact ggttactattacgctatggacgtctggggccaagggaccacggtc accgtctcctca | nucleotide sequence |
| 110. | QVQLVQSGGGVVQPGRSLRLSCAASGFTFSNFGMHWVRQAPGKGL EWVAVIWFDEIDKYYADSVKGRFTISRDNSKNTLYPQMNSLRAED TAVYYCAREDYDILTGYYYAMDVWGQGTTVTVSS | amino acid sequence |
| 111. | gggttcacctttagtaactttggc | nucleotide sequence |
| 112. | GFTFSNFG | amino acid sequence |
| 113. | atatggtttgatgaaattgataaa | nucleotide sequence |
| 114. | IWFDEIDK | amino acid sequence |
| 115. | gcgcgagaagattacgatattttgactggttactattacgctatg gacgtc | nucleotide sequence |
| 116. | AREDYDILTGYYYAMDV | amino acid sequence |
| 117. | gacatccagatgacccagtctccatcctccctgtctgcatctgta ggagacagagtcaccatcacttgccgggcaagtcagggcattaga aatgatttaggctggtatcagcagaaaccagggaaagcccctaag cgcctaatctatgctgcatcccgtttgcaaagtggggtcccatcg aggttcagcggcagtggatctgggacagaattcactctcacaatc agcagcctgcagcctgaagattttggaacttattactgtctacag cataatagtcaccccaccttcggccaagggaccaaggtggagatc aaacga | nucleotide sequence |
| 118. | DIQMTQSPSSLSASVGDRVTITCRASQGIRNDLGWYQQKPGKAPK RLIYAASRLQSGVPSRFSGSGSGTEFTLTISSLQPEDFGTYYCLQ HNSHPTFGQGTKVEIKR | amino acid sequence |
| 119. | caggcattagaaatgat | nucleotide sequence |
| 120. | QGIRND | amino acid sequence |
| 121. | gctgcatcc | nucleotide sequence |
| 122. | AAS | amino acid sequence |

TABLE 9-continued

Informal Sequence Listing

| SEQ ID NO. | | Description |
|---|---|---|
| 123. | ctacagcataatagtcaccccacc | nucleotide sequence |
| 124. | LQHNSHPT | amino acid sequence |
| 125. | caggtgcagctggtggagtctggggggaggcgtggtccagcctggg aggtccctgagactctcctgtgcagcgtctgggttcacctttagt aactttggcatgcactgggtccgccaggctccaggcaaggggctg gagtgggtggcagttatatggtttgatgaaattgataaatactat gcagactccgtgaagggccgattcaccatctccagagacaattcc aagaacacgctgtatccgcaaatgaacagcctgagagccgaagac acggctgtgtattactgtgcgcgagaagattacgatattttgact ggttactattacgctatggacgtctgggggccaagggaccacggtc accgtctcc | nucleotide sequence |
| 126. | QVQLVESGGGVVQPGRSLRLSCAASGFTFSNFGMHWVRQAPGKGL EWVAVIWFDEIDKYYADSVKGRFTISRDNSKNTLYPQMNSLRAED TAVYYCAREDYDILTGYYYAMDVWGQGTTVTVS | amino acid sequence |
| 127. | gacatccagatgacccagtctccatcctccctgtctgcatctgta ggagacagagtcaccatcacttgccgggcaagtcagggcattaga aatgatttaggctggtatcagcagaaaccagggaaagcccctaag cgcctaatctatgctgcatcccgtttgcaaagtggggtcccatcg aggttcagcggcagtggatctgggacagaattcactctcacaatc agcagcctgcagcctgaagattttggaacttattactgtctacag cataatagtcaccccaccttcggccaagggaccaaggtggagatc aaa | nucleotide sequence |
| 128. | DIQMTQSPSSLSASVGDRVTITCRASQGIKNDLGWYQQKPGKAPK RLIYAASRLQSGVPSRFSGSGSGTEFTLTISSLQPEDFGTYYCLQ HNSHPTFGQGTKVEIK | amino acid sequence |
| 129. | gaggtgcagctggtggagtcggggggaggcatggtacagcctggg gggtccctgagactctcctgtgcagcctctggattcacctccagt aactacgacatgcactgggtccgccaagctacaggaaaaggtctg gagtgggtctcaagtattgatactgctggggacacttactatcca gactccgtgaagggccgctttatcatctccagagaaaatgccaaa aactccctgtatcttcaaatgaatagcctgagagccggggacacg gctgtgtattactgtacaagggagccccgaaattacgaaattttg actggtcactaccactaccacggtatggacatctgggggccaaggg accacggtcaccgtctcctca | nucleotide sequence |
| 130. | EVOLVESGGGMVQPGGSLRLSCAASGFTSSNYDMHWVRQATGKGL EWVSSIDTAGDTYYPDSVKGRFIISRENAKNSLYLQMNSLRAGDT AVYYCTREPRNYEILTGHYHYHGMDIWGQGTTVTVSS | amino acid sequence |
| 131. | ggattcacctccagtaactacgac | nucleotide sequence |
| 132. | GFTSSNYD | amino acid sequence |
| 133. | attgatactgctggggacact | nucleotide sequence |
| 134. | IDTAGDT | amino acid sequence |
| 135. | acaagggagccccgaaattacgaaattttgactggtcactaccac taccacggtatggacatc | nucleotide sequence |
| 136. | TREPRNYEILTGHYHYHGMDI | amino acid sequence |
| 137. | gacatccagatgacccagtcgccatcctccctgtctgcatctgta ggagacagagtcaccatcacttgccgggcaagtcaggccattaga aatgatttaggctggtatcagcagaaaccagggaaagcccctaaa ctcctgatctatactgcattcagtttacagagtggggtcccatca aggttcagcggcagtaaatctggcacagacttcactctcaccatc | nucleotide sequence |

TABLE 9-continued

Informal Sequence Listing

| SEQ ID NO. | | Description |
|---|---|---|
| | agcagcctgcagcctgaagattttgcgacttattactgtctgcag<br>gattacactaatcctcggacgttcggccaagggaccaaggtggag<br>atcaaacga | |
| 138. | DIQMTQSPSSLSASVGDRVTITCRASQAIRNDLGWYQQKPGKAPK<br>LLIYTAFSLQSGVPSRFSGSKSGTDFTLTISSLQPEDFATYYCLQ<br>DYTNPRTFGQGTKVEIKR | amino<br>acid<br>sequence |
| 139. | caggccattagaaatgat | nucleotide<br>sequence |
| 140. | QAIRND | amino<br>acid<br>sequence |
| 141. | actgcattc | nucleotide<br>sequence |
| 142. | TAF | amino<br>acid<br>sequence |
| 143. | ctgcaggattacactaatcctcggacg | nucleotide<br>sequence |
| 144. | LQDYTNPRT | amino<br>acid<br>sequence |
| 145. | gaggtgcagctggtggagtcggggggaggcatggtacagcctggg<br>gggtccctgagactctcctgtgcagcctctggattcacctccagt<br>aactacgacatgcactgggtccgccaagctacaggaaaaggtctg<br>gagtgggtctcaagtattgatactgctggggacacttactatcca<br>gactccgtgaagggccgctttatcatctccagagaaaatgccaaa<br>aactccctgtatcttcaaatgaatagcctgagagccgggggacacg<br>gctgtgtattactgtacaagggagccccgaaattacgaaattttg<br>actggtcactaccactaccacggtatggacatctggggccaaggg<br>accacggtcaccgtctcc | nucleotide<br>sequence |
| 146. | EVQLVESGGGMVQPGGSLRLSCAASGFTSSNYDMHWVRQATGKGL<br>EWVSSIDTAGDTYYPDSVKGRFIISRENAKNSLYLQMNSLRAGDT<br>AVYYCTREPRNYEILTGHYHYHGMDIWGQGTTVTVS | amino<br>acid<br>sequence |
| 147. | gccatccagatgacccagtcgccatcctccctgtctgcatctgta<br>ggagacagagtcaccatcacttgccgggcaagtcaggccattaga<br>aatgatttaggctggtatcagcagaaaccagggaaagcccctaaa<br>ctcctgatctatactgcattcagtttacagagtggggtcccatca<br>aggttcagcggcagtaaatctggcacagacttcactctcaccatc<br>agcagcctgcagcctgaagattttgcgacttattactgtctgcag<br>gattacactaatcctcggacgttcggccaagggaccaaggtggaa<br>atcaaa | nucleotide<br>sequence |
| 148. | AIQMTQSPSSLSASVGDRVTITCRASQAIRNDLGWYQQKPGKAPK<br>LLIYTAFSLQSGVPSRFSGSKSGTDFTLTISSLQPEDFATYYCLQ<br>DYTNPRTFGQGTKVEIK | amino<br>acid<br>sequence |
| 149. | caggtgcagctggtggagtctggggggaggcgtggtccagcctggg<br>aggtccctgagactctcctgtgcagcctctggattcgccttcagt<br>aactatggcatgcactgggtccgccaggctccaggcaaggggctg<br>gaatgggtgacatttatatcatatgatggaagtaataaatactat<br>gcagactccgtgaagggccgattcaccatctccagagacaattcc<br>aagaacacgctgtatctgcaagtgaacagcctgagagctgaggac<br>acggctgtgtattactgtgcgaaagaagcagtattagctgccctc<br>tttgactactggggccagggaaccctggtcaccgtctcctca | nucleotide<br>sequence |
| 150. | QVQLVESGGGVVQPGRSLRLSCAASGFAFSNYGMHWVRQAPGKGL<br>EWVTFISYDGSNKYYADSVKGRFTISRDNSKNTLYLQVNSLRAED<br>TAVYYCAKEAVLAALFDYWGQGTLVTVSS | amino<br>acid<br>sequence |
| 151. | ggattcgccttcagtaactatggc | nucleotide<br>sequence |

TABLE 9-continued

| SEQ ID NO. | | Description |
|---|---|---|
| | Informal Sequence Listing | |
| 152. | GFAFSNYG | amino acid sequence |
| 153. | atatcatatgatggaagtaataaa | nucleotide sequence |
| 154. | ISYDGSNK | amino acid sequence |
| 155. | gcgaaagaagcagtattagctgccctctttgactac | nucleotide sequence |
| 156. | AKEAVLAALFDY | amino acid sequence |
| 157. | gacatcgtgatgacccagtctccagactccctggctgtgtctctg ggcgagagggccaccatcaactgcaagtccagccagagtgtttta tacagctccaacaatcagaactacttagcttggtaccagcagaaa ccaggacagcctcctaagctgctcatttactgggcatctacccgg gaatccggggtccctgaccgattcagtggcagcgggtctgggaca gatttcactctcaccatcaacagcctgcaggctgaagatgtggca gtttattactgtcagcaatattatagtactcctacgttcggccaa gggaccaaggtggaaatcaaa | nucleotide sequence |
| 158. | DIVMTQSPDSLAVSLGERATINCKSSQSVLYSSNNQNYLAWYQQK PGQPPKLLIYWASTRESGVPDRFSGSGSGTDFTLTINSLQAEDVA VYYCQQYYSTPTFGQGTKVEIK | amino acid sequence |
| 159. | cagagtgttttatacagctccaacaatcagaactac | nucleotide sequence |
| 160. | QSVLYSSNNQNY | amino acid sequence |
| 161. | tgggcatct | nucleotide sequence |
| 162. | WAS | amino acid sequence |
| 163. | cagcaatattatagtactcctacg | nucleotide sequence |
| 164. | QQYYSTPT | amino acid sequence |
| 165. | caggtgcagctggtggagtctgggggaggcgtggtccagcctggg aggtccctgagactctcctgtgcagcctctggattcacgttcaat acctatggcatgcactgggtccgccaggctccagtcaaggggctg gagtgggtggcatttatatcaaatgataagagtaatacattctat gcagactccgtgaagggccgattcaccatctccagagacaattcc aagaacacgctgtttctggaaatgaacagcctgacagctgaggac acggctgtttattactgtgcgaaagagtccatttttagcagccctc tttgactactggggccagggaaccctggtcactgtctcctca | nucleotide sequence |
| 166. | QVQLVESGGGVVQPGRSLRLSCAASGFTFNTYGMHWVRQAPVKGL EWVAFISNDKSNTFYADSVKGRFTISRDNSKNTLFLEMNSLTAED TAVYYCAKESILAALFDYWGQGTLVTVSS | amino acid sequence |
| 167. | ggattcacgttcaatacctatggc | nucleotide sequence |
| 168. | GFTFNTYG | amino acid sequence |
| 169. | atatcaaatgataagagtaataca | nucleotide sequence |

TABLE 9-continued

| | Informal Sequence Listing | |
|---|---|---|
| SEQ ID NO. | | Description |
| 170. | ISNDKSNT | amino acid sequence |
| 171. | gcgaaagagtccattttagcagccctctttgactac | nucleotide sequence |
| 172. | AKESILAALFDY | amino acid sequence |
| 173. | gacatcgtgatgacccagtctccagactccctggctgtgtctctg ggcgagagggccaccatcaactgcaagtccagccagagtgtttta tacagctccaacaataagaattacttagcttggtaccaacagaaa ccaagacagcctcttaaactactcatttactgggcatctattcgg gaatccggggtccctgaccgattcagtggcagcgggtctgggaca gatttcactctcaccatcagcagcctgcaggctgaagatgtggca gtttattactgtcagcaattttatagtgttcccacttttggccag gggaccaagctggagatcaaa | nucleotide sequence |
| 174. | DIVMTQSPDSLAVSLGERATINCKSSQSVLYSSNNKNYLAWYQQK PRQPLKLLIYWASIRESGVPDRESGSGSGTDFTLTISSLQAEDVA VYYCQQFYSVPTFGQGTKLEIK | amino acid sequence |
| 175. | cagagtgttttatacagctccaacaataagaattac | nucleotide sequence |
| 176. | QSVLYSSNNKNY | amino acid sequence |
| 177. | tgggcatct | nucleotide sequence |
| 178. | WAS | amino acid sequence |
| 179. | cagcaattttatagtgttcccact | nucleotide sequence |
| 180. | QQFYSVPT | amino acid sequence |
| 181. | caggtgcagctggtggagtctggggggaggcgtggtccagcctggg aggtccctgagactctcctgtgcagcctctggattcacgtttagt acctttggcatgcactgggtccgccaggctccagtcaaggggctg gagtgggtggcttttatatcaaatgataagaataataaaattctat gcagactccgtgaagggccgattcaccatctccagagacaattcc agggacacgctatatctgcaaatgaacagcctgacacctgaggac acggctgtttattactgtgcgaaagagtccatttttagcagccctc tttgactactggggccagggaaccctggtcaccgtctcctca | nucleotide sequence |
| 182. | QVQLVESGGGVVQPGRSLRLSCAASGFTFSTFGMHWVRQAPVKGL EWVAFISNDKNNKFYADSVKGRFTISRDNSRDTLYLQMNSLTPED TAVYYCAKESILAALFDYWGQGTLVTVSS | amino acid sequence |
| 183. | ggattcacgtttagtacctttggc | nucleotide sequence |
| 184. | GFTFSTFG | amino acid sequence |
| 185. | atatcaaatgataagaataataaa | nucleotide sequence |
| 186. | ISNDKNNK | amino acid sequence |

TABLE 9-continued

| | Informal Sequence Listing | |
|---|---|---|
| SEQ ID NO. | | Description |
| 187. | gcgaaagagtccattttagcagccctctttgactac | nucleotide sequence |
| 188. | AKESILAALFDY | amino acid sequence |
| 189. | gacatcgtgatgacccagtctccagactccctggctgtgtctctg ggcgagagggccaccatcaactgcaagtccagccagagtgtttta tacagctccaacaataaaaattacttagcttggtaccagcagaaa ccaggacagcctcttaaacttctcatttactgggcatctattcgg gaatccggggtccctgaccgattcagtggcagcgggtctgggaca gatttcactctcaccatcagcagcctgcaggctgaagatgtggca gtttattactgtcagcaatttttatactgttcccacttttggcctg gggaccaagctggagatcaaa | nucleotide sequence |
| 190. | DIVMTQSPDSLAVSLGERATINCKSSQSVLYSSNNKNYLAWYQQK PGQPLKLLIYWASIRESGVPDRESGSGSGTDFTLTISSLQAEDVA VYYCQQFYTVPTFGLGTKLEIK | amino acid sequence |
| 191. | cagagtgttttatacagctccaacaataaaaattac | nucleotide sequence |
| 192. | QSVLYSSNNKNY | amino acid sequence |
| 193. | tgggcatct | nucleotide sequence |
| 194. | WAS | amino acid sequence |
| 195. | cagcaatttttatactgttcccact | nucleotide sequence |
| 196. | QQFYTVPT | amino acid sequence |
| 197. | caggtgcagctggtggagtctggggagggcgtggtccagcctggg aggtccctgagactctcctgtgtagcctctggattcaccttcagg aactatgacatgcactgggtccgccaggctcctggcaaggggctg gaatgggtggcagttacatcatctgatggacttaataaattctat tcagactccgtgaagggccgattcaccatctccagagacaattcc aagaacacgctgtctctgcaaattaccggcctgagagctgaggac acggctgtgtattactgtgcgaaagagtccattttagcagccctc tttgactactggggccagggaaccctggtcaccgtctcctca | nucleotide sequence |
| 198. | QVQLVESGGGVVQPGRSLRLSCVASGFTFRNYDMHWVRQAPGKGL EWVAVTSSDGLNKFYSDSVKGRFTISRDNSKNTLSLQITGLRAED TAVYYCAKESILAALFDYWGQGTLVTVSS | amino acid sequence |
| 199. | ggattcaccttcaggaactatgac | nucleotide sequence |
| 200. | GFTFRNYD | amino acid sequence |
| 201. | acatcatctgatggacttaataaa | nucleotide sequence |
| 202. | TSSDGLNK | amino acid sequence |
| 203. | gcgaaagagtccattttagcagccctctttgactac | nucleotide sequence |
| 204. | AKESILAALFDY | amino acid sequence |

TABLE 9-continued

| | Informal Sequence Listing | |
|---|---|---|
| SEQ ID NO. | | Description |
| 205. | gacatcgtgatgacccagtctccagactccctggctgtgtctctg ggcgagagggccaccatcaactgcaagtccagccagagtgtttta tacagctccaacaataagaactacttggcttggtaccagcagaaa ccaggacagcctcctaagctgctcttttactgggcatctacccgg gaatccgggggtccctgaccgattcagtggcagcgggtctgggaca gatttcactctcaccatcagcagcctgcaggctgaagatgtggca gtttattactgtcagcaacattatactactcccacttttggccag gggaccaagctggagatcaaa | nucleotide sequence |
| 206. | DIVMTQSPDSLAVSLGERATINCKSSQSVLYSSNNKNYLAWYQQK PGQPPKLLFYWASTRESGVPDRFSGSGSGTDFTLTISSLQAEDVA VYYCQQHYTTPTFGQGTKLEIK | amino acid sequence |
| 207. | cagagtgttttatacagctccaacaataagaactac | nucleotide sequence |
| 208. | QSVLYSSNNKNY | amino acid sequence |
| 209. | tgggcatct | nucleotide sequence |
| 210. | WAS | amino acid sequence |
| 211. | cagcaacattatactactcccact | nucleotide sequence |
| 212. | QQHYTTPT | amino acid sequence |
| 213. | caggtgcagctggtggagtctggggaggcgtggtccagcctggg aggtccctgagactctcctgtgcagcctctggattcaccttcagt agctatggcatgcactgggtccgccagactccgggcaaggggctg gagtgggtggcatttatatcatatgatggaaataataaatactat gcagactccgtgaagggccgattcaccatctccagagacaattcc aagaacacgctgtttctgcaaatgaacagcctgagagctgaggac acggctgtgtattactgtgcgaaagagtccatttttagcagccctc tttgactactggggccagggaaccctggtcaccgtctcctca | nucleotide sequence |
| 214. | QVQLVESGGGVVQPGRSLRLSCAASGFTFSSYGMHWVRQTPGKGL EWVAFISYDGNNKYYADSVKGRFTISRDNSKNTLFLQMNSLRAED TAVYYCAKESILAALFDYWGQGTLVTVSS | amino acid sequence |
| 215. | ggattcaccttcagtagctatggc | nucleotide sequence |
| 216. | GFTFSSYG | amino acid sequence |
| 217. | atatcatatgatggaaataataaa | nucleotide sequence |
| 218. | ISYDGNNK | amino acid sequence |
| 219. | gcgaaagagtccattttagcagccctctttgactac | nucleotide sequence |
| 220. | AKESILAALFDY | amino acid sequence |
| 221. | gacatcgtgatgacccagtctccagactccctggctgtgtctctg ggcgagagggccaccatcaactgcaagtccagccagagtgtttta tacagctccaacaataagaactacttagcttggtaccagcagaaa cctggacagcctcctaagctgctcatttactgggcatctacccgg gaatccgggggtccctgaccgattcagtggcagcgggtctgggaca | nucleotide sequence |

TABLE 9-continued

Informal Sequence Listing

| SEQ ID NO. | | Description |
|---|---|---|
| | gatttcactctcaccatcagcagcctgcaggctgaagatgtggca ctttattactgtcaacaatattataatactcccacttttggccag gggaccaagctggagatcaaa | |
| 222. | DIVMTQSPDSLAVSLGERATINCKSSQSVLYSSNNKNYLAWYQQK PGQPPKLLIYWASTRESGVPDRESGSGSGTDFTLTISSLQAEDVA LYYCQQYYNTPTFGQGTKLEIK | amino acid sequence |
| 223. | cagagtgtttttatacagctccaacaataagaactac | nucleotide sequence |
| 224. | QSVLYSSNNKNY | amino acid sequence |
| 225. | tgggcatct | nucleotide sequence |
| 226. | WAS | amino acid sequence |
| 227. | caacaatattataatactcccact | nucleotide sequence |
| 228. | QQYYNTPT | amino acid sequence |
| 229. | caggtgcagctggtggagtctggggggaggcgtggtccagcctggg aggtccctgagactctcctgtgcagcctctggattcaccttcagt agctatggcatgcactgggtccgccaggctccagtcaaggggctg gagtgggtggcatttatatcatatgatggaagtaataaatactat gcagactccgtgaagggccgattcaccatctccagagacaattcc aagaacacgctgtatctccaaatgaacagcctgacagctgaggac acggctgtttattactgtgcgaaagagtccatttttagcagccctc tttgactactggggccagggaaccctggtcaccgtctcctca | nucleotide sequence |
| 230. | QVQLVESGGGVVQPGRSLRLSCAASGFTFSSYGMHWVRQAPVKGL EWVAFISYDGSNKYYADSVKGRFTISRDNSKNTLYLQMNSLTAED TAVYYCAKESILAALFDYWGQGTLVTVSS | amino acid sequence |
| 231. | ggattcaccttcagtagctatggc | nucleotide sequence |
| 232. | GFTFSSYG | amino acid sequence |
| 233. | atatcatatgatggaagtaataaa | nucleotide sequence |
| 234. | ISYDGSNK | amino acid sequence |
| 235. | gcgaaagagtccatttttagcagccctctttgactac | nucleotide sequence |
| 236. | AKESILAALFDY | amino acid sequence |
| 237. | gacatcgtgatgacccagtctccagactccctggctgtgtctctg ggcgagagggccaccatcaactgcaagtccagccagagtgttttta tacagttccaacaataagaactacttagcttggtaccagcagaaa ccaagacagcctcctaagctgctcatttactgggcatctattcgg gaatccggggtccctgaccgattcagtggcagcgggtctgggaca gatttcattctcaccatcagcagcctgcaggctgaagatgtggca gtttattactgtcagcaatttttatagtattcccacttttggccag gggaccaagctggagatcaaa | nucleotide sequence |

TABLE 9-continued

Informal Sequence Listing

| SEQ ID NO. | | Description |
|---|---|---|
| 238. | DIVMTQSPDSLAVSLGERATINCKSSQSVLYSSNNKNYLAWYQQK PRQPPKLLIYWASIRESGVPDRFSGSGSGTDFILTISSLQAEDVA VYYCQQFYSIPTFGQGTKLEIK | amino acid sequence |
| 239. | cagagtgttttatacagttccaacaataagaactac | nucleotide sequence |
| 240. | QSVLYSSNNKNY | amino acid sequence |
| 241. | tgggcatct | nucleotide sequence |
| 242. | WAS | amino acid sequence |
| 243. | cagcaattttatagtattcccact | nucleotide sequence |
| 244. | QQFYSIPT | amino acid sequence |
| 245. | caggtgcagctggtggagtctggggggaggcgtggtccagcctggg aggtccctgagactctcctgtgcagcctctggattcacctttagt agctatggcatgcactgggtccgccaggctccagtcaaggggctg gagtgggtggcatttatatcaaatgataaaagtaataaatattat gcagactccttgaagggccgattcaccatctccagagacaattcc aagaacacgctgtatctgcaaatgaacagcctgacagctgaagac acggctgtttattactgtgcgaaagagtccattttagcagccctc tttgactattggggccagggaaccctggtcaccgtctcctca | nucleotide sequence |
| 246. | QVQLVESGGGVVQPGRSLRLSCAASGFTFSSYGMHWVRQAPVKGL EWVAFISNDKSNKYYADSLKGRFTISRDNSKNTLYLQMNSLTAED TAVYYCAKESILAALFDYWGQGTLVTVSS | amino acid sequence |
| 247. | ggattcacctttagtagctatggc | nucleotide sequence |
| 248. | GFTFSSYG | amino acid sequence |
| 249. | atatcaaatgataaaagtaataaa | nucleotide sequence |
| 250. | ISNDKSNK | amino acid sequence |
| 251. | gcgaaagagtccattttagcagccctctttgactat | nucleotide sequence |
| 252. | AKESILAALFDY | amino acid sequence |
| 253. | gacatcgtgatgacccagtctccagactccctggctgtgtctctg ggcgagagggccaccatcaactgcaagtccagccagagtgtttta tacagctccaacaataagaactacttagcttggtaccagcagaaa ccaagacagcctcctaagctactcatttactgggcatctattcgg gaatccggggtccctgaccgattcagtggcagcgggtctgggaca gatttcactctcaccatcagcagcctgcaggctgaagatgtggca gtttattactgtcaacaattttatagtgttcccacttttggccag gggaccaagctggagatcaaa | nucleotide sequence |
| 254. | DIVMTQSPDSLAVSLGERATINCKSSQSVLYSSNNKNYLAWYQQK PRQPPKLLIYWASIRESGVPDRFSGSGSGTDFTLTISSLQAEDVA VYYCQQFYSVPTFGQGTKLEIK | amino acid sequence |

TABLE 9-continued

Informal Sequence Listing

| SEQ ID NO. | | Description |
| --- | --- | --- |
| 255. | cagagtgttttatacagctccaacaataagaactac | nucleotide sequence |
| 256. | QSVLYSSNNKNY | amino acid sequence |
| 257. | tgggcatct | nucleotide sequence |
| 258. | WAS | amino acid sequence |
| 259. | caacaattttatagtgttcccact | nucleotide sequence |
| 260. | QQFYSVPT | amino acid sequence |
| 261. | caggtgcagctggtggagtctggggggaggcgtggtccagcctggg aggtccctgagactctcctgtgcagcctctggattcaccttcagt agctatggcatgcactgggtccgccaggctccagtcaaggggctg gagtgggtggcatttatatcatttgatggaagtaataaatactat acagactccgtgaagggccgattcaccatctccagagacaattcc aagaacacgctgtatctccaaatgaacagcctgacagctgaggac acggctatttattactgtgcgaaagagtccattttagcagccctc tttgactactggggccagggaaccctggtcactgtctcctca | nucleotide sequence |
| 262. | QVQLVESGGGVVQPGRSLRLSCAASGFTFSSYGMHWVRQAPVKGL EWVAFISFDGSNKYYTDSVKGRFTISRDNSKNTLYLQMNSLTAED TAIYYCAKESILAALFDYWGQGTLVTVSS | amino acid sequence |
| 263. | ggattcaccttcagtagctatggc | nucleotide sequence |
| 264. | GFTFSSYG | amino acid sequence |
| 265. | atatcatttgatggaagtaataaa | nucleotide sequence |
| 266. | ISFDGSNK | amino acid sequence |
| 267. | gcgaaagagtccattttagcagccctctttgactac | nucleotide sequence |
| 268. | AKESILAALFDY | amino acid sequence |
| 269. | gacatcgtgatgacccagtctccagactccctggctgtgtctctg ggcgagagggccaccatcaactgcaagtccagccagagtgtttta tacagctccaacaataagaactacttagcttggtaccagcagaaa ccaagacagcctcctaacctgctcatttactgggcatctattcgg gaatccggggtccctgaccgattcagtggcagcgggtctgggaca gatttcactctcaccatcagcagcctgcaggctgaagatgtggca ttttattactgtcagcaattttatagtattcccacttttggccag gggaccaagctggagatcaaa | nucleotide sequence |
| 270. | DIVMTQSPDSLAVSLGERATINCKSSQSVLYSSNNKNYLAWYQQK PRQPPNLLIYWASIRESGVPDRFSGSGSGTDFTLTISSLQAEDVA FYYCQQFYSIPTFGQGTKLEIK | amino acid sequence |
| 271. | cagagtgttttatacagctccaacaataagaactac | nucleotide sequence |
| 272. | QSVLYSSNNKNY | amino acid sequence |

TABLE 9-continued

Informal Sequence Listing

| SEQ ID NO. | | Description |
|---|---|---|
| 273. | tgggcatct | nucleotide sequence |
| 274. | WAS | amino acid sequence |
| 275. | cagcaattttatagtattcccact | nucleotide sequence |
| 276. | QQFYSIPT | amino acid sequence |
| 277. | caggtgcagctggtggagtctggggggaggcgtggtccagcctggg aggtccctgagactctcctgtgcagcctctggattcacctttagg acctatggcatgcactgggtccgccaggctccagtcaaggggctg gagtgggtggcatttatatcaaaggatggaagtgataaatactat gtagactccgtgaagggccgattcaccatctccagagacaattcc aagaacacgctgtttctgcaaatgaacagcctgacagctgaggac acggctgtttattattgtgcgaaagagtccatttttagcagccctc tttgactactggggccagggaaccctggtcactgtctcctca | nucleotide sequence |
| 278. | QVQLVESGGGVVQPGRSLRLSCAASGFTFRTYGMHWVRQAPVKGL EWVAFISKDGSDKYYVDSVKGRFTISRDNSKNTLFLQMNSLTAED TAVYYCAKESILAALFDYWGQGTLVTVSS | amino acid sequence |
| 279. | ggattcacctttaggacctatggc | nucleotide sequence |
| 280. | GFTFRTYG | amino acid sequence |
| 281. | atatcaaaggatggaagtgataaa | nucleotide sequence |
| 282. | ISKDGSDK | amino acid sequence |
| 283. | gcgaaagagtccatttttagcagccctctttgactac | nucleotide sequence |
| 284. | AKESILAALFDY | amino acid sequence |
| 285. | gacatcgtgatgacccagtctccagactccctggctgtgtctctg ggcgagagggccaccatcaactgcaagtccagccagagtgtttta tacagctccaacaataagaactacttagcttggtaccagcagaaa ccaagacagcctcctaaactcctcatttactgggcatctaatcgg gaatccggggtccctgaccgattcagtggcagcgggtctgggaca gatttcactctcaccatcagcagcctgcaggctgaagatgtggca gtttattactgtcagcaattttatagtgttcccacttttggccag gggaccaagctggagatcaaa | nucleotide sequence |
| 286. | DIVMTQSPDSLAVSLGERATINCKSSQSVLYSSNNKNYLAWYQQK PRQPPKLLIYWASNRESGVPDRFSGSGSGTDFTLTISSLQAEDVA VYYCQQFYSVPTFGQGTKLEIK | amino acid sequence |
| 287. | cagagtgttttatacagctccaacaataagaactac | nucleotide sequence |
| 288. | QSVLYSSNNKNY | amino acid sequence |
| 289. | tgggcatct | nucleotide sequence |

TABLE 9-continued

Informal Sequence Listing

| SEQ ID NO. | | Description |
|---|---|---|
| 290. | WAS | amino acid sequence |
| 291. | cagcaattttatagtgttcccact | nucleotide sequence |
| 292. | QQFYSVPT | amino acid sequence |
| 293. | caggtgcagctggtggagtctggggggaggcgtggtccagcctggg aggtccctgagactctcctgtgcagcctctggattcacctttagt agctatggcatgcactgggtccgccaggctccagtcaaggggctg gagtgggtggcatttatatcaaatgataaaagtaataaatactat gcagactccgtgaagggccgattcaccatctccagagacaattcc aagaacacgctgtatctgcaaatgaacagcctgacagctgaggac acggctgtttattactgtgcgaaagagtccattttagcagccctc tttgactcctggggccagggaaccctggtcaccgtctcctca | nucleotide sequence |
| 294. | QVQLVESGGGVVQPGRSLRLSCAASGFTFSSYGMHWVRQAPVKGL EWVAFISNDKSNKYYADSVKGRFTISRDNSKNTLYLQMNSLTAED TAVYYCAKESILAALFDSWGQGTLVTVSS | amino acid sequence |
| 295. | ggattcacctttagtagctatggc | nucleotide sequence |
| 296. | GFTFSSYG | amino acid sequence |
| 297. | atatcaaatgataaaagtaataaa | nucleotide sequence |
| 298. | ISNDKSNK | amino acid sequence |
| 299. | gcgaaagagtccattttagcagccctctttgactcc | nucleotide sequence |
| 300. | AKESILAALFDS | amino acid sequence |
| 301. | gacatcgtgatgacccagtctccagactccctggctgtgtctctg ggcgagagggccaccatcaactgcaagtccagccagagtgtttta tacagctccaacaataagaactacttagcttggtaccagcagaaa ccaagacagcctcctaagctgctcatttactgggcatctattcgg gaatccggggtccctgaccgattcagtggcagcgggtctgggca gatttcactctcaccatcagcagcctgcaggctgcagatgtggca gtttattactgtcagcaattttatagtgttcccacttttggccag gggaccaagctggagatcaaa | nucleotide sequence |
| 302. | DIVMTQSPDSLAVSLGERATINCKSSQSVLYSSNNKNYLAWYQQK PRQPPKLLIYWASIRESGVPDRESGSGSGADFTLTISSLQAADVA VYYCQQFYSVPTFGQGTKLEIK | amino acid sequence |
| 303. | cagagtgttttatacagctccaacaataagaactac | nucleotide sequence |
| 304. | QSVLYSSNNKNY | amino acid sequence |
| 305. | tgggcatct | nucleotide sequence |
| 306. | WAS | amino acid sequence |
| 307. | cagcaattttatagtgttcccact | nucleotide sequence |

TABLE 9-continued

| Informal Sequence Listing | |
|---|---|
| SEQ ID NO. | Description |
| 308. QQFYSVPT | amino acid sequence |

SEQUENCE LISTING

```
Sequence total quantity: 308
SEQ ID NO: 1               moltype = DNA   length = 375
FEATURE                    Location/Qualifiers
misc_feature               1..375
                           note = Synthetic
source                     1..375
                           mol_type = other DNA
                           organism = synthetic construct
SEQUENCE: 1
caggtccagt tggtacagtc tggggctgac gtgaagaagc ctggggcctc agtgaaggtc   60
tcctgcaagg tttccggaca tatcctcact gatttatcca tgcactgggt gcgacagcct  120
cctggaaaag gacttgagtg gatggcaggt tttgatcctg aagaaggtaa aataatctac  180
gcacagaagt tccagggcag agtcaccatg accgaggaca catctacaga cacagcctac  240
atggagctga gcagcctgag atctggggac acggccgttt attactgtgc aacaagcgat  300
attttgactg ggtattatag agactactac ggttttggacg tctggggcca agggaccacg  360
ctcaccgtct cctca                                                    375

SEQ ID NO: 2               moltype = AA   length = 125
FEATURE                    Location/Qualifiers
REGION                     1..125
                           note = Synthetic
source                     1..125
                           mol_type = protein
                           organism = synthetic construct
SEQUENCE: 2
QVQLVQSGAD VKKPGASVKV SCKVSGHILT DLSMHWVRQP PGKGLEWMAG FDPEEGKIIY   60
AQKFQGRVTM TEDTSTDTAY MELSSLRSGD TAVYYCATSD ILTGYYRDYY GLDVWGQGTT  120
LTVSS                                                               125

SEQ ID NO: 3               moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 3
ggacatatcc tcactgattt atcc                                          24

SEQ ID NO: 4               moltype = AA   length = 8
FEATURE                    Location/Qualifiers
REGION                     1..8
                           note = Synthetic
source                     1..8
                           mol_type = protein
                           organism = synthetic construct
SEQUENCE: 4
GHILTDLS                                                            8

SEQ ID NO: 5               moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 5
tttgatcctg aagaaggtaa aata                                          24

SEQ ID NO: 6               moltype = AA   length = 8
FEATURE                    Location/Qualifiers
REGION                     1..8
```

```
                         note = Synthetic
source                   1..8
                         mol_type = protein
                         organism = synthetic construct
SEQUENCE: 6
FDPEEGKI                                                          8

SEQ ID NO: 7             moltype = DNA   length = 54
FEATURE                  Location/Qualifiers
misc_feature             1..54
                         note = Synthetic
source                   1..54
                         mol_type = other DNA
                         organism = synthetic construct
SEQUENCE: 7
gcaacaagcg atattttgac tgggtattat agagactact acggtttgga cgtc      54

SEQ ID NO: 8             moltype = AA   length = 18
FEATURE                  Location/Qualifiers
REGION                   1..18
                         note = Synthetic
source                   1..18
                         mol_type = protein
                         organism = synthetic construct
SEQUENCE: 8
ATSDILTGYY RDYYGLDV                                               18

SEQ ID NO: 9             moltype = DNA   length = 336
FEATURE                  Location/Qualifiers
misc_feature             1..336
                         note = Synthetic
source                   1..336
                         mol_type = other DNA
                         organism = synthetic construct
SEQUENCE: 9
gatattgtga tgactcagtc tccactcttc ctgcccgtca cccctggaga gccggcctcc  60
atctcctgca ggtctagtca gagcctcctg catagtaaag gatacaacta tttggattgg  120
tacctgcaga agccagggca gtctccacaa ctcctgatct atttgggttc taatcggccc  180
tccgggggtcc ctgacaggtt cagtggcagt ggatcaggca cagatttac actgaaaatc  240
agcagagtgg aggctgaaga tgttgggggt tattactgca tgcaaactct acaaactcct  300
cggacgttcg gccaagggac caaggtggaa atcaaa                          336

SEQ ID NO: 10            moltype = AA   length = 112
FEATURE                  Location/Qualifiers
REGION                   1..112
                         note = Synthetic
source                   1..112
                         mol_type = protein
                         organism = synthetic construct
SEQUENCE: 10
DIVMTQSPLF LPVTPGEPAS ISCRSSQSLL HSKGYNYLDW YLQKPGQSPQ LLIYLGSNRA  60
SGVPDRFSGS GSGTDFTLKI SRVEAEDVGV YYCMQTLQTP RTFGQGTKVE IK          112

SEQ ID NO: 11            moltype = DNA   length = 33
FEATURE                  Location/Qualifiers
misc_feature             1..33
                         note = Synthetic
source                   1..33
                         mol_type = other DNA
                         organism = synthetic construct
SEQUENCE: 11
cagagcctcc tgcatagtaa aggatacaac tat                             33

SEQ ID NO: 12            moltype = AA   length = 11
FEATURE                  Location/Qualifiers
REGION                   1..11
                         note = Synthetic
source                   1..11
                         mol_type = protein
                         organism = synthetic construct
SEQUENCE: 12
QSLLHSKGYN Y                                                      11

SEQ ID NO: 13            moltype =    length =
SEQUENCE: 13
000

SEQ ID NO: 14            moltype =    length =
SEQUENCE: 14
```

-continued

```
000

SEQ ID NO: 15              moltype = DNA   length = 27
FEATURE                    Location/Qualifiers
misc_feature               1..27
                           note = Synthetic
source                     1..27
                           mol_type = other DNA
                           organism = synthetic construct
SEQUENCE: 15
atgcaaactc tacaaactcc tcggacg                                        27

SEQ ID NO: 16              moltype = AA   length = 9
FEATURE                    Location/Qualifiers
REGION                     1..9
                           note = Synthetic
source                     1..9
                           mol_type = protein
                           organism = synthetic construct
SEQUENCE: 16
MQTLQTPRT                                                            9

SEQ ID NO: 17              moltype = DNA   length = 375
FEATURE                    Location/Qualifiers
misc_feature               1..375
                           note = Synthetic
source                     1..375
                           mol_type = other DNA
                           organism = synthetic construct
SEQUENCE: 17
caggtccagt tggtacagtc tggggctgac gtgaagaagc ctggggcctc agtgaaggtc   60
tcctgcaagg tttccggaca tatcctcact gatttatcca tgcactgggt gcgacaggct   120
cctggaaaag ggcttgagtg gatgggaggt tttgatcctg aagaaggtga ataatctac    180
gcacagaagt tccagggcag agtcaccatg accgaggaca catctacaga cacagcctac   240
atggagctga gcagcctgag atctgggggac acggccgttt attactgtgc aacaagcgat   300
attttgactg gttattatag agactactac ggtttggacg tctgggggcca agggaccacg   360
ctcaccgtct cctca                                                    375

SEQ ID NO: 18              moltype = AA   length = 125
FEATURE                    Location/Qualifiers
REGION                     1..125
                           note = Synthetic
source                     1..125
                           mol_type = protein
                           organism = synthetic construct
SEQUENCE: 18
QVQLVQSGAD VKKPGASVKV SCKVSGHILT DLSMHWVRQA PGKGLEWMGG FDPEEGEIIY    60
AQKFQGRVTM TEDTSTDTAY MELSSLRSGD TAVYYCATSD ILTGYYRDYY GLDVWGQGTT    120
LTVSS                                                                125

SEQ ID NO: 19              moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 19
ggacatatcc tcactgattt atcc                                           24

SEQ ID NO: 20              moltype = AA   length = 8
FEATURE                    Location/Qualifiers
REGION                     1..8
                           note = Synthetic
source                     1..8
                           mol_type = protein
                           organism = synthetic construct
SEQUENCE: 20
GHILTDLS                                                             8

SEQ ID NO: 21              moltype = DNA   length = 24
FEATURE                    Location/Qualifiers
misc_feature               1..24
                           note = Synthetic
source                     1..24
                           mol_type = other DNA
                           organism = synthetic construct
SEQUENCE: 21
tttgatcctg aagaaggtga aata                                           24
```

-continued

```
SEQ ID NO: 22          moltype = AA   length = 8
FEATURE                Location/Qualifiers
REGION                 1..8
                       note = Synthetic
source                 1..8
                       mol_type = protein
                       organism = synthetic construct
SEQUENCE: 22
FDPEEGEI                                                              8

SEQ ID NO: 23          moltype = DNA  length = 54
FEATURE                Location/Qualifiers
misc_feature           1..54
                       note = Synthetic
source                 1..54
                       mol_type = other DNA
                       organism = synthetic construct
SEQUENCE: 23
gcaacaagcg atattttgac tggttattat agagactact acggtttgga cgtc        54

SEQ ID NO: 24          moltype = AA   length = 18
FEATURE                Location/Qualifiers
REGION                 1..18
                       note = Synthetic
source                 1..18
                       mol_type = protein
                       organism = synthetic construct
SEQUENCE: 24
ATSDILTGYY RDYYGLDV                                                   18

SEQ ID NO: 25          moltype = DNA  length = 336
FEATURE                Location/Qualifiers
misc_feature           1..336
                       note = Synthetic
source                 1..336
                       mol_type = other DNA
                       organism = synthetic construct
SEQUENCE: 25
gatattgtga tgactcagtc tccactcttc ctgcccgtca cccctggaga gccggcctcc   60
atctcctgca ggtctagtca gagcctcctg catagtaaag gatacaacta tttggattgg   120
tacctgcaga agccagggca gtctccacaa ctcctgatct atttgggttc taatcgggcc   180
tccggggtcc ctgacaggtt cagtggcagt ggatcaggca cagattttac actgaaaatc   240
agcagagtgg aggctgaaga tgttggggtt tattactgca tgcaaactct acaaactcct   300
cggacgttcg gccaagggac caaggtggaa atcaaa                             336

SEQ ID NO: 26          moltype = AA   length = 112
FEATURE                Location/Qualifiers
REGION                 1..112
                       note = Synthetic
source                 1..112
                       mol_type = protein
                       organism = synthetic construct
SEQUENCE: 26
DIVMTQSPLF LPVTPGEPAS ISCRSSQSLL HSKGYNYLDW YLQKPGQSPQ LLIYLGSNRA   60
SGVPDRFSGS GSGTDFTLKI SRVEAEDVGV YYCMQTLQTP RTFGQGTKVE IK           112

SEQ ID NO: 27          moltype = DNA  length = 33
FEATURE                Location/Qualifiers
misc_feature           1..33
                       note = Synthetic
source                 1..33
                       mol_type = other DNA
                       organism = synthetic construct
SEQUENCE: 27
cagagcctcc tgcatagtaa aggatacaac tat                                33

SEQ ID NO: 28          moltype = AA   length = 11
FEATURE                Location/Qualifiers
REGION                 1..11
                       note = Synthetic
source                 1..11
                       mol_type = protein
                       organism = synthetic construct
SEQUENCE: 28
QSLLHSKGYN Y                                                          11

SEQ ID NO: 29          moltype =    length =
SEQUENCE: 29
```

-continued

```
000

SEQ ID NO: 30          moltype =   length =
SEQUENCE: 30
000

SEQ ID NO: 31          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 31
atgcaaactc tacaaactcc tcggacg                                 27

SEQ ID NO: 32          moltype = AA  length = 9
FEATURE                Location/Qualifiers
REGION                 1..9
                       note = Synthetic
source                 1..9
                       mol_type = protein
                       organism = synthetic construct
SEQUENCE: 32
MQTLQTPRT                                                     9

SEQ ID NO: 33          moltype = DNA  length = 372
FEATURE                Location/Qualifiers
misc_feature           1..372
                       note = Synthetic
source                 1..372
                       mol_type = other DNA
                       organism = synthetic construct
SEQUENCE: 33
gaggagcaac tggtggagtc tgggggagac ttggtacagc ctggagggtc cctaagactc  60
tcctgtgcag cctctggatt cactctcagt agttatgaaa tgaactgggt ccgccaggct  120
ccagggaagg ggctggagtg ggtttcatac attagtagag gtggtagtct gatacactac  180
acagactctg tgaagggccg attcaccatc tccagagaca cgccaagaa ttcactgtat  240
ctgcaaatga acagcctgag agccgaggac acggctgttt attactgtgt gagagaccca  300
gcagctcgtt atcattatta ttatcacggt atggacgtct ggggccaagg gaccacggtc  360
accgtctcct ca                                                372

SEQ ID NO: 34          moltype = AA  length = 124
FEATURE                Location/Qualifiers
REGION                 1..124
                       note = Synthetic
source                 1..124
                       mol_type = protein
                       organism = synthetic construct
SEQUENCE: 34
EEQLVESGGD LVQPGGSLRL SCAASGFTLS SYEMNWVRQA PGKGLEWVSY ISRGGSLIHY  60
TDSVKGRFTI SRDNAKNSLY LQMNSLRAED TAVYYCVRDP AARYHYYYHG MDVWGQGTTV  120
TVSS                                                          124

SEQ ID NO: 35          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 35
ggattcactc tcagtagtta tgaa                                    24

SEQ ID NO: 36          moltype = AA  length = 8
FEATURE                Location/Qualifiers
REGION                 1..8
                       note = Synthetic
source                 1..8
                       mol_type = protein
                       organism = synthetic construct
SEQUENCE: 36
GFTLSSYE                                                      8

SEQ ID NO: 37          moltype = DNA  length = 24
FEATURE                Location/Qualifiers
misc_feature           1..24
                       note = Synthetic
source                 1..24
```

-continued

```
                         mol_type = other DNA
                         organism = synthetic construct
SEQUENCE: 37
attagtagag gtggtagtct gata                                       24

SEQ ID NO: 38           moltype = AA  length = 8
FEATURE                 Location/Qualifiers
REGION                  1..8
                        note = Synthetic
source                  1..8
                        mol_type = protein
                        organism = synthetic construct
SEQUENCE: 38
ISRGGSLI                                                          8

SEQ ID NO: 39           moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 39
gtgagagacc cagcagctcg ttatcattat tattatcacg gtatggacgt c          51

SEQ ID NO: 40           moltype = AA  length = 17
FEATURE                 Location/Qualifiers
REGION                  1..17
                        note = Synthetic
source                  1..17
                        mol_type = protein
                        organism = synthetic construct
SEQUENCE: 40
VRDPAARYHY YYHGMDV                                                17

SEQ ID NO: 41           moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 41
gatattgtga tgactcagtc tccactctcc ctgcccgtca cccctggaga gccggcctcc  60
atctcctgca ggtctagtca gagcctcctg cacaataatg gatataacta tttggattgg  120
tatctgcaga agccagggca gtctccacag ctcctgatct atttgggttc tagtcgggcc  180
tccggggtcc ctgacaggtt cagtggcagt ggatcaggca cagattttat actgaaaatc  240
agcagagtgg aggctgaaga tgttggggtt tattactgca tgcaagctct acaaactccg  300
tggacgttcg gccgagggac caaggtggaa atcaaa                           336

SEQ ID NO: 42           moltype = AA  length = 112
FEATURE                 Location/Qualifiers
REGION                  1..112
                        note = Synthetic
source                  1..112
                        mol_type = protein
                        organism = synthetic construct
SEQUENCE: 42
DIVMTQSPLS LPVTPGEPAS ISCRSSQSLL HNNGYNYLDW YLQKPGQSPQ LLIYLGSSRA  60
SGVPDRFSGS GSGTDFILKI SRVEAEDVGV YYCMQALQTP WTFGRGTKVE IK          112

SEQ ID NO: 43           moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 43
cagagcctcc tgcacaataa tggatataac tat                             33

SEQ ID NO: 44           moltype = AA  length = 11
FEATURE                 Location/Qualifiers
REGION                  1..11
                        note = Synthetic
source                  1..11
                        mol_type = protein
                        organism = synthetic construct
SEQUENCE: 44
```

```
QSLLHNNGYN Y                                                         11

SEQ ID NO: 45          moltype =   length =
SEQUENCE: 45
000

SEQ ID NO: 46          moltype =   length =
SEQUENCE: 46
000

SEQ ID NO: 47          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 47
atgcaagctc tacaaactcc gtggacg                                       27

SEQ ID NO: 48          moltype = AA   length = 9
FEATURE                Location/Qualifiers
REGION                 1..9
                       note = Synthetic
source                 1..9
                       mol_type = protein
                       organism = synthetic construct
SEQUENCE: 48
MQALQTPWT                                                           9

SEQ ID NO: 49          moltype = DNA   length = 384
FEATURE                Location/Qualifiers
misc_feature           1..384
                       note = Synthetic
source                 1..384
                       mol_type = other DNA
                       organism = synthetic construct
SEQUENCE: 49
gaggtgcagc tggtggagtc tggggagggc gtggtccagc ctgggaggtc cctgagactc   60
tcctgtgcag cctctggatt caccttcagt agttatgaca tgcactgggt ccgccaggct   120
ccaggcaagg ggctggagtg ggtggcagtt atatcatctg atggacgtga taaatactat   180
gtagactccg tgaagggccg attcaccatc tccagagaca actccaagaa cacgctttat   240
ctgcaaatga acagcctgag agctgaggac acggctgttt attactgtgc gaaagagatg   300
gtgtattacg atattttgac tggttatcat aactactacg gtatggacgt ctggggccaa   360
gggaccacgg tcaccgtctc ctca                                          384

SEQ ID NO: 50          moltype = AA   length = 128
FEATURE                Location/Qualifiers
REGION                 1..128
                       note = Synthetic
source                 1..128
                       mol_type = protein
                       organism = synthetic construct
SEQUENCE: 50
EVQLVESGGG VVQPGRSLRL SCAASGFTFS SYDMHWVRQA PGKGLEWVAV ISSDGRDKYY   60
VDSVKGRFTI SRDNSKNTLY LQMNSLRAED TAVYYCAKEM VYYDILTGYH NYYGMDVWGQ   120
GTTVTVSS                                                            128

SEQ ID NO: 51          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 51
ggattcacct tcagtagtta tgac                                          24

SEQ ID NO: 52          moltype = AA   length = 8
FEATURE                Location/Qualifiers
REGION                 1..8
                       note = Synthetic
source                 1..8
                       mol_type = protein
                       organism = synthetic construct
SEQUENCE: 52
GFTFSSYD                                                            8

SEQ ID NO: 53          moltype = DNA   length = 24
```

```
FEATURE               Location/Qualifiers
misc_feature          1..24
                      note = Synthetic
source                1..24
                      mol_type = other DNA
                      organism = synthetic construct
SEQUENCE: 53
atatcatctg atggacgtga taaa                                                    24

SEQ ID NO: 54         moltype = AA  length = 8
FEATURE               Location/Qualifiers
REGION                1..8
                      note = Synthetic
source                1..8
                      mol_type = protein
                      organism = synthetic construct
SEQUENCE: 54
ISSDGRDK                                                                       8

SEQ ID NO: 55         moltype = DNA  length = 63
FEATURE               Location/Qualifiers
misc_feature          1..63
                      note = Synthetic
source                1..63
                      mol_type = other DNA
                      organism = synthetic construct
SEQUENCE: 55
gcgaaagaga tggtgtatta cgatattttg actggttatc ataactacta cggtatggac  60
gtc                                                                           63

SEQ ID NO: 56         moltype = AA  length = 21
FEATURE               Location/Qualifiers
REGION                1..21
                      note = Synthetic
source                1..21
                      mol_type = protein
                      organism = synthetic construct
SEQUENCE: 56
AKEMVYYDIL TGYHNYYGMD V                                                        21

SEQ ID NO: 57         moltype = DNA  length = 324
FEATURE               Location/Qualifiers
misc_feature          1..324
                      note = Synthetic
source                1..324
                      mol_type = other DNA
                      organism = synthetic construct
SEQUENCE: 57
gacatcgtga tgacccagtc tccatcctca ctgtctgcat ctgtaggaga cagagtcacc  60
atcacttgtc gggcgagtca gggcattaac aattatttag cctggtttca gcagaaacca  120
gggaaagccc ctaagtccct gatccatact gcatccagtt tgcaaagtgg ggtcccatca  180
aagttcagcg gcagtggatc tgggacagat ttcactctca ccatcagcag cctgcagcct  240
gaagattttg caacttatta ctgccaacag tataatactt accctctcac tttcggcgga  300
gggaccaaag tggagatcaa acga                                                    324

SEQ ID NO: 58         moltype = AA  length = 108
FEATURE               Location/Qualifiers
REGION                1..108
                      note = Synthetic
source                1..108
                      mol_type = protein
                      organism = synthetic construct
SEQUENCE: 58
DIVMTQSPSS LSASVGDRVT ITCRASQGIN NYLAWFQQKP GKAPKSLIHT ASSLQSGVPS  60
KFSGSGSGTD FTLTISSLQP EDFATYYCQQ YNTYPLTFGG GTKVEIKR                          108

SEQ ID NO: 59         moltype = DNA  length = 18
FEATURE               Location/Qualifiers
misc_feature          1..18
                      note = Synthetic
source                1..18
                      mol_type = other DNA
                      organism = synthetic construct
SEQUENCE: 59
cagggcatta acaattat                                                           18

SEQ ID NO: 60         moltype = AA  length = 6
FEATURE               Location/Qualifiers
REGION                1..6
```

-continued

```
                          note = Synthetic
source                    1..6
                          mol_type = protein
                          organism = synthetic construct
SEQUENCE: 60
QGINNY                                                                6

SEQ ID NO: 61             moltype =   length =
SEQUENCE: 61
000

SEQ ID NO: 62             moltype =   length =
SEQUENCE: 62
000

SEQ ID NO: 63             moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 63
caacagtata atacttaccc tctcact                                         27

SEQ ID NO: 64             moltype = AA  length = 9
FEATURE                   Location/Qualifiers
REGION                    1..9
                          note = Synthetic
source                    1..9
                          mol_type = protein
                          organism = synthetic construct
SEQUENCE: 64
QQYNTYPLT                                                             9

SEQ ID NO: 65             moltype = DNA  length = 381
FEATURE                   Location/Qualifiers
misc_feature              1..381
                          note = Synthetic
source                    1..381
                          mol_type = other DNA
                          organism = synthetic construct
SEQUENCE: 65
caggtgcagc tggtggagtc tggggggaggc gtggtccagc ctgggaggtc cctgagactc    60
tcctgtgcag cctctggatt caccttcagt agttatgaca tgcactgggt ccgccaggct   120
ccaggcaagg ggctggagtg ggtggcagtt atatcatctg atggacgtga taaatactat   180
gtagactccg tgaagggccg attcaccatc tccagagaca actccaagaa cacgctttat   240
ctgcaaatga acagcctgag agctgaggac acggctgttt attactgtgc gaaagagatg   300
gtgtattacg atattttgac tggttatcat aactactacg gtatggacgt ctggggccaa   360
gggaccacgg tcaccgtctc c                                             381

SEQ ID NO: 66             moltype = AA  length = 127
FEATURE                   Location/Qualifiers
REGION                    1..127
                          note = Synthetic
source                    1..127
                          mol_type = protein
                          organism = synthetic construct
SEQUENCE: 66
QVQLVESGGG VVQPGRSLRL SCAASGFTFS SYDMHWVRQA PGKGLEWVAV ISSDGRDKYY    60
VDSVKGRFTI SRDNSKNTLY LQMNSLRAED TAVYYCAKEM VYYDILTGYH NYYGMDVWGQ   120
GTTVTVS                                                             127

SEQ ID NO: 67             moltype = DNA  length = 321
FEATURE                   Location/Qualifiers
misc_feature              1..321
                          note = Synthetic
source                    1..321
                          mol_type = other DNA
                          organism = synthetic construct
SEQUENCE: 67
gacatccaga tgacccagtc tccatcctca ctgtctgcat ctgtaggaga cagagtcacc    60
atcacttgtc gggcgagtca gggcattaac aattatttag cctggtttca gcagaaacca   120
gggaaagccc ctaagtccct gatccatact gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatactt accctctcac tttcggcgga   300
gggaccaagg tggagatcaa a                                             321

SEQ ID NO: 68             moltype = AA  length = 107
```

-continued

```
FEATURE              Location/Qualifiers
REGION               1..107
                     note = Synthetic
source               1..107
                     mol_type = protein
                     organism = synthetic construct
SEQUENCE: 68
DIQMTQSPSS LSASVGDRVT ITCRASQGIN NYLAWFQQKP GKAPKSLIHT ASSLQSGVPS    60
KFSGSGSGTD FTLTISSLQP EDFATYYCQQ YNTYPLTFGG GTKVEIK                 107

SEQ ID NO: 69        moltype = DNA   length = 384
FEATURE              Location/Qualifiers
misc_feature         1..384
                     note = Synthetic
source               1..384
                     mol_type = other DNA
                     organism = synthetic construct
SEQUENCE: 69
caggtgcagc tggtgcagtc tggggggaggc ttggtccagc ctggggggtc cctgagactc    60
tcctgtgcag cctccggatt cacctttagt aactatttga tgaactgggt ccgccaggct   120
ccagggaagg ggctggagtg gctggccaac atacaggaag atggaattga gaaatactat   180
gtggactctg tgaagggccg attcaccatc tccagagaca acgccaagaa ctcactgtat   240
ctgcaaatga acagcctgag agccgaggac acggctgtgt attactgtgc gagagagccc   300
tcccattacg atattttgac tggttatgac tactattacg gtatggacgt ctggggccaa   360
gggaccacgg tcaccgtctc ctca                                         384

SEQ ID NO: 70        moltype = AA   length = 128
FEATURE              Location/Qualifiers
REGION               1..128
                     note = Synthetic
source               1..128
                     mol_type = protein
                     organism = synthetic construct
SEQUENCE: 70
QVQLVQSGGG LVQPGGSLRL SCAASGFTFS NYLMNWVRQA PGKGLEWLAN IQEDGIEKYY    60
VDSVKGRFTI SRDNAKNSLY LQMNSLRAED TAVYYCAREP SHYDILTGYD YYYGMDVWGQ   120
GTTVTVSS                                                           128

SEQ ID NO: 71        moltype = DNA   length = 24
FEATURE              Location/Qualifiers
misc_feature         1..24
                     note = Synthetic
source               1..24
                     mol_type = other DNA
                     organism = synthetic construct
SEQUENCE: 71
ggattcacct ttagtaacta tttg                                          24

SEQ ID NO: 72        moltype = AA   length = 8
FEATURE              Location/Qualifiers
REGION               1..8
                     note = Synthetic
source               1..8
                     mol_type = protein
                     organism = synthetic construct
SEQUENCE: 72
GFTFSNYL                                                             8

SEQ ID NO: 73        moltype = DNA   length = 24
FEATURE              Location/Qualifiers
misc_feature         1..24
                     note = Synthetic
source               1..24
                     mol_type = other DNA
                     organism = synthetic construct
SEQUENCE: 73
atacaggaag atggaattga gaaa                                          24

SEQ ID NO: 74        moltype = AA   length = 8
FEATURE              Location/Qualifiers
REGION               1..8
                     note = Synthetic
source               1..8
                     mol_type = protein
                     organism = synthetic construct
SEQUENCE: 74
IQEDGIEK                                                             8

SEQ ID NO: 75        moltype = DNA   length = 63
```

-continued

```
FEATURE                 Location/Qualifiers
misc_feature            1..63
                        note = Synthetic
source                  1..63
                        mol_type = other DNA
                        organism = synthetic construct
SEQUENCE: 75
gcgagagagc cctcccatta cgatattttg actggttatg actactatta cggtatggac   60
gtc                                                                63

SEQ ID NO: 76           moltype = AA  length = 21
FEATURE                 Location/Qualifiers
REGION                  1..21
                        note = Synthetic
source                  1..21
                        mol_type = protein
                        organism = synthetic construct
SEQUENCE: 76
AREPSHYDIL TGYDYYYGMD V                                             21

SEQ ID NO: 77           moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 77
gacatccagt tgacccagtc tccatcctcc ctgtctgcat ctgtaggaga cagagtcacc   60
atcacttgcc gggcaagtca gggcattaga aatgatttag ctggtatca gcagaaacca  120
gggaaagccc ctaagcgcct gatctatgct gcatccagtt tgcaaagtgg ggtcccatca  180
aggttcagcg gcagtggatc tgggacagaa ttcattctca cagtcagcag cctgcagcct  240
gaagactttg caacttatta ctgtctacag tataatagta acccattcac tttcggccct  300
gggaccaagg tggagatcaa acga                                        324

SEQ ID NO: 78           moltype = AA  length = 108
FEATURE                 Location/Qualifiers
REGION                  1..108
                        note = Synthetic
source                  1..108
                        mol_type = protein
                        organism = synthetic construct
SEQUENCE: 78
DIQLTQSPSS LSASVGDRVT ITCRASQGIR NDLGWYQQKP GKAPKRLIYA ASSLQSGVPS   60
RFSGSGSGTE FILTVSSLQP EDFATYYCLQ YNSNPFTFGP GTKVEIKR              108

SEQ ID NO: 79           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 79
cagggcatta gaaatgat                                                18

SEQ ID NO: 80           moltype = AA  length = 6
FEATURE                 Location/Qualifiers
REGION                  1..6
                        note = Synthetic
source                  1..6
                        mol_type = protein
                        organism = synthetic construct
SEQUENCE: 80
QGIRND                                                              6

SEQ ID NO: 81           moltype =   length =
SEQUENCE: 81
000

SEQ ID NO: 82           moltype =   length =
SEQUENCE: 82
000

SEQ ID NO: 83           moltype = DNA  length = 27
FEATURE                 Location/Qualifiers
misc_feature            1..27
                        note = Synthetic
source                  1..27
```

-continued

```
                        mol_type = other DNA
                        organism = synthetic construct
SEQUENCE: 83
ctacagtata atagtaaccc attcact                                           27

SEQ ID NO: 84          moltype = AA   length = 9
FEATURE                Location/Qualifiers
REGION                 1..9
                       note = Synthetic
source                 1..9
                       mol_type = protein
                       organism = synthetic construct
SEQUENCE: 84
LQYNSNPFT                                                                9

SEQ ID NO: 85          moltype = DNA   length = 381
FEATURE                Location/Qualifiers
misc_feature           1..381
                       note = Synthetic
source                 1..381
                       mol_type = other DNA
                       organism = synthetic construct
SEQUENCE: 85
gaggtgcagc tggtggagtc tggggaggc ttggtccagc ctgggggtc cctgagactc        60
tcctgtgcag cctccggatt cacctttagt aactatttga tgaactgggt ccgccaggct      120
ccaggggaagg ggctggaagtg gctggccaac atacaggaag atggaattga gaaatactat    180
gtggactctg tgaagggccg attcaccatc tccagagaca acgccaagaa ctcactgtat       240
ctgcaaatga acagcctgag agccgaggac acggctgtgt attactgtgc gagagagccc       300
tcccattacg atattttgac tggttatgac tactattacg gtatggacgt ctggggccaa       360
gggaccacgg tcaccgtctc c                                                 381

SEQ ID NO: 86          moltype = AA   length = 127
FEATURE                Location/Qualifiers
REGION                 1..127
                       note = Synthetic
source                 1..127
                       mol_type = protein
                       organism = synthetic construct
SEQUENCE: 86
EVQLVESGGG LVQPGGSLRL SCAASGFTFS NYLMNWVRQA PGKGLEWLAN IQEDGIEKYY        60
VDSVKGRFTI SRDNAKNSLY LQMNSLRAED TAVYYCAREP SHYDILTGYD YYYGMDVWGQ       120
GTTVTVS                                                                 127

SEQ ID NO: 87          moltype = DNA   length = 321
FEATURE                Location/Qualifiers
misc_feature           1..321
                       note = Synthetic
source                 1..321
                       mol_type = other DNA
                       organism = synthetic construct
SEQUENCE: 87
gacatccaga tgacccagtc tccatcctcc ctgtctgcat ctgtaggaga cagagtcacc        60
atcacttgcc gggcaagtca gggcattaga aatgatttag ctggtatca gcagaaacca        120
gggaaagccc ctaagcgcct gatctatgct gcatccagtt tgcaaagtgg ggtcccatca       180
aggttcagcg gcagtggatc tgggacagaa ttcattctca cagtcagcag cctgcagcct       240
gaagactttg caacttatta ctgtctacag tataatagta acccattcac tttcggccct       300
gggaccaaag tggatatcaa a                                                 321

SEQ ID NO: 88          moltype = AA   length = 107
FEATURE                Location/Qualifiers
REGION                 1..107
                       note = Synthetic
source                 1..107
                       mol_type = protein
                       organism = synthetic construct
SEQUENCE: 88
DIQMTQSPSS LSASVGDRVT ITCRASQGIR NDLGWYQQKP GKAPKRLIYA ASSLQSGVPS        60
RFSGSGSGTE FILTVSSLQP EDFATYYCLQ YNSNPFTFGP GTKVDIK                     107

SEQ ID NO: 89          moltype = DNA   length = 381
FEATURE                Location/Qualifiers
misc_feature           1..381
                       note = Synthetic
source                 1..381
                       mol_type = other DNA
                       organism = synthetic construct
SEQUENCE: 89
gaggtgcagc tggtgcagtc tggggagcc ttggtacagc ctggggggtc cctgagactc         60
tcctgtacag cctctggttt caccttcagt aactacgaca tgcactgggt ccgccaaact      120
```

-continued

```
acaggaaaag gtctggagtg gatctcagct attgatactg ctggtgacac atactatcca   180
ggctccgtga agggccgatt caccgtctcc agagaaaatg ccaagaactc cttttatctt   240
caaatgaaca gcctgagagc cggggacacg gctgtgtatt actgtgcaag ggaggggaag   300
tattacgata ttttgactgg tgactaccac tactacggta tggacgtctg gggccaaggg   360
accacggtca ccgtctcctc a                                             381

SEQ ID NO: 90             moltype = AA  length = 127
FEATURE                   Location/Qualifiers
REGION                    1..127
                          note = Synthetic
source                    1..127
                          mol_type = protein
                          organism = synthetic construct
SEQUENCE: 90
EVQLVQSGGA LVQPGGSLRL SCTASGFTFS NYDMHWVRQT TGKGLEWISA IDTAGDTYYP   60
GSVKGRFTVS RENAKNSFYL QMNSLRAGDT AVYYCAREGK YYDILTGDYH YYGMDVWGQG   120
TTVTVSS                                                             127

SEQ ID NO: 91             moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 91
ggtttcacct tcagtaacta cgac                                          24

SEQ ID NO: 92             moltype = AA  length = 8
FEATURE                   Location/Qualifiers
REGION                    1..8
                          note = Synthetic
source                    1..8
                          mol_type = protein
                          organism = synthetic construct
SEQUENCE: 92
GFTFSNYD                                                            8

SEQ ID NO: 93             moltype = DNA  length = 21
FEATURE                   Location/Qualifiers
misc_feature              1..21
                          note = Synthetic
source                    1..21
                          mol_type = other DNA
                          organism = synthetic construct
SEQUENCE: 93
attgatactg ctggtgacac a                                             21

SEQ ID NO: 94             moltype = AA  length = 7
FEATURE                   Location/Qualifiers
REGION                    1..7
                          note = Synthetic
source                    1..7
                          mol_type = protein
                          organism = synthetic construct
SEQUENCE: 94
IDTAGDT                                                             7

SEQ ID NO: 95             moltype = DNA  length = 63
FEATURE                   Location/Qualifiers
misc_feature              1..63
                          note = Synthetic
source                    1..63
                          mol_type = other DNA
                          organism = synthetic construct
SEQUENCE: 95
gcaagggagg ggaagtatta cgatattttg actggtgact accactacta cggtatggac   60
gtc                                                                 63

SEQ ID NO: 96             moltype = AA  length = 21
FEATURE                   Location/Qualifiers
REGION                    1..21
                          note = Synthetic
source                    1..21
                          mol_type = protein
                          organism = synthetic construct
SEQUENCE: 96
AREGKYYDIL TGDYHYYGMD V                                             21
```

```
SEQ ID NO: 97            moltype = DNA   length = 324
FEATURE                  Location/Qualifiers
misc_feature             1..324
                         note = Synthetic
source                   1..324
                         mol_type = other DNA
                         organism = synthetic construct
SEQUENCE: 97
gccatccgga tgacccagtc tccatcctcc ctgtctgcat ctgtaggaga cagagtcacc   60
atcacttgtc gggcaagtca gggcattaga aatgatttag gctggtatca gcagaaacca  120
gggaaagccc ctaagcgact gatctatgct acatccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgctcac tttcggcgga  300
gggaccaagg tggaaatcaa acga                                         324

SEQ ID NO: 98            moltype = AA   length = 108
FEATURE                  Location/Qualifiers
REGION                   1..108
                         note = Synthetic
source                   1..108
                         mol_type = protein
                         organism = synthetic construct
SEQUENCE: 98
AIRMTQSPSS LSASVGDRVT ITCRASQGIR NDLGWYQQKP GKAPKRLIYA TSSLQSGVPS   60
RFSGSGSGTE FTLTISSLQP EDFATYYCLQ HNSYPLTFGG GTKVEIKR               108

SEQ ID NO: 99            moltype = DNA   length = 18
FEATURE                  Location/Qualifiers
misc_feature             1..18
                         note = Synthetic
source                   1..18
                         mol_type = other DNA
                         organism = synthetic construct
SEQUENCE: 99
cagggcatta gaaatgat                                                 18

SEQ ID NO: 100           moltype = AA   length = 6
FEATURE                  Location/Qualifiers
REGION                   1..6
                         note = Synthetic
source                   1..6
                         mol_type = protein
                         organism = synthetic construct
SEQUENCE: 100
QGIRND                                                              6

SEQ ID NO: 101           moltype =    length =
SEQUENCE: 101
000

SEQ ID NO: 102           moltype =    length =
SEQUENCE: 102
000

SEQ ID NO: 103           moltype = DNA   length = 27
FEATURE                  Location/Qualifiers
misc_feature             1..27
                         note = Synthetic
source                   1..27
                         mol_type = other DNA
                         organism = synthetic construct
SEQUENCE: 103
ctacagcata atagttaccc gctcact                                      27

SEQ ID NO: 104           moltype = AA   length = 9
FEATURE                  Location/Qualifiers
REGION                   1..9
                         note = Synthetic
source                   1..9
                         mol_type = protein
                         organism = synthetic construct
SEQUENCE: 104
LQHNSYPLT                                                           9

SEQ ID NO: 105           moltype = DNA   length = 378
FEATURE                  Location/Qualifiers
misc_feature             1..378
                         note = Synthetic
source                   1..378
```

```
                         mol_type = other DNA
                         organism = synthetic construct
SEQUENCE: 105
gaggtgcagc tggtggagtc tgggggagcc ttggtacagc ctggggggtc cctgagactc    60
tcctgtacag cctctggttt caccttcagt aactacgaca tgcactgggt ccgccaaact   120
acaggaaaag gtctggagtg gatctcagct attgatactg ctggtgacac atactatcca   180
ggctccgtga agggccgatt caccgtctcc agagaaaatg ccaagaactc cttttatctt   240
caaatgaaca gcctgagagc cggggacacg gctgtgtatt actgtgcaag ggaggggaag   300
tattacgata tttttgactgg tgactaccac tactacggta tggacgtctg gggccaaggg   360
accacggtca ccgtctcc                                                  378

SEQ ID NO: 106          moltype = AA  length = 126
FEATURE                 Location/Qualifiers
REGION                  1..126
                        note = Synthetic
source                  1..126
                        mol_type = protein
                        organism = synthetic construct
SEQUENCE: 106
EVQLVESGGA LVQPGGSLRL SCTASGFTFS NYDMHWVRQT TGKGLEWISA IDTAGDTYYP    60
GSVKGRFTVS RENAKNSFYL QMNSLRAGDT AVYYCAREGK YYDILTGDYH YYGMDVWGQG   120
TTVTVS                                                              126

SEQ ID NO: 107          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 107
gacatccaga tgacccagtc tccatcctcc ctgtctgcat ctgtaggaga cagagtcacc    60
atcacttgtc gggcaagtca gggcattaga aatgatttag ctggtatca gcagaaacca   120
gggaaagccc ctaagcgact gatctatgct acatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgctcac tttcggcgga   300
gggaccaagc tggagatcaa a                                             321

SEQ ID NO: 108          moltype = AA  length = 107
FEATURE                 Location/Qualifiers
REGION                  1..107
                        note = Synthetic
source                  1..107
                        mol_type = protein
                        organism = synthetic construct
SEQUENCE: 108
DIQMTQSPSS LSASVGDRVT ITCRASQGIR NDLGWYQQKP GKAPKRLIYA TSSLQSGVPS    60
RFSGSGSGTE FTLTISSLQP EDFATYYCLQ HNSYPLTFGG GTKLEIK                 107

SEQ ID NO: 109          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 109
caggtgcagc tggtgcagtc tgggggaggc gtggtccagc ctgggaggtc cctgagactc    60
tcctgtgcag cgtctgggtt caccttagt aactttggca tgcactgggt ccgccaggct   120
ccaggcaagg ggctggagtg ggtggcagtt atatggtttg atgaaattga taaatactat   180
gcagactccg tgaagggccg attcaccatc tccagagaca attccaagaa cacgctgtat   240
ccgcaaatga acagcctgag agccgaagac acggctgtgt attactgtgc gcgagaagat   300
tacgatattt tgactggtta ctattacgct atggacgtct ggggccaagg gaccacggtc   360
accgtctcct ca                                                      372

SEQ ID NO: 110          moltype = AA  length = 124
FEATURE                 Location/Qualifiers
REGION                  1..124
                        note = Synthetic
source                  1..124
                        mol_type = protein
                        organism = synthetic construct
SEQUENCE: 110
QVQLVQSGGG VVQPGRSLRL SCAASGFTFS NFGMHWVRQA PGKGLEWVAV IWFDEIDKYY    60
ADSVKGRFTI SRDNSKNTLY PQMNSLRAED TAVYYCARED YDILTGYYYA MDVWGQGTTV   120
TVSS                                                               124

SEQ ID NO: 111          moltype = DNA  length = 24
FEATURE                 Location/Qualifiers
```

-continued

```
misc_feature            1..24
                        note = Synthetic
source                  1..24
                        mol_type = other DNA
                        organism = synthetic construct
SEQUENCE: 111
gggttcacct ttagtaactt tggc                                24

SEQ ID NO: 112          moltype = AA  length = 8
FEATURE                 Location/Qualifiers
REGION                  1..8
                        note = Synthetic
source                  1..8
                        mol_type = protein
                        organism = synthetic construct
SEQUENCE: 112
GFTFSNFG                                                   8

SEQ ID NO: 113          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 113
atatggtttg atgaaattga taaa                                24

SEQ ID NO: 114          moltype = AA  length = 8
FEATURE                 Location/Qualifiers
REGION                  1..8
                        note = Synthetic
source                  1..8
                        mol_type = protein
                        organism = synthetic construct
SEQUENCE: 114
IWFDEIDK                                                   8

SEQ ID NO: 115          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 115
gcgcgagaag attacgatat tttgactggt tactattacg ctatggacgt c   51

SEQ ID NO: 116          moltype = AA  length = 17
FEATURE                 Location/Qualifiers
REGION                  1..17
                        note = Synthetic
source                  1..17
                        mol_type = protein
                        organism = synthetic construct
SEQUENCE: 116
AREDYDILTG YYYAMDV                                         17

SEQ ID NO: 117          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 117
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct aatctatgct gcatcccgtt tgcaaagtgg ggtccccatcg  180
aggttcagcg gcagtggatc tgggacagaa ttcactctca caatcagcag cctgcagcct  240
gaagattttg aacttatta ctgtctacag cataatagtc accccaccct cggccaaggg  300
accaaggtgg agatcaaacg a                                    321

SEQ ID NO: 118          moltype = AA  length = 107
FEATURE                 Location/Qualifiers
REGION                  1..107
                        note = Synthetic
source                  1..107
                        mol_type = protein
```

-continued

```
                     organism = synthetic construct
SEQUENCE: 118
DIQMTQSPSS LSASVGDRVT ITCRASQGIR NDLGWYQQKP GKAPKRLIYA ASRLQSGVPS  60
RFSGSGSGTE FTLTISSLQP EDFGTYYCLQ HNSHPTFGQG TKVEIKR                107

SEQ ID NO: 119        moltype = DNA  length = 18
FEATURE               Location/Qualifiers
misc_feature          1..18
                      note = Synthetic
source                1..18
                      mol_type = other DNA
                      organism = synthetic construct
SEQUENCE: 119
cagggcatta gaaatgat                                                18

SEQ ID NO: 120        moltype = AA  length = 6
FEATURE               Location/Qualifiers
REGION                1..6
                      note = Synthetic
source                1..6
                      mol_type = protein
                      organism = synthetic construct
SEQUENCE: 120
QGIRND                                                             6

SEQ ID NO: 121        moltype =   length =
SEQUENCE: 121
000

SEQ ID NO: 122        moltype =   length =
SEQUENCE: 122
000

SEQ ID NO: 123        moltype = DNA  length = 24
FEATURE               Location/Qualifiers
misc_feature          1..24
                      note = Synthetic
source                1..24
                      mol_type = other DNA
                      organism = synthetic construct
SEQUENCE: 123
ctacagcata atagtcaccc cacc                                         24

SEQ ID NO: 124        moltype = AA  length = 8
FEATURE               Location/Qualifiers
REGION                1..8
                      note = Synthetic
source                1..8
                      mol_type = protein
                      organism = synthetic construct
SEQUENCE: 124
LQHNSHPT                                                           8

SEQ ID NO: 125        moltype = DNA  length = 369
FEATURE               Location/Qualifiers
misc_feature          1..369
                      note = Synthetic
source                1..369
                      mol_type = other DNA
                      organism = synthetic construct
SEQUENCE: 125
caggtgcagc tggtggagtc tggggggaggc gtggtccagc ctgggaggtc cctgagactc  60
tcctgtgcag cgtctgggtt cacctttagt aactttggca tgcactgggt ccgccaggct  120
ccaggcaagg ggctggagtg ggtggcagtt atatggtttg atgaaattga taaatactat  180
gcagactccg tgaagggccg attcaccatc tccagagaca attccaagaa cacgctgtat  240
ccgcaaatga acagcctgag agccgaagac acggctgtgt attactgtgc gcgagaagat  300
tacgatattt tgactggtta ctattacgct atggacgtct ggggccaagg gaccacggtc  360
accgtctcc                                                         369

SEQ ID NO: 126        moltype = AA  length = 123
FEATURE               Location/Qualifiers
REGION                1..123
                      note = Synthetic
source                1..123
                      mol_type = protein
                      organism = synthetic construct
SEQUENCE: 126
QVQLVESGGG VVQPGRSLRL SCAASGFTFS NFGMHWVRQA PGKGLEWVAV IWFDEIDKYY  60
ADSVKGRFTI SRDNSKNTLY PQMNSLRAED TAVYYCARED YDILTGYYYA MDVWGQGTTV  120
```

-continued

```
TVS                                                                  123

SEQ ID NO: 127          moltype = DNA   length = 318
FEATURE                 Location/Qualifiers
misc_feature            1..318
                        note = Synthetic
source                  1..318
                        mol_type = other DNA
                        organism = synthetic construct
SEQUENCE: 127
gacatccaga tgacccagtc tccatcctcc ctgtctgcat ctgtaggaga cagagtcacc   60
atcacttgcc gggcaagtca gggcattaga aatgatttag ctggtatca gcagaaacca   120
gggaaagccc ctaagcgcct aatctatgct gcatcccgtt tgcaaagtgg ggtcccatcg   180
aggttcagcg gcagtggatc tgggacagaa ttcactctca caatcagcag cctgcagcct   240
gaagattttg gaacttatta ctgtctacag cataatagtc accccacctt cggccaaggg   300
accaaggtgg agatcaaa                                                  318

SEQ ID NO: 128          moltype = AA   length = 106
FEATURE                 Location/Qualifiers
REGION                  1..106
                        note = Synthetic
source                  1..106
                        mol_type = protein
                        organism = synthetic construct
SEQUENCE: 128
DIQMTQSPSS LSASVGDRVT ITCRASQGIK NDLGWYQQKP GKAPKRLIYA ASRLQSGVPS   60
RFSGSGSGTE FTLTISSLQP EDFGTYYCLQ HNSHPTFGQG TKVEIK                   106

SEQ ID NO: 129          moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 129
gaggtgcagc tggtggagtc ggggggaggc atggtacagc ctggggggtc cctgagactc   60
tcctgtgcag cctctggatt cacctccagt aactacgaca tgcactgggt ccgccaagct   120
acaggaaaag gtctggagtg ggtctcaagt attgatactg ctggggacac ttactatcca   180
gactccgtga agggccgctt tatcatctcc agagaaaatg ccaaaaactc cctgtatctt   240
caaatgaata gcctgagagc cggggacacg gctgtgtatt actgtacaag ggagccccga   300
aattacgaaa ttttgactgg tcactaccac taccacggta tggacatctg gggccaaggg   360
accacggtca ccgtctcctc a                                             381

SEQ ID NO: 130          moltype = AA   length = 127
FEATURE                 Location/Qualifiers
REGION                  1..127
                        note = Synthetic
source                  1..127
                        mol_type = protein
                        organism = synthetic construct
SEQUENCE: 130
EVQLVESGGG MVQPGGSLRL SCAASGFTSS NYDMHWVRQA TGKGLEWVSS IDTAGDTYYP   60
DSVKGRFIIS RENAKNSLYL QMNSLRAGDT AVYYCTREPR NYEILTGHYH YHGMDIWGQG   120
TTVTVSS                                                              127

SEQ ID NO: 131          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 131
ggattcacct ccagtaacta cgac                                          24

SEQ ID NO: 132          moltype = AA   length = 8
FEATURE                 Location/Qualifiers
REGION                  1..8
                        note = Synthetic
source                  1..8
                        mol_type = protein
                        organism = synthetic construct
SEQUENCE: 132
GFTSSNYD                                                             8

SEQ ID NO: 133          moltype = DNA   length = 21
FEATURE                 Location/Qualifiers
misc_feature            1..21
```

-continued

```
                           note = Synthetic
source                     1..21
                           mol_type = other DNA
                           organism = synthetic construct
SEQUENCE: 133
attgatactg ctggggacac t                                     21

SEQ ID NO: 134            moltype = AA   length = 7
FEATURE                   Location/Qualifiers
REGION                    1..7
                          note = Synthetic
source                    1..7
                          mol_type = protein
                          organism = synthetic construct
SEQUENCE: 134
IDTAGDT                                                       7

SEQ ID NO: 135            moltype = DNA  length = 63
FEATURE                   Location/Qualifiers
misc_feature              1..63
                          note = Synthetic
source                    1..63
                          mol_type = other DNA
                          organism = synthetic construct
SEQUENCE: 135
acaagggagc cccgaaatta cgaaattttg actggtcact accactacca cggtatggac  60
atc                                                               63

SEQ ID NO: 136            moltype = AA   length = 21
FEATURE                   Location/Qualifiers
REGION                    1..21
                          note = Synthetic
source                    1..21
                          mol_type = protein
                          organism = synthetic construct
SEQUENCE: 136
TREPRNYEIL TGHYHYHGMD I                                       21

SEQ ID NO: 137            moltype = DNA  length = 324
FEATURE                   Location/Qualifiers
misc_feature              1..324
                          note = Synthetic
source                    1..324
                          mol_type = other DNA
                          organism = synthetic construct
SEQUENCE: 137
gacatccaga tgacccagtc gccatcctcc ctgtctgcat ctgtaggaga cagagtcacc  60
atcacttgcc gggcaagtca ggccattaga aatgatttag ctggtatca gcagaaacca  120
gggaaagccc ctaaactcct gatctatact gcattcagtt tacagagtgg ggtcccatca  180
aggttcagcg gcagtaaatc tggcacagac ttcactctca ccatcagcag cctgcagcct  240
gaaagatttg cgacttatta ctgtctgcag gattacacta tcctcggac gttcggccaa  300
gggaccaagg tggagatcaa acga                                       324

SEQ ID NO: 138            moltype = AA   length = 108
FEATURE                   Location/Qualifiers
REGION                    1..108
                          note = Synthetic
source                    1..108
                          mol_type = protein
                          organism = synthetic construct
SEQUENCE: 138
DIQMTQSPSS LSASVGDRVT ITCRASQAIR NDLGWYQQKP GKAPKLLIYT AFSLQSGVPS  60
RFSGSKSGTD FTLTISSLQP EDFATYYCLQ DYTNPRTFGQ GTKVEIKR               108

SEQ ID NO: 139            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 139
caggccatta gaaatgat                                          18

SEQ ID NO: 140            moltype = AA   length = 6
FEATURE                   Location/Qualifiers
REGION                    1..6
                          note = Synthetic
source                    1..6
```

-continued

```
                          mol_type = protein
                          organism = synthetic construct
SEQUENCE: 140
QAIRND                                                          6

SEQ ID NO: 141            moltype =   length =
SEQUENCE: 141
000

SEQ ID NO: 142            moltype =   length =
SEQUENCE: 142
000

SEQ ID NO: 143            moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 143
ctgcaggatt acactaatcc tcggacg                                  27

SEQ ID NO: 144            moltype = AA  length = 9
FEATURE                   Location/Qualifiers
REGION                    1..9
                          note = Synthetic
source                    1..9
                          mol_type = protein
                          organism = synthetic construct
SEQUENCE: 144
LQDYTNPRT                                                       9

SEQ ID NO: 145            moltype = DNA  length = 378
FEATURE                   Location/Qualifiers
misc_feature              1..378
                          note = Synthetic
source                    1..378
                          mol_type = other DNA
                          organism = synthetic construct
SEQUENCE: 145
gaggtgcagc tggtggagtc ggggggaggc atggtacagc ctggggggtc cctgagactc   60
tcctgtgcag cctctggatt cacctccagt aactacgaca tgcactgggt ccgccaagct  120
acaggaaaag gtctggagtg ggtctcaagt attgatactg ctggggacac ttactatcca  180
gactccgtga agggccgctt tatcatctcc agagaaaatg ccaaaaactc cctgtatctt  240
caaatgaata gcctgagagc cggggacacg gctgtgtatt actgtacaag ggagccccga  300
aattacgaaa ttttgactgg tcactaccac taccacggta tggacatctg gggccaaggg  360
accacggtca ccgtctcc                                               378

SEQ ID NO: 146            moltype = AA  length = 126
FEATURE                   Location/Qualifiers
REGION                    1..126
                          note = Synthetic
source                    1..126
                          mol_type = protein
                          organism = synthetic construct
SEQUENCE: 146
EVQLVESGGG MVQPGGSLRL SCAASGFTSS NYDMHWVRQA TGKGLEWVSS IDTAGDTYYP   60
DSVKGRFIIS RENAKNSLYL QMNSLRAGDT AVYYCTREPR NYEILTGHYH YHGMDIWGQG  120
TTVTVS                                                             126

SEQ ID NO: 147            moltype = DNA  length = 321
FEATURE                   Location/Qualifiers
misc_feature              1..321
                          note = Synthetic
source                    1..321
                          mol_type = other DNA
                          organism = synthetic construct
SEQUENCE: 147
gccatccaga tgacccagtc gccatcctcc ctgtctgcat ctgtaggaga cagagtcacc   60
atcacttgcc gggcaagtca ggccattaga aatgatttag ctggtatca gcagaaacca  120
gggaaagccc ctaaactcct gatctatact gcattcagtt tacagagtgg ggtcccatca  180
aggttcagcg gcagtaaatc tggcacagac ttcactctca ccatcagcag cctgcagcct  240
gaagattttg cgacttatta ctgtctgcag gattacacta atcctcggac gttcggccaa  300
gggaccaagg tggaaatcaa a                                            321

SEQ ID NO: 148            moltype = AA  length = 107
FEATURE                   Location/Qualifiers
REGION                    1..107
```

```
                        note = Synthetic
source                  1..107
                        mol_type = protein
                        organism = synthetic construct
SEQUENCE: 148
AIQMTQSPSS LSASVGDRVT ITCRASQAIR NDLGWYQQKP GKAPKLLIYT AFSLQSGVPS    60
RFSGSKSGTD FTLTISSLQP EDFATYYCLQ DYTNPRTFGQ GTKVEIK               107

SEQ ID NO: 149         moltype = DNA   length = 357
FEATURE                Location/Qualifiers
misc_feature           1..357
                       note = synthetic
source                 1..357
                       mol_type = other DNA
                       organism = synthetic construct
SEQUENCE: 149
caggtgcagc tggtggagtc tgggggaggc gtggtccagc ctgggaggtc cctgagactc    60
tcctgtgcag cctctggatt cgccttcagt aactatggga tgcactgggt ccgccaggct   120
ccaggcaagg ggctggaatg ggtgacattt atatcatatg atggaagtaa taaatactat   180
gcagactccg tgaagggccg attcaccatc tccagagaca attccaagaa cacgctgtat   240
ctgcaagtga acagcctgag agctgaggac acggctgtgt attactgtgc gaaagaagca   300
gtattagctg ccctctttga ctactggggc cagggaaccc tggtcaccgt ctcctca     357

SEQ ID NO: 150         moltype = AA   length = 119
FEATURE                Location/Qualifiers
REGION                 1..119
                       note = synthetic
source                 1..119
                       mol_type = protein
                       organism = synthetic construct
SEQUENCE: 150
QVQLVESGGG VVQPGRSLRL SCAASGFAFS NYGMHWVRQA PGKGLEWVTF ISYDGSNKYY    60
ADSVKGRFTI SRDNSKNTLY LQVNSLRAED TAVYYCAKEA VLAALFDYWG QGTLVTVSS    119

SEQ ID NO: 151         moltype = DNA   length = 24
FEATURE                Location/Qualifiers
misc_feature           1..24
                       note = synthetic
source                 1..24
                       mol_type = other DNA
                       organism = synthetic construct
SEQUENCE: 151
ggattcgcct tcagtaacta tggc                                           24

SEQ ID NO: 152         moltype = AA   length = 8
FEATURE                Location/Qualifiers
REGION                 1..8
                       note = synthetic
source                 1..8
                       mol_type = protein
                       organism = synthetic construct
SEQUENCE: 152
GFAFSNYG                                                               8

SEQ ID NO: 153         moltype = DNA   length = 24
FEATURE                Location/Qualifiers
misc_feature           1..24
                       note = synthetic
source                 1..24
                       mol_type = other DNA
                       organism = synthetic construct
SEQUENCE: 153
atatcatatg atggaagtaa taaa                                           24

SEQ ID NO: 154         moltype = AA   length = 8
FEATURE                Location/Qualifiers
REGION                 1..8
                       note = synthetic
source                 1..8
                       mol_type = protein
                       organism = synthetic construct
SEQUENCE: 154
ISYDGSNK                                                               8

SEQ ID NO: 155         moltype = DNA   length = 36
FEATURE                Location/Qualifiers
misc_feature           1..36
                       note = synthetic
source                 1..36
```

-continued

```
                        mol_type = other DNA
                        organism = synthetic construct
SEQUENCE: 155
gcgaaagaag cagtattagc tgccctcttt gactac                              36

SEQ ID NO: 156          moltype = AA  length = 12
FEATURE                 Location/Qualifiers
REGION                  1..12
                        note = synthetic
source                  1..12
                        mol_type = protein
                        organism = synthetic construct
SEQUENCE: 156
AKEAVLAALF DY                                                        12

SEQ ID NO: 157          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 157
gacatcgtga tgacccagtc tccagactcc ctggctgtgt ctctgggcga gagggccacc  60
atcaactgca agtccagcca gagtgtttta tacagctcca acaatcagaa ctacttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcaacagcc tgcaggctga agatgtggca gtttattact gtcagcaata ttatagtact  300
cctacgttcg gccaagggac caaggtggaa atcaaa                              336

SEQ ID NO: 158          moltype = AA  length = 112
FEATURE                 Location/Qualifiers
REGION                  1..112
                        note = synthetic
source                  1..112
                        mol_type = protein
                        organism = synthetic construct
SEQUENCE: 158
DIVMTQSPDS LAVSLGERAT INCKSSQSVL YSSNNQNYLA WYQQKPGQPP KLLIYWASTR  60
ESGVPDRFSG SGSGTDFTLT INSLQAEDVA VYYCQQYYST PTFGQGTKVE IK           112

SEQ ID NO: 159          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 159
cagagtgttt tatacagctc caacaatcag aactac                              36

SEQ ID NO: 160          moltype = AA  length = 12
FEATURE                 Location/Qualifiers
REGION                  1..12
                        note = synthetic
source                  1..12
                        mol_type = protein
                        organism = synthetic construct
SEQUENCE: 160
QSVLYSSNNQ NY                                                        12

SEQ ID NO: 161          moltype =   length =
SEQUENCE: 161
000

SEQ ID NO: 162          moltype =   length =
SEQUENCE: 162
000

SEQ ID NO: 163          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 163
cagcaatatt atagtactcc tacg                                           24
```

```
SEQ ID NO: 164          moltype = AA   length = 8
FEATURE                 Location/Qualifiers
REGION                  1..8
                        note = synthetic
source                  1..8
                        mol_type = protein
                        organism = synthetic construct
SEQUENCE: 164
QQYYSTPT                                                             8

SEQ ID NO: 165          moltype = DNA   length = 357
FEATURE                 Location/Qualifiers
misc_feature            1..357
                        note = synthetic
source                  1..357
                        mol_type = other DNA
                        organism = synthetic construct
SEQUENCE: 165
caggtgcagc tggtggagtc tgggggaggc gtggtccagc ctgggaggtc cctgagactc   60
tcctgtgcag cctctggatt cacgttcaat acctatggca tgcactgggt ccgccaggct  120
ccagtcaagg ggctggagtg ggtggcattt atatcaaatg ataagagtaa tacattctat  180
gcagactccg tgaagggccg attcaccatc tccagagaca attccaagaa cacgctgttt  240
ctggaaatga acagcctgac agctgaggac acggctgttt attactgtgc gaaagagtcc  300
attttagcag ccctctttga ctactggggc cagggaaccc tggtcactgt ctcctca     357

SEQ ID NO: 166          moltype = AA   length = 119
FEATURE                 Location/Qualifiers
REGION                  1..119
                        note = synthetic
source                  1..119
                        mol_type = protein
                        organism = synthetic construct
SEQUENCE: 166
QVQLVESGGG VVQPGRSLRL SCAASGFTFN TYGMHWVRQA PVKGLEWVAF ISNDKSNTFY   60
ADSVKGRFTI SRDNSKNTLF LEMNSLTAED TAVYYCAKES ILAALFDYWG QGTLVTVSS   119

SEQ ID NO: 167          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 167
ggattcacgt tcaataccta tggc                                          24

SEQ ID NO: 168          moltype = AA   length = 8
FEATURE                 Location/Qualifiers
REGION                  1..8
                        note = synthetic
source                  1..8
                        mol_type = protein
                        organism = synthetic construct
SEQUENCE: 168
GFTFNTYG                                                             8

SEQ ID NO: 169          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 169
atatcaaatg ataagagtaa taca                                          24

SEQ ID NO: 170          moltype = AA   length = 8
FEATURE                 Location/Qualifiers
REGION                  1..8
                        note = synthetic
source                  1..8
                        mol_type = protein
                        organism = synthetic construct
SEQUENCE: 170
ISNDKSNT                                                             8

SEQ ID NO: 171          moltype = DNA   length = 36
FEATURE                 Location/Qualifiers
misc_feature            1..36
```

-continued

```
                        note = synthetic
source                  1..36
                        mol_type = other DNA
                        organism = synthetic construct
SEQUENCE: 171
gcgaaagagt ccattttagc agccctcttt gactac                       36

SEQ ID NO: 172          moltype = AA  length = 12
FEATURE                 Location/Qualifiers
REGION                  1..12
                        note = synthetic
source                  1..12
                        mol_type = protein
                        organism = synthetic construct
SEQUENCE: 172
AKESILAALF DY                                                 12

SEQ ID NO: 173          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 173
gacatcgtga tgacccagtc tccagactcc ctggctgtgt ctctgggcga gagggccacc   60
atcaactgca agtccagcca gagtgtttta tacagctcca acaataagaa ttacttagct  120
tggtaccaac agaaaccaag acagcctctt aaactactca tttactgggc atctattcgg  180
gaatccgggg tccctgaccg attcagtggc agcgggtctg ggacagattt cactctcacc  240
atcagcagcc tgcaggctga agatgtggca gtttattact gtcagcaatt ttatagtgtt  300
cccacttttg gccaggggac caagctggag atcaaa                           336

SEQ ID NO: 174          moltype = AA  length = 112
FEATURE                 Location/Qualifiers
REGION                  1..112
                        note = synthetic
source                  1..112
                        mol_type = protein
                        organism = synthetic construct
SEQUENCE: 174
DIVMTQSPDS LAVSLGERAT INCKSSQSVL YSSNNKNYLA WYQQKPRQPL KLLIYWASIR   60
ESGVPDRFSG SGSGTDFTLT ISSLQAEDVA VYYCQQFYSV PTFGQGTKLE IK          112

SEQ ID NO: 175          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 175
cagagtgttt tatacagctc caacaataag aattac                       36

SEQ ID NO: 176          moltype = AA  length = 12
FEATURE                 Location/Qualifiers
REGION                  1..12
                        note = synthetic
source                  1..12
                        mol_type = protein
                        organism = synthetic construct
SEQUENCE: 176
QSVLYSSNNK NY                                                 12

SEQ ID NO: 177          moltype =   length =
SEQUENCE: 177
000

SEQ ID NO: 178          moltype =   length =
SEQUENCE: 178
000

SEQ ID NO: 179          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 179
```

-continued

```
cagcaatttt atagtgttcc cact                                        24

SEQ ID NO: 180          moltype = AA   length = 8
FEATURE                 Location/Qualifiers
REGION                  1..8
                        note = synthetic
source                  1..8
                        mol_type = protein
                        organism = synthetic construct
SEQUENCE: 180
QQFYSVPT                                                          8

SEQ ID NO: 181          moltype = DNA   length = 357
FEATURE                 Location/Qualifiers
misc_feature            1..357
                        note = synthetic
source                  1..357
                        mol_type = other DNA
                        organism = synthetic construct
SEQUENCE: 181
caggtgcagc tggtggagtc tgggggaggc gtggtccagc ctgggaggtc cctgagactc   60
tcctgtgcag cctctggatt cacgtttagt acctttggca tgcactgggt ccgccaggct  120
ccagtcaagg ggctggagtg ggtggctttt atatcaaatg ataagaataa taaattctat  180
gcagactccg tgaagggccg attcaccatc tccagagaca attccaggga cacgctatat  240
ctgcaaatga acagcctgac acctgaggac acggctgttt attactgtgc gaaagagtcc  300
attttagcag ccctctttga ctactggggc cagggaaccc tggtcaccgt ctcctca     357

SEQ ID NO: 182          moltype = AA   length = 119
FEATURE                 Location/Qualifiers
REGION                  1..119
                        note = synthetic
source                  1..119
                        mol_type = protein
                        organism = synthetic construct
SEQUENCE: 182
QVQLVESGGG VVQPGRSLRL SCAASGFTFS TFGMHWVRQA PVKGLEWVAF ISNDKNNKFY   60
ADSVKGRFTI SRDNSRDTLY LQMNSLTPED TAVYYCAKES ILAALFDYWG QGTLVTVSS   119

SEQ ID NO: 183          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 183
ggattcacgt ttagtacctt tggc                                        24

SEQ ID NO: 184          moltype = AA   length = 8
FEATURE                 Location/Qualifiers
REGION                  1..8
                        note = synthetic
source                  1..8
                        mol_type = protein
                        organism = synthetic construct
SEQUENCE: 184
GFTFSTFG                                                          8

SEQ ID NO: 185          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 185
atatcaaatg ataagaataa taaa                                        24

SEQ ID NO: 186          moltype = AA   length = 8
FEATURE                 Location/Qualifiers
REGION                  1..8
                        note = synthetic
source                  1..8
                        mol_type = protein
                        organism = synthetic construct
SEQUENCE: 186
ISNDKNNK                                                          8

SEQ ID NO: 187          moltype = DNA   length = 36
```

-continued

```
FEATURE                 Location/Qualifiers
misc_feature            1..36
                        note = synthetic
source                  1..36
                        mol_type = other DNA
                        organism = synthetic construct
SEQUENCE: 187
gcgaaagagt ccattttagc agccctcttt gactac                              36

SEQ ID NO: 188          moltype = AA  length = 12
FEATURE                 Location/Qualifiers
REGION                  1..12
                        note = synthetic
source                  1..12
                        mol_type = protein
                        organism = synthetic construct
SEQUENCE: 188
AKESILAALF DY                                                        12

SEQ ID NO: 189          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 189
gacatcgtga tgacccagtc tccagactcc ctggctgtgt ctctgggcga gagggccacc   60
atcaactgca agtccagcca gagtgtttta tacagctcca acaataaaaa ttacttagct  120
tggtaccagc agaaaccagg acagcctctt aaacttctca tttactgggc atctattcgg  180
gaatccgggg tccctgaccg attcagtggc agcgggtctg ggacagattt cactctcacc  240
atcagcagcc tgcaggctga agatgtggca gtttattact gtcagcaatt ttatactgtt  300
cccacttttg gcctggggac caagctggag atcaaa                            336

SEQ ID NO: 190          moltype = AA  length = 112
FEATURE                 Location/Qualifiers
REGION                  1..112
                        note = synthetic
source                  1..112
                        mol_type = protein
                        organism = synthetic construct
SEQUENCE: 190
DIVMTQSPDS LAVSLGERAT INCKSSQSVL YSSNNKNYLA WYQQKPGQPL KLLIYWASIR   60
ESGVPDRFSG SGSGTDFTLT ISSLQAEDVA VYYCQQFYTV PTFGLGTKLE IK          112

SEQ ID NO: 191          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 191
cagagtgttt tatacagctc caacaataaa aattac                              36

SEQ ID NO: 192          moltype = AA  length = 12
FEATURE                 Location/Qualifiers
REGION                  1..12
                        note = synthetic
source                  1..12
                        mol_type = protein
                        organism = synthetic construct
SEQUENCE: 192
QSVLYSSNNK NY                                                        12

SEQ ID NO: 193          moltype =    length =
SEQUENCE: 193
000

SEQ ID NO: 194          moltype =    length =
SEQUENCE: 194
000

SEQ ID NO: 195          moltype = DNA  length = 24
FEATURE                 Location/Qualifiers
misc_feature            1..24
                        note = synthetic
source                  1..24
                        mol_type = other DNA
```

-continued

```
                    organism = synthetic construct
SEQUENCE: 195
cagcaatttt atactgttcc cact                                        24

SEQ ID NO: 196        moltype = AA   length = 8
FEATURE               Location/Qualifiers
REGION                1..8
                      note = synthetic
source                1..8
                      mol_type = protein
                      organism = synthetic construct
SEQUENCE: 196
QQFYTVPT                                                           8

SEQ ID NO: 197        moltype = DNA   length = 357
FEATURE               Location/Qualifiers
misc_feature          1..357
                      note = synthetic
source                1..357
                      mol_type = other DNA
                      organism = synthetic construct
SEQUENCE: 197
caggtgcagc tggtggagtc tggggggaggc gtggtccagc ctgggaggtc cctgagactc  60
tcctgtgtag cctctggatt caccttcagg aactatgaca tgcactgggt ccgccaggct 120
cctggcaagg ggctggaatg ggtggcagtt acatcatctg atggacttaa taaattctat 180
tcagactccg tgaagggccg attcaccatc tccagagaca cacgctgtct 240
ctgcaaatta ccggcctgag agctgaggac acggctgtgt attactgtgc gaaagagtcc 300
attttagcag ccctctttga ctactggggc cagggaaccc tggtcaccgt ctcctca    357

SEQ ID NO: 198        moltype = AA   length = 119
FEATURE               Location/Qualifiers
REGION                1..119
                      note = synthetic
source                1..119
                      mol_type = protein
                      organism = synthetic construct
SEQUENCE: 198
QVQLVESGGG VVQPGRSLRL SCVASGFTFR NYDMHWVRQA PGKGLEWVAV TSSDGLNKFY  60
SDSVKGRFTI SRDNSKNTLS LQITGLRAED TAVYYCAKES ILAALFDYWG QGTLVTVSS  119

SEQ ID NO: 199        moltype = DNA   length = 24
FEATURE               Location/Qualifiers
misc_feature          1..24
                      note = synthetic
source                1..24
                      mol_type = other DNA
                      organism = synthetic construct
SEQUENCE: 199
ggattcacct tcaggaacta tgac                                        24

SEQ ID NO: 200        moltype = AA   length = 8
FEATURE               Location/Qualifiers
REGION                1..8
                      note = synthetic
source                1..8
                      mol_type = protein
                      organism = synthetic construct
SEQUENCE: 200
GFTFRNYD                                                           8

SEQ ID NO: 201        moltype = DNA   length = 24
FEATURE               Location/Qualifiers
misc_feature          1..24
                      note = synthetic
source                1..24
                      mol_type = other DNA
                      organism = synthetic construct
SEQUENCE: 201
acatcatctg atggacttaa taaa                                        24

SEQ ID NO: 202        moltype = AA   length = 8
FEATURE               Location/Qualifiers
REGION                1..8
                      note = synthetic
source                1..8
                      mol_type = protein
                      organism = synthetic construct
SEQUENCE: 202
TSSDGLNK                                                           8
```

-continued

```
SEQ ID NO: 203            moltype = DNA  length = 36
FEATURE                   Location/Qualifiers
misc_feature              1..36
                          note = synthetic
source                    1..36
                          mol_type = other DNA
                          organism = synthetic construct
SEQUENCE: 203
gcgaaagagt ccattttagc agccctcttt gactac                                 36

SEQ ID NO: 204            moltype = AA  length = 12
FEATURE                   Location/Qualifiers
REGION                    1..12
                          note = synthetic
source                    1..12
                          mol_type = protein
                          organism = synthetic construct
SEQUENCE: 204
AKESILAALF DY                                                           12

SEQ ID NO: 205            moltype = DNA  length = 336
FEATURE                   Location/Qualifiers
misc_feature              1..336
                          note = synthetic
source                    1..336
                          mol_type = other DNA
                          organism = synthetic construct
SEQUENCE: 205
gacatcgtga tgacccagtc tccagactcc ctggctgtgt ctctgggcga gagggccacc       60
atcaactgca agtccagcca gagtgtttta tacagctcca acaataagaa ctacttggct      120
tggtaccagc agaaaccagg acagcctcct aagctgctct tttactgggc atctacccgg      180
gaatccgggg tccctgaccg attcagtggc agcgggtctg ggacagattt cactctcacc      240
atcagcagcc tgcaggctga agatgtggca gtttattact gtcagcaaca ttatactact      300
cccacttttg gccaggggac caagctggag atcaaa                                336

SEQ ID NO: 206            moltype = AA  length = 112
FEATURE                   Location/Qualifiers
REGION                    1..112
                          note = synthetic
source                    1..112
                          mol_type = protein
                          organism = synthetic construct
SEQUENCE: 206
DIVMTQSPDS LAVSLGERAT INCKSSQSVL YSSNNKNYLA WYQQKPGQPP KLLFYWASTR       60
ESGVPDRFSG SGSGTDFTLT ISSLQAEDVA VYYCQQHYTT PTFGQGTKLE IK              112

SEQ ID NO: 207            moltype = DNA  length = 36
FEATURE                   Location/Qualifiers
misc_feature              1..36
                          note = synthetic
source                    1..36
                          mol_type = other DNA
                          organism = synthetic construct
SEQUENCE: 207
cagagtgttt tatacagctc caacaataag aactac                                 36

SEQ ID NO: 208            moltype = AA  length = 12
FEATURE                   Location/Qualifiers
REGION                    1..12
                          note = synthetic
source                    1..12
                          mol_type = protein
                          organism = synthetic construct
SEQUENCE: 208
QSVLYSSNNK NY                                                           12

SEQ ID NO: 209            moltype =   length =
SEQUENCE: 209
000

SEQ ID NO: 210            moltype =   length =
SEQUENCE: 210
000

SEQ ID NO: 211            moltype = DNA  length = 24
FEATURE                   Location/Qualifiers
misc_feature              1..24
                          note = synthetic
```

-continued

```
source                    1..24
                          mol_type = other DNA
                          organism = synthetic construct
SEQUENCE: 211
cagcaacatt atactactcc cact                                         24

SEQ ID NO: 212            moltype = AA  length = 8
FEATURE                   Location/Qualifiers
REGION                    1..8
                          note = synthetic
source                    1..8
                          mol_type = protein
                          organism = synthetic construct
SEQUENCE: 212
QQHYTTPT                                                           8

SEQ ID NO: 213            moltype = DNA  length = 357
FEATURE                   Location/Qualifiers
misc_feature              1..357
                          note = synthetic
source                    1..357
                          mol_type = other DNA
                          organism = synthetic construct
SEQUENCE: 213
caggtgcagc tggtggagtc tgggggaggc gtggtccagc ctgggaggtc cctgagactc   60
tcctgtgcag cctctggatt caccttcagt agctatggca tgcactgggt ccgccagact  120
ccgggcaagg ggctggagtg ggtggcattt atatcatatg atggaaataa taaatactat  180
gcagactccg tgaagggccg attcaccatc tccagagaca attccaagaa cacgctgttt  240
ctgcaaatga acagcctgag agctgaggac acggctgtgt attactgtgc gaaagagtcc  300
attttagcag ccctctttga ctactggggc cagggaaccc tggtcaccgt ctcctca     357

SEQ ID NO: 214            moltype = AA  length = 119
FEATURE                   Location/Qualifiers
REGION                    1..119
                          note = synthetic
source                    1..119
                          mol_type = protein
                          organism = synthetic construct
SEQUENCE: 214
QVQLVESGGG VVQPGRSLRL SCAASGFTFS SYGMHWVRQT PGKGLEWVAF ISYDGNNKYY   60
ADSVKGRFTI SRDNSKNTLF LQMNSLRAED TAVYYCAKES ILAALFDYWG QGTLVTVSS   119

SEQ ID NO: 215            moltype = DNA  length = 24
FEATURE                   Location/Qualifiers
misc_feature              1..24
                          note = synthetic
source                    1..24
                          mol_type = other DNA
                          organism = synthetic construct
SEQUENCE: 215
ggattcacct tcagtagcta tggc                                         24

SEQ ID NO: 216            moltype = AA  length = 8
FEATURE                   Location/Qualifiers
REGION                    1..8
                          note = synthetic
source                    1..8
                          mol_type = protein
                          organism = synthetic construct
SEQUENCE: 216
GFTFSSYG                                                           8

SEQ ID NO: 217            moltype = DNA  length = 24
FEATURE                   Location/Qualifiers
misc_feature              1..24
                          note = synthetic
source                    1..24
                          mol_type = other DNA
                          organism = synthetic construct
SEQUENCE: 217
atatcatatg atggaaataa taaa                                         24

SEQ ID NO: 218            moltype = AA  length = 8
FEATURE                   Location/Qualifiers
REGION                    1..8
                          note = synthetic
source                    1..8
                          mol_type = protein
                          organism = synthetic construct
```

-continued

```
SEQUENCE: 218
ISYDGNNK                                                                  8

SEQ ID NO: 219        moltype = DNA  length = 36
FEATURE               Location/Qualifiers
misc_feature          1..36
                      note = synthetic
source                1..36
                      mol_type = other DNA
                      organism = synthetic construct
SEQUENCE: 219
gcgaaagagt ccattttagc agccctcttt gactac                                   36

SEQ ID NO: 220        moltype = AA  length = 12
FEATURE               Location/Qualifiers
REGION                1..12
                      note = synthetic
source                1..12
                      mol_type = protein
                      organism = synthetic construct
SEQUENCE: 220
AKESILAALF DY                                                             12

SEQ ID NO: 221        moltype = DNA  length = 336
FEATURE               Location/Qualifiers
misc_feature          1..336
                      note = synthetic
source                1..336
                      mol_type = other DNA
                      organism = synthetic construct
SEQUENCE: 221
gacatcgtga tgacccagtc tccagactcc ctggctgtgt ctctgggcga gagggccacc          60
atcaactgca agtccagcca gagtgtttta tacagctcca acaataagaa ctacttagct         120
tggtaccagc agaaacctgg acagcctcct aagctgctca tttactgggc atctacccgg         180
gaatccgggg tccctgaccg attcagtggc agcgggtctg ggacagattt cactctcacc         240
atcagcagcc tgcaggctga agatgtggca ctttattact gtcaacaata ttataatact         300
cccacttttg gccagggac caagctggag atcaaa                                    336

SEQ ID NO: 222        moltype = AA  length = 112
FEATURE               Location/Qualifiers
REGION                1..112
                      note = synthetic
source                1..112
                      mol_type = protein
                      organism = synthetic construct
SEQUENCE: 222
DIVMTQSPDS LAVSLGERAT INCKSSQSVL YSSNNKNYLA WYQQKPGQPP KLLIYWASTR          60
ESGVPDRFSG SGSGTDFTLT ISSLQAEDVA LYYCQQYYNT PTFGQGTKLE IK                 112

SEQ ID NO: 223        moltype = DNA  length = 36
FEATURE               Location/Qualifiers
misc_feature          1..36
                      note = synthetic
source                1..36
                      mol_type = other DNA
                      organism = synthetic construct
SEQUENCE: 223
cagagtgttt tatacagctc caacaataag aactac                                   36

SEQ ID NO: 224        moltype = AA  length = 12
FEATURE               Location/Qualifiers
REGION                1..12
                      note = synthetic
source                1..12
                      mol_type = protein
                      organism = synthetic construct
SEQUENCE: 224
QSVLYSSNNK NY                                                             12

SEQ ID NO: 225        moltype =    length =
SEQUENCE: 225
000

SEQ ID NO: 226        moltype =    length =
SEQUENCE: 226
000

SEQ ID NO: 227        moltype = DNA  length = 24
FEATURE               Location/Qualifiers
```

-continued

```
misc_feature          1..24
                      note = synthetic
source                1..24
                      mol_type = other DNA
                      organism = synthetic construct
SEQUENCE: 227
caacaatatt ataatactcc cact                                                  24

SEQ ID NO: 228        moltype = AA  length = 8
FEATURE               Location/Qualifiers
REGION                1..8
                      note = synthetic
source                1..8
                      mol_type = protein
                      organism = synthetic construct
SEQUENCE: 228
QQYYNTPT                                                                    8

SEQ ID NO: 229        moltype = DNA  length = 357
FEATURE               Location/Qualifiers
misc_feature          1..357
                      note = synthetic
source                1..357
                      mol_type = other DNA
                      organism = synthetic construct
SEQUENCE: 229
caggtgcagc tggtggagtc tggggggggc gtggtccagc ctgggaggtc cctgagactc   60
tcctgtgcag cctctggatt caccttcagt agctatggca tgcactgggt ccgccaggct  120
ccagtcaagg ggctggagtg ggtggcattt atatcatatg atggaagtaa taaatactat  180
gcagactccg tgaagggccg attcaccatc tccagagaca attccaagaa cacgctgtat  240
ctccaaatga acagcctgac agctgaggac acggctgttt attactgtgc gaaagagtcc  300
attttagcag ccctctttga ctactggggc cagggaaccc tggtcaccgt ctcctca     357

SEQ ID NO: 230        moltype = AA  length = 119
FEATURE               Location/Qualifiers
REGION                1..119
                      note = synthetic
source                1..119
                      mol_type = protein
                      organism = synthetic construct
SEQUENCE: 230
QVQLVESGGG VVQPGRSLRL SCAASGFTFS SYGMHWVRQA PVKGLEWVAF ISYDGSNKYY   60
ADSVKGRFTI SRDNSKNTLY LQMNSLTAED TAVYYCAKES ILAALFDYWG QGTLVTVSS    119

SEQ ID NO: 231        moltype = DNA  length = 24
FEATURE               Location/Qualifiers
misc_feature          1..24
                      note = synthetic
source                1..24
                      mol_type = other DNA
                      organism = synthetic construct
SEQUENCE: 231
ggattcacct tcagtagcta tggc                                                  24

SEQ ID NO: 232        moltype = AA  length = 8
FEATURE               Location/Qualifiers
REGION                1..8
                      note = synthetic
source                1..8
                      mol_type = protein
                      organism = synthetic construct
SEQUENCE: 232
GFTFSSYG                                                                    8

SEQ ID NO: 233        moltype = DNA  length = 24
FEATURE               Location/Qualifiers
misc_feature          1..24
                      note = synthetic
source                1..24
                      mol_type = other DNA
                      organism = synthetic construct
SEQUENCE: 233
atatcatatg atggaagtaa taaa                                                  24

SEQ ID NO: 234        moltype = AA  length = 8
FEATURE               Location/Qualifiers
REGION                1..8
                      note = synthetic
source                1..8
```

-continued

```
                         mol_type = protein
                         organism = synthetic construct
SEQUENCE: 234
ISYDGSNK                                                                8

SEQ ID NO: 235          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 235
gcgaaagagt ccattttagc agccctcttt gactac                                 36

SEQ ID NO: 236          moltype = AA  length = 12
FEATURE                 Location/Qualifiers
REGION                  1..12
                        note = synthetic
source                  1..12
                        mol_type = protein
                        organism = synthetic construct
SEQUENCE: 236
AKESILAALF DY                                                           12

SEQ ID NO: 237          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 237
gacatcgtga tgacccagtc tccagactcc ctggctgtgt ctctgggcga gagggccacc  60
atcaactgca agtccagcca gagtgtttta tacagttcca acaataagaa ctacttagct  120
tggtaccagc agaaaccaag acagcctcct aagctgctca tttactgggc atctattcgg  180
gaatccgggg tccctgaccg attcagtggc agcgggtctg ggacagattt cattctcacc  240
atcagcagcc tgcaggctga agatgtggca gtttattact gtcagcaatt ttatagtatt  300
cccactttg gccaggggac caagctggag atcaaa                               336

SEQ ID NO: 238          moltype = AA  length = 112
FEATURE                 Location/Qualifiers
REGION                  1..112
                        note = synthetic
source                  1..112
                        mol_type = protein
                        organism = synthetic construct
SEQUENCE: 238
DIVMTQSPDS LAVSLGERAT INCKSSQSVL YSSNNKNYLA WYQQKPRQPP KLLIYWASIR  60
ESGVPDRFSG SGSGTDFILT ISSLQAEDVA VYYCQQFYSI PTFGQGTKLE IK           112

SEQ ID NO: 239          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 239
cagagtgttt tatacagttc caacaataag aactac                                 36

SEQ ID NO: 240          moltype = AA  length = 12
FEATURE                 Location/Qualifiers
REGION                  1..12
                        note = synthetic
source                  1..12
                        mol_type = protein
                        organism = synthetic construct
SEQUENCE: 240
QSVLYSSNNK NY                                                           12

SEQ ID NO: 241          moltype =   length =
SEQUENCE: 241
000

SEQ ID NO: 242          moltype =   length =
SEQUENCE: 242
000
```

-continued

```
SEQ ID NO: 243            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 243
cagcaatttt atagtattcc cact                                      24

SEQ ID NO: 244            moltype = AA   length = 8
FEATURE                   Location/Qualifiers
REGION                    1..8
                          note = synthetic
source                    1..8
                          mol_type = protein
                          organism = synthetic construct
SEQUENCE: 244
QQFYSIPT                                                        8

SEQ ID NO: 245            moltype = DNA   length = 357
FEATURE                   Location/Qualifiers
misc_feature              1..357
                          note = synthetic
source                    1..357
                          mol_type = other DNA
                          organism = synthetic construct
SEQUENCE: 245
caggtgcagc tggtggagtc tgggggaggc gtggtccagc ctgggaggtc cctgagactc   60
tcctgtgcag cctctggatt caccttTagt agctatggca tgcactgggt ccgccaggct  120
ccagtcaagg ggctggagtg ggtggcattt atatcaaatg ataaaagtaa taaatattat  180
gcagactcct tgaagggccg attcaccatc tccagagaca attccaagaa cacgctgtat  240
ctgcaaatga acagcctgac agctgaagac acggctgttt attactgtgc gaaagagtcc  300
atttTagcag ccctctttga ctattggggc cagggaaccc tggtcaccgt ctcctca     357

SEQ ID NO: 246            moltype = AA   length = 119
FEATURE                   Location/Qualifiers
REGION                    1..119
                          note = synthetic
source                    1..119
                          mol_type = protein
                          organism = synthetic construct
SEQUENCE: 246
QVQLVESGGG VVQPGRSLRL SCAASGFTFS SYGMHWVRQA PVKGLEWVAF ISNDKSNKYY   60
ADSLKGRFTI SRDNSKNTLY LQMNSLTAED TAVYYCAKES ILAALFDYWG QGTLVTVSS   119

SEQ ID NO: 247            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 247
ggattcacct ttagtagcta tggc                                      24

SEQ ID NO: 248            moltype = AA   length = 8
FEATURE                   Location/Qualifiers
REGION                    1..8
                          note = synthetic
source                    1..8
                          mol_type = protein
                          organism = synthetic construct
SEQUENCE: 248
GFTFSSYG                                                        8

SEQ ID NO: 249            moltype = DNA   length = 24
FEATURE                   Location/Qualifiers
misc_feature              1..24
                          note = synthetic
source                    1..24
                          mol_type = other DNA
                          organism = synthetic construct
SEQUENCE: 249
atatcaaatg ataaaagtaa taaa                                      24

SEQ ID NO: 250            moltype = AA   length = 8
FEATURE                   Location/Qualifiers
REGION                    1..8
```

-continued

```
                          note = synthetic
source                    1..8
                          mol_type = protein
                          organism = synthetic construct
SEQUENCE: 250
ISNDKSNK                                                             8

SEQ ID NO: 251            moltype = DNA  length = 36
FEATURE                   Location/Qualifiers
misc_feature              1..36
                          note = synthetic
source                    1..36
                          mol_type = other DNA
                          organism = synthetic construct
SEQUENCE: 251
gcgaaagagt ccattttagc agccctcttt gactat                              36

SEQ ID NO: 252            moltype = AA  length = 12
FEATURE                   Location/Qualifiers
REGION                    1..12
                          note = synthetic
source                    1..12
                          mol_type = protein
                          organism = synthetic construct
SEQUENCE: 252
AKESILAALF DY                                                        12

SEQ ID NO: 253            moltype = DNA  length = 336
FEATURE                   Location/Qualifiers
misc_feature              1..336
                          note = synthetic
source                    1..336
                          mol_type = other DNA
                          organism = synthetic construct
SEQUENCE: 253
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccaag acagcctcct aagctactca tttactgggc atctattcgg  180
gaatccgggg tccctgaccg attcagtggc agcgggtctg ggacagattt cactctcacc  240
atcagcagcc tgcaggctga agatgtggca gtttattact gtcaacaatt ttatagtgtt  300
cccacttttg gccaggggac caagctggag atcaaa                             336

SEQ ID NO: 254            moltype = AA  length = 112
FEATURE                   Location/Qualifiers
REGION                    1..112
                          note = synthetic
source                    1..112
                          mol_type = protein
                          organism = synthetic construct
SEQUENCE: 254
DIVMTQSPDS LAVSLGERAT INCKSSQSVL YSSNNKNYLA WYQQKPRQPP KLLIYWASIR   60
ESGVPDRFSG SGSGTDFTLT ISSLQAEDVA VYYCQQFYSV PTFGQGTKLE IK           112

SEQ ID NO: 255            moltype = DNA  length = 36
FEATURE                   Location/Qualifiers
misc_feature              1..36
                          note = synthetic
source                    1..36
                          mol_type = other DNA
                          organism = synthetic construct
SEQUENCE: 255
cagagtgttt tatacagctc caacaataag aactac                             36

SEQ ID NO: 256            moltype = AA  length = 12
FEATURE                   Location/Qualifiers
REGION                    1..12
                          note = synthetic
source                    1..12
                          mol_type = protein
                          organism = synthetic construct
SEQUENCE: 256
QSVLYSSNNK NY                                                        12

SEQ ID NO: 257            moltype =   length =
SEQUENCE: 257
000

SEQ ID NO: 258            moltype =   length =
SEQUENCE: 258
```

-continued

```
000

SEQ ID NO: 259          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 259
caacaatttt atagtgttcc cact                                      24

SEQ ID NO: 260          moltype = AA   length = 8
FEATURE                 Location/Qualifiers
REGION                  1..8
                        note = synthetic
source                  1..8
                        mol_type = protein
                        organism = synthetic construct
SEQUENCE: 260
QQFYSVPT                                                        8

SEQ ID NO: 261          moltype = DNA   length = 357
FEATURE                 Location/Qualifiers
misc_feature            1..357
                        note = synthetic
source                  1..357
                        mol_type = other DNA
                        organism = synthetic construct
SEQUENCE: 261
caggtgcagc tggtggagtc tgggggaggc gtggtccagc ctgggaggtc cctgagactc   60
tcctgtgcag cctctggatt caccttcagt agctatggca tgcactgggt ccgccaggct  120
ccagtcaagg ggctggagtg ggtggcattt atatcatttg atggaagtaa taaatactat  180
acagactccg tgaagggccg attcaccatc tccagagaca attccaagaa cacgctgtat  240
ctccaaatga acagcctgac agctgaggac acggctattt attactgtgc gaaagagtcc  300
attttagcag ccctctttga ctactggggc cagggaaccc tggtcactgt ctcctca      357

SEQ ID NO: 262          moltype = AA   length = 119
FEATURE                 Location/Qualifiers
REGION                  1..119
                        note = synthetic
source                  1..119
                        mol_type = protein
                        organism = synthetic construct
SEQUENCE: 262
QVQLVESGGG VVQPGRSLRL SCAASGFTFS SYGMHWVRQA PVKGLEWVAF ISFDGSNKYY   60
TDSVKGRFTI SRDNSKNTLY LQMNSLTAED TAIYYCAKES ILAALFDYWG QGTLVTVSS   119

SEQ ID NO: 263          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 263
ggattcacct tcagtagcta tggc                                      24

SEQ ID NO: 264          moltype = AA   length = 8
FEATURE                 Location/Qualifiers
REGION                  1..8
                        note = synthetic
source                  1..8
                        mol_type = protein
                        organism = synthetic construct
SEQUENCE: 264
GFTFSSYG                                                        8

SEQ ID NO: 265          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 265
atatcatttg atggaagtaa taaa                                      24

SEQ ID NO: 266          moltype = AA   length = 8
```

-continued

```
FEATURE               Location/Qualifiers
REGION                1..8
                      note = synthetic
source                1..8
                      mol_type = protein
                      organism = synthetic construct
SEQUENCE: 266
ISFDGSNK                                                                  8

SEQ ID NO: 267        moltype = DNA  length = 36
FEATURE               Location/Qualifiers
misc_feature          1..36
                      note = synthetic
source                1..36
                      mol_type = other DNA
                      organism = synthetic construct
SEQUENCE: 267
gcgaaagagt ccattttagc agccctcttt gactac                                   36

SEQ ID NO: 268        moltype = AA  length = 12
FEATURE               Location/Qualifiers
REGION                1..12
                      note = synthetic
source                1..12
                      mol_type = protein
                      organism = synthetic construct
SEQUENCE: 268
AKESILAALF DY                                                            12

SEQ ID NO: 269        moltype = DNA  length = 336
FEATURE               Location/Qualifiers
misc_feature          1..336
                      note = synthetic
source                1..336
                      mol_type = other DNA
                      organism = synthetic construct
SEQUENCE: 269
gacatcgtga tgacccagtc tccagactcc ctggctgtgt ctctgggcga gagggccacc   60
atcaactgca agtccagcca gagtgtttta tacagctcca acaataagaa ctacttagct  120
tggtaccagc agaaaccaag acagcctcct aacctgctca tttactgggc atctattcgg  180
gaatccgggg tccctgaccg attcagtggc agcgggtctg ggacagattt cactctcacc  240
atcagcagcc tgcaggctga agatgtggca ttttattact gtcagcaatt ttatagtatt  300
cccacttttg gccaggggac caagctggag atcaaa                             336

SEQ ID NO: 270        moltype = AA  length = 112
FEATURE               Location/Qualifiers
REGION                1..112
                      note = synthetic
source                1..112
                      mol_type = protein
                      organism = synthetic construct
SEQUENCE: 270
DIVMTQSPDS LAVSLGERAT INCKSSQSVL YSSNNKNYLA WYQQKPRQPP NLLIYWASIR   60
ESGVPDRFSG SGSGTDFTLT ISSLQAEDVA FYYCQQFYSI PTFGQGTKLE IK           112

SEQ ID NO: 271        moltype = DNA  length = 36
FEATURE               Location/Qualifiers
misc_feature          1..36
                      note = synthetic
source                1..36
                      mol_type = other DNA
                      organism = synthetic construct
SEQUENCE: 271
cagagtgttt tatacagctc caacaataag aactac                                   36

SEQ ID NO: 272        moltype = AA  length = 12
FEATURE               Location/Qualifiers
REGION                1..12
                      note = synthetic
source                1..12
                      mol_type = protein
                      organism = synthetic construct
SEQUENCE: 272
QSVLYSSNNK NY                                                            12

SEQ ID NO: 273        moltype =   length =
SEQUENCE: 273
000
```

-continued

```
SEQ ID NO: 274          moltype =   length =
SEQUENCE: 274
000

SEQ ID NO: 275          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 275
cagcaatttt atagtattcc cact                                           24

SEQ ID NO: 276          moltype = AA  length = 8
FEATURE                 Location/Qualifiers
REGION                  1..8
                        note = synthetic
source                  1..8
                        mol_type = protein
                        organism = synthetic construct
SEQUENCE: 276
QQFYSIPT                                                             8

SEQ ID NO: 277          moltype = DNA  length = 357
FEATURE                 Location/Qualifiers
misc_feature            1..357
                        note = synthetic
source                  1..357
                        mol_type = other DNA
                        organism = synthetic construct
SEQUENCE: 277
caggtgcagc tggtggagtc tgggggaggc gtggtccagc ctgggaggtc cctgagactc    60
tcctgtgcag cctctggatt caccttagg acctatggca tgcactgggt ccgccaggct   120
ccagtcaagg ggctggagtg ggtggcattt atatcaaagg atggaagtga taaatactat   180
gtagactccg tgaagggccg attcaccatc tccagagaca attccaagaa cacgctgttt   240
ctgcaaatga acagcctgac agctgaggac acggctgttt attattgtgc gaaagagtcc   300
attttagcag ccctctttga ctactggggc cagggaaccc tggtcactgt ctcctca      357

SEQ ID NO: 278          moltype = AA  length = 119
FEATURE                 Location/Qualifiers
REGION                  1..119
                        note = synthetic
source                  1..119
                        mol_type = protein
                        organism = synthetic construct
SEQUENCE: 278
QVQLVESGGG VVQPGRSLRL SCAASGFTFR TYGMHWVRQA PVKGLEWVAF ISKDGSDKYY    60
VDSVKGRFTI SRDNSKNTLF LQMNSLTAED TAVYYCAKES ILAALFDYWG QGTLVTVSS    119

SEQ ID NO: 279          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 279
ggattcacct ttaggaccta tggc                                          24

SEQ ID NO: 280          moltype = AA  length = 8
FEATURE                 Location/Qualifiers
REGION                  1..8
                        note = synthetic
source                  1..8
                        mol_type = protein
                        organism = synthetic construct
SEQUENCE: 280
GFTFRTYG                                                             8

SEQ ID NO: 281          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 281
atatcaaagg atggaagtga taaa                                          24
```

```
SEQ ID NO: 282            moltype = AA   length = 8
FEATURE                   Location/Qualifiers
REGION                    1..8
                          note = synthetic
source                    1..8
                          mol_type = protein
                          organism = synthetic construct
SEQUENCE: 282
ISKDGSDK                                                                  8

SEQ ID NO: 283            moltype = DNA  length = 36
FEATURE                   Location/Qualifiers
misc_feature              1..36
                          note = synthetic
source                    1..36
                          mol_type = other DNA
                          organism = synthetic construct
SEQUENCE: 283
gcgaaagagt ccattttagc agccctcttt gactac                                  36

SEQ ID NO: 284            moltype = AA   length = 12
FEATURE                   Location/Qualifiers
REGION                    1..12
                          note = synthetic
source                    1..12
                          mol_type = protein
                          organism = synthetic construct
SEQUENCE: 284
AKESILAALF DY                                                            12

SEQ ID NO: 285            moltype = DNA  length = 336
FEATURE                   Location/Qualifiers
misc_feature              1..336
                          note = synthetic
source                    1..336
                          mol_type = other DNA
                          organism = synthetic construct
SEQUENCE: 285
gacatcgtga tgacccagtc tccagactcc ctggctgtgt ctctgggcga gagggccacc   60
atcaactgca agtccagcca gagtgtttta tacagctcca acaataagaa ctacttagct  120
tggtaccagc agaaaccaag acagcctcct aaactcctca tttactgggc atctaatcgg  180
gaatccgggg tccctgaccg attcagtggc agcgggtctg ggacagattt cactctcacc  240
atcagcagcc tgcaggctga agatgtggca gtttattact gtcagcaatt ttatagtgtt  300
cccacttttg gccagggggac caagctggag atcaaa                            336

SEQ ID NO: 286            moltype = AA   length = 112
FEATURE                   Location/Qualifiers
REGION                    1..112
                          note = synthetic
source                    1..112
                          mol_type = protein
                          organism = synthetic construct
SEQUENCE: 286
DIVMTQSPDS LAVSLGERAT INCKSSQSVL YSSNNKNYLA WYQQKPRQPP KLLIYWASNR   60
ESGVPDRFSG SGSGTDFTLT ISSLQAEDVA VYYCQQFYSV PTFGQGTKLE IK           112

SEQ ID NO: 287            moltype = DNA  length = 36
FEATURE                   Location/Qualifiers
misc_feature              1..36
                          note = synthetic
source                    1..36
                          mol_type = other DNA
                          organism = synthetic construct
SEQUENCE: 287
cagagtgttt tatacagctc caacaataag aactac                                  36

SEQ ID NO: 288            moltype = AA   length = 12
FEATURE                   Location/Qualifiers
REGION                    1..12
                          note = synthetic
source                    1..12
                          mol_type = protein
                          organism = synthetic construct
SEQUENCE: 288
QSVLYSSNNK NY                                                            12

SEQ ID NO: 289            moltype =    length =
SEQUENCE: 289
```

-continued

```
000

SEQ ID NO: 290          moltype =   length =
SEQUENCE: 290
000

SEQ ID NO: 291          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 291
cagcaatttt atagtgttcc cact                                        24

SEQ ID NO: 292          moltype = AA  length = 8
FEATURE                 Location/Qualifiers
REGION                  1..8
                        note = synthetic
source                  1..8
                        mol_type = protein
                        organism = synthetic construct
SEQUENCE: 292
QQFYSVPT                                                          8

SEQ ID NO: 293          moltype = DNA  length = 357
FEATURE                 Location/Qualifiers
misc_feature            1..357
                        note = synthetic
source                  1..357
                        mol_type = other DNA
                        organism = synthetic construct
SEQUENCE: 293
caggtgcagc tggtggagtc tggggggaggc gtggtccagc ctgggaggtc cctgagactc   60
tcctgtgcag cctctggatt cacctttagt agctatggca tgcactgggt ccgccaggct  120
ccagtcaagg ggctggagtg ggtggcattt atatcaaatg ataaaagtaa taaatactat  180
gcagactccg tgaagggccg attcaccatc tccagagaca attccaagaa cacgctgtat  240
ctgcaaatga acagcctgac agctgaggac acggctgttt attactgtgc gaaagagtcc  300
attttagcag ccctctttga ctcctggggc cagggaacc tggtcaccgt ctcctca     357

SEQ ID NO: 294          moltype = AA  length = 119
FEATURE                 Location/Qualifiers
REGION                  1..119
                        note = synthetic
source                  1..119
                        mol_type = protein
                        organism = synthetic construct
SEQUENCE: 294
QVQLVESGGG VVQPGRSLRL SCAASGFTFS SYGMHWVRQA PVKGLEWVAF ISNDKSNKYY   60
ADSVKGRFTI SRDNSKNTLY LQMNSLTAED TAVYYCAKES ILAALFDSWG QGTLVTVSS   119

SEQ ID NO: 295          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 295
ggattcacct ttagtagcta tggc                                        24

SEQ ID NO: 296          moltype = AA  length = 8
FEATURE                 Location/Qualifiers
REGION                  1..8
                        note = synthetic
source                  1..8
                        mol_type = protein
                        organism = synthetic construct
SEQUENCE: 296
GFTFSSYG                                                          8

SEQ ID NO: 297          moltype = DNA  length = 24
FEATURE                 Location/Qualifiers
misc_feature            1..24
                        note = synthetic
source                  1..24
                        mol_type = other DNA
                        organism = synthetic construct
```

-continued

```
SEQUENCE: 297
atatcaaatg ataaaagtaa taaa                                             24

SEQ ID NO: 298          moltype = AA  length = 8
FEATURE                 Location/Qualifiers
REGION                  1..8
                        note = synthetic
source                  1..8
                        mol_type = protein
                        organism = synthetic construct
SEQUENCE: 298
ISNDKSNK                                                               8

SEQ ID NO: 299          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 299
gcgaaagagt ccattttagc agccctcttt gactcc                                36

SEQ ID NO: 300          moltype = AA  length = 12
FEATURE                 Location/Qualifiers
REGION                  1..12
                        note = synthetic
source                  1..12
                        mol_type = protein
                        organism = synthetic construct
SEQUENCE: 300
AKESILAALF DS                                                          12

SEQ ID NO: 301          moltype = DNA  length = 336
FEATURE                 Location/Qualifiers
misc_feature            1..336
                        note = synthetic
source                  1..336
                        mol_type = other DNA
                        organism = synthetic construct
SEQUENCE: 301
gacatcgtga tgacccagtc tccagactcc ctggctgtgt ctctgggcga gagggccacc     60
atcaactgca agtccagcca gagtgtttta tacagctcca acaataagaa ctacttagct    120
tggtaccagc agaaaccaag acagcctcct aagctgctca tttactgggc atctattcgg    180
gaatccgggg tccctgaccg attcagtggc agcgggtctg gggcagattt cactctcacc    240
atcagcagc tgcaggctgc agatgtggca gtttattact gtcagcaatt ttatagtgtt      300
cccactttg gccaggggac caagctggag atcaaa                               336

SEQ ID NO: 302          moltype = AA  length = 112
FEATURE                 Location/Qualifiers
REGION                  1..112
                        note = synthetic
source                  1..112
                        mol_type = protein
                        organism = synthetic construct
SEQUENCE: 302
DIVMTQSPDS LAVSLGERAT INCKSSQSVL YSSNNKNYLA WYQQKPRQPP KLLIYWASIR      60
ESGVPDRFSG SGSGADFTLT ISSLQAADVA VYYCQQFYSV PTFGQGTKLE IK             112

SEQ ID NO: 303          moltype = DNA  length = 36
FEATURE                 Location/Qualifiers
misc_feature            1..36
                        note = synthetic
source                  1..36
                        mol_type = other DNA
                        organism = synthetic construct
SEQUENCE: 303
cagagtgttt tatacagctc caacaataag aactac                                36

SEQ ID NO: 304          moltype = AA  length = 12
FEATURE                 Location/Qualifiers
REGION                  1..12
                        note = synthetic
source                  1..12
                        mol_type = protein
                        organism = synthetic construct
SEQUENCE: 304
QSVLYSSNNK NY                                                          12
```

-continued

```
SEQ ID NO: 305          moltype =    length =
SEQUENCE: 305
000

SEQ ID NO: 306          moltype =    length =
SEQUENCE: 306
000

SEQ ID NO: 307          moltype = DNA   length = 24
FEATURE                 Location/Qualifiers
misc_feature            1..24
                        note = synthetic
source                  1..24
                        mol_type = other DNA
                        organism = synthetic construct
SEQUENCE: 307
cagcaatttt atagtgttcc cact                                      24

SEQ ID NO: 308          moltype = AA   length = 8
FEATURE                 Location/Qualifiers
REGION                  1..8
                        note = synthetic
source                  1..8
                        mol_type = protein
                        organism = synthetic construct
SEQUENCE: 308
QQFYSVPT                                                        8
```

What is claimed is:

1. A method for treating a patient having severe insulin resistance, the method comprising administering to the patient a therapeutically effective amount of a composition comprising a glucagon receptor (GCGR) antagonist, wherein the GCGR antagonist lowers blood glucose levels or levels of ketone bodies of the patient, mediates a condition or disease associated with severe insulin resistance, or alleviates or reduces in severity at least one symptom or complication associated with the condition or disease, wherein:

the severe insulin resistance is associated with a genetic variant of one or more genes selected from the group consisting of INSR, PSMD6, ADRA2A, AGPAT2, AKT2, APPL1, BBS1, BSCL2, CIDEC, GRB10, IRS2, KLF14, LEP, LEPR, LMNA, MC4R, PCNT, PIK2CA, POLD1, PPARG, PTPRD, PTRF, RASGRP1, TBCID4, and TCF712, and wherein the GCGR antagonist is an isolated human monoclonal antibody or antigen-binding fragment thereof comprising:

(a) a heavy chain variable region (HCVR) comprising three heavy chain complementarity determining regions (HCDR1, HCDR2, and HCDR3) that are contained within an HCVR comprising the amino acid sequence set forth in SEQ ID NO: 86; and a light chain variable region (LCVR) comprising three light chain complementarity determining regions (LCDR1, LCDR2, and LCDR3) that are contained within an LCVR comprising the amino acid sequence set forth in SEQ ID NO: 88; or (b) an HCVR comprising three heavy chain complementarity determining regions (HCDR1, HCDR2, and HCDR3) that are contained within an HCVR comprising the amino acid sequence set forth in SEQ ID NO: 34; and an LCVR comprising three light chain complementarity determining regions (LCDR1, LCDR2, and LCDR3) that are contained within an LCVR comprising the amino acid sequence set forth in SEQ ID NO: 42.

2. The method of claim 1, wherein the condition or disease is selected from the group consisting of Donohue syndrome, Rabson-Mendenhall syndrome, Type A insulin resistance, Type B insulin resistance, HAIR-AN (hyperandrogenism, insulin resistance, and acanthosis nigricans) syndrome, pseudoacromegaly, Alstrom syndrome, myotonic dystrophy, Werner's syndrome, lipodystrophy, cirrhosis, monogenic morbid obesity, hyperproinsulinemia, carboxypeptidase E deficiency, defective arginine metabolism, and Bardet-Biedl syndrome.

3. The method of claim 1, wherein insulin degrading protease activity is detected in the patient sera.

4. The method of claim 1, wherein neutralizing anti-insulin antibodies or anti-insulin receptor antibodies are detected in the patient sera.

5. The method of claim 1, wherein the GCGR antagonist is administered concomitantly with insulin.

6. The method of claim 1, wherein the composition is administered to the patient in combination with at least one additional therapeutic agent.

7. The method of claim 6, wherein the at least one additional therapeutic agent is selected from the group consisting of insulin, a biguanide, hIGF1, leptin, pioglitazone, vildagliptin, acarbose, alpha-glycosidase inhibitors, L-arginine, dipeptidyl-peptidase-4 inhibitors, insulin secretagogues, amylin receptor agonists, insulin sensitizers, FGF21, SGLT2 inhibitors, SGLT1 inhibitors, GLP-1 agonists, GLP-1 receptor activators, β3 adrenergic agonists, NPR1 agonists, NPR3 antagonists, tri-iodothyronine, a GCG inhibitor, and a second GCGR antagonist.

8. The method of claim 7, wherein the insulin secretagogues are selected from the group consisting of sulfonylureas, ATP-sensitive K channel antagonists, and meglitinides.

9. The method of claim 7, wherein the insulin sensitizer is thiazolidinedione or rosiglitazone.

10. The method of claim 1, wherein the isolated human antibody or antigen-binding fragment thereof comprises:

(a) an HCDR1 comprising the amino acid sequence set forth in SEQ ID NO: 72;

an HCDR2 comprising the amino acid sequence set forth in SEQ ID NO: 74;

an HCDR3 comprising the amino acid sequence set forth in SEQ ID NO: 76;

an LCDR1 comprising the amino acid sequence set forth in SEQ ID NO: 80;

an LCDR2 comprising the amino acid sequence of AAS; and an LCDR3 comprising the amino acid sequence set forth in SEQ ID NO: 84; or (b) an HCDR1 comprising the amino acid sequence set forth in SEQ ID NO: 36;

an HCDR2 comprising the amino acid sequence set forth in SEQ ID NO: 38;

an HCDR3 comprising the amino acid sequence set forth in SEQ ID NO: 40;

an LCDR1 comprising the amino acid sequence set forth in SEQ ID NO: 44;

an LCDR2 comprising the amino acid sequence of LGS; and an LCDR3 comprising the amino acid sequence set forth in SEQ ID NO: 48.

11. The method of claim 1, wherein the isolated antibody or antigen-binding fragment thereof comprises:

(a) an HCVR amino acid sequence as set forth in SEQ ID NO: 86 and an LCVR amino acid sequence as set forth in SEQ ID NO: 88; or (b) an HCVR amino acid sequence as set forth in SEQ ID NO: 34 and an LCVR amino acid sequence as set forth in SEQ ID NO: 42.

12. The method of claim 1, wherein the ketone bodies are beta-hydroxybutyrate.

13. The method of claim 1, wherein the patient exhibits elevated levels of blood glucose.

14. The method of claim 1, wherein the amount and/or dosage of insulin necessary to treat the patient is reduced.

15. The method of claim 14, wherein the GCGR antagonist is administered concomitantly with insulin.

16. The method of claim 14, wherein the amount and/or dosage of insulin may be reduced by about 30% to about 95% when administered concomitantly with the GCGR antagonist.

17. The method of claim 14, wherein the amount and/or dosage of insulin may be reduced by about 90% when administered concomitantly with the GCGR antagonist.

18. The method of claim 1, wherein β-cell mass in the patient is increased relative to the β-cell mass prior to treatment.

* * * * *